US012756798B2

(12) United States Patent
Katra et al.

(10) Patent No.: US 12,756,798 B2
(45) **Date of Patent: *Oct. 6, 2026**

(54) POST OPERATIVE IMPLANTATION SITE MONITORING

(71) Applicant: Medtronic, Inc., Minneapolis, MN (US)

(72) Inventors: Rodolphe Katra, Blaine, MN (US); Amie Bucksa, Ham Lake, MN (US); Niranjan Chakravarthy, Singapore (SG)

(73) Assignee: Medtronic, Inc., Minneapolis, MN (US)

( * ) Notice: Subject to any disclaimer, the term of this patent is extended or adjusted under 35 U.S.C. 154(b) by 48 days.

This patent is subject to a terminal disclaimer.

(21) Appl. No.: 19/043,572

(22) Filed: Feb. 3, 2025

(65) Prior Publication Data

US 2025/0184455 A1 Jun. 5, 2025

Related U.S. Application Data

(63) Continuation of application No. 17/215,419, filed on Mar. 29, 2021, now Pat. No. 12,262,153.

(Continued)

(51) Int. Cl.
*H04N 7/18* (2006.01)
*A61B 90/00* (2016.01)

(Continued)

(52) U.S. Cl.
CPC ........... *H04N 7/188* (2013.01); *A61B 90/361* (2016.02); *G06N 20/00* (2019.01); *G06T 7/0012* (2013.01);

(Continued)

(58) Field of Classification Search
None
See application file for complete search history.

(56) References Cited

U.S. PATENT DOCUMENTS 5,321,618 A 6/1994 Gessman
6,108,635 A 8/2000 Herren et al.

(Continued)

FOREIGN PATENT DOCUMENTS

CN 101060815 A 10/2007
CN 103562967 A 2/2014

(Continued)

OTHER PUBLICATIONS

First Office Action and Search Report, and translation thereof, from counterpart Chinese Application No. 202180031171.9 dated Mar. 17, 2025, 11 pp.

(Continued)

*Primary Examiner* — Peter D Le

(74) *Attorney, Agent, or Firm* — Shumaker & Sieffert, P.A.

(57) ABSTRACT

Techniques for remote monitoring of a patient and corresponding medical device(s) are described. The remote monitoring comprises determining identification data and identifying implantable medical device (IMD) information, initiating an imaging device and determining an imaging program, receiving one or more frames of image data including image(s) of an implantation site, identifying an abnormality at the implantation site, triggering a supplemental image capture mode, receiving one or more supplemental images of the implantation site, and outputting the one or more supplemental images of the implantation site.

21 Claims, 25 Drawing Sheets

Related U.S. Application Data

(60) Provisional application No. 63/018,063, filed on Apr. 30, 2020.

(51) Int. Cl.

| | |
|---|---|
| ***G06N 20/00*** | (2019.01) |
| ***G06T 7/00*** | (2017.01) |
| ***G16H 10/60*** | (2018.01) |
| ***G16H 30/20*** | (2018.01) |
| ***G16H 30/40*** | (2018.01) |
| ***G16H 40/40*** | (2018.01) |
| ***G16H 40/67*** | (2018.01) |
| ***G16H 50/70*** | (2018.01) |
| ***H04N 23/62*** | (2023.01) |
| *A61N 1/372* | (2006.01) |
| *G16H 15/00* | (2018.01) |
| *G16H 40/20* | (2018.01) |
| *G16H 50/20* | (2018.01) |

(52) U.S. Cl.
CPC ............. *G16H 10/60* (2018.01); *G16H 30/20* (2018.01); *G16H 30/40* (2018.01); *G16H 40/40* (2018.01); *G16H 40/67* (2018.01); *G16H 50/70* (2018.01); *H04N 23/62* (2023.01); *A61N 1/37211* (2013.01); *G06T 2207/10016* (2013.01); *G06T 2207/30004* (2013.01); *G16H 15/00* (2018.01); *G16H 40/20* (2018.01); *G16H 50/20* (2018.01)

(56) References Cited

U.S. PATENT DOCUMENTS

| | | | |
|---|---|---|---|
| 6,442,432 | B2 | 8/2002 | Lee |
| 6,497,655 | B1 | 12/2002 | Linberg et al. |
| 8,301,254 | B2 | 10/2012 | Mosesov et al. |
| 8,551,092 | B2 | 10/2013 | Morgan et al. |
| 9,055,974 | B2 | 6/2015 | Goetz |
| 9,615,744 | B2 | 4/2017 | Denison et al. |
| 10,064,551 | B2 | 9/2018 | Cosentino et al. |
| 10,143,847 | B1 | 12/2018 | Edmonson et al. |
| 10,729,502 | B1 | 8/2020 | Wolf et al. |
| 10,861,604 | B2 | 12/2020 | Bates |
| 11,074,760 | B2 | 7/2021 | Bidne et al. |
| 11,141,115 | B2 | 10/2021 | Benson et al. |
| 11,756,681 | B2 | 9/2023 | Katra et al. |
| 11,786,144 | B2 | 10/2023 | Crawford et al. |
| 12,260,555 | B2 | 3/2025 | Jordan |
| 12,262,153 | B2 | 3/2025 | Katra et al. |
| 2002/0032470 | A1 | 3/2002 | Linberg |
| 2004/0116981 | A1 | 6/2004 | Mazar |
| 2004/0152972 | A1 | 8/2004 | Hunter |
| 2005/0065555 | A1 | 3/2005 | Er |
| 2005/0171411 | A1 | 8/2005 | KenKnight et al. |
| 2005/0192844 | A1 | 9/2005 | Esler et al. |
| 2005/0228693 | A1 | 10/2005 | Webb et al. |
| 2005/0283198 | A1 | 12/2005 | Haubrich et al. |
| 2006/0189869 | A1 | 8/2006 | Sela et al. |
| 2007/0203538 | A1 | 8/2007 | Stone et al. |
| 2007/0276309 | A1 | 11/2007 | Xu et al. |
| 2008/0051638 | A1 | 2/2008 | Iliff |
| 2008/0071161 | A1 | 3/2008 | Jaeb et al. |
| 2008/0097793 | A1 | 4/2008 | Dicks et al. |
| 2008/0262323 | A1 | 10/2008 | Gerber et al. |
| 2008/0317195 | A1 | 12/2008 | Kobayashi et al. |
| 2009/0088620 | A1 | 4/2009 | Zagorchev et al. |
| 2010/0022990 | A1 | 1/2010 | Karpowicz et al. |
| 2010/0036209 | A1 | 2/2010 | Ferren et al. |
| 2010/0185064 | A1 | 7/2010 | Bandic et al. |
| 2010/0316259 | A1 | 12/2010 | Liu et al. |
| 2010/0324936 | A1 | 12/2010 | Vishnubbatla et al. |
| 2011/0117025 | A1 | 5/2011 | Dacosta et al. |
| 2012/0044070 | A1 | 2/2012 | Putrino |
| 2012/0232339 | A1 | 9/2012 | Csiky |
| 2012/0274804 | A1 | 11/2012 | Tanabe |
| 2013/0012835 | A1 | 1/2013 | Chono |
| 2013/0053657 | A1 | 2/2013 | Ziarno et al. |
| 2013/0188848 | A1 | 7/2013 | Helm et al. |
| 2013/0303869 | A1 | 11/2013 | Rebec et al. |
| 2014/0059237 | A1 | 2/2014 | Pittman et al. |
| 2014/0088990 | A1 | 3/2014 | Nawana et al. |
| 2014/0122120 | A1 | 5/2014 | Doudian |
| 2014/0276928 | A1 | 9/2014 | Vanderpool et al. |
| 2014/0328517 | A1 | 11/2014 | Gluncic |
| 2014/0378964 | A1 | 12/2014 | Pearson |
| 2015/0089590 | A1 | 3/2015 | Krishnan et al. |
| 2015/0104085 | A1 | 4/2015 | Schilling et al. |
| 2015/0112705 | A1 | 4/2015 | Neville |
| 2015/0133945 | A1 | 5/2015 | Dushyant et al. |
| 2015/0150457 | A1 | 6/2015 | Wu et al. |
| 2015/0286787 | A1 | 10/2015 | Chen et al. |
| 2016/0069919 | A1 | 3/2016 | Holmes et al. |
| 2016/0192878 | A1 | 7/2016 | Hunter |
| 2016/0228034 | A1 | 8/2016 | Gluncic |
| 2016/0310031 | A1 | 10/2016 | Sarkar |
| 2017/0084024 | A1 | 3/2017 | Gurevich |
| 2017/0312023 | A1 | 11/2017 | Harlev et al. |
| 2017/0325897 | A1 | 11/2017 | Isaacs et al. |
| 2018/0028079 | A1 | 2/2018 | Gurevich et al. |
| 2018/0070875 | A1 | 3/2018 | Kshetrapal |
| 2018/0114591 | A1 | 4/2018 | Pribanic et al. |
| 2018/0310828 | A1 | 11/2018 | DiMaio et al. |
| 2018/0365833 | A1 | 12/2018 | Dhaini et al. |
| 2019/0073772 | A1 | 3/2019 | Ishihara et al. |
| 2019/0122330 | A1 | 4/2019 | Saget et al. |
| 2020/0100881 | A1 | 4/2020 | Emery, III et al. |
| 2020/0111213 | A1 | 4/2020 | Chacon et al. |
| 2020/0129136 | A1 | 4/2020 | Harding et al. |
| 2020/0160510 | A1 | 5/2020 | Lindemer et al. |
| 2020/0327670 | A1 | 10/2020 | Connor |
| 2020/0357513 | A1 | 11/2020 | Katra et al. |
| 2020/0364864 | A1 | 11/2020 | Shanbhag et al. |
| 2021/0045640 | A1 | 2/2021 | Poltorak |
| 2021/0093254 | A1 | 4/2021 | Sarkar et al. |
| 2021/0343017 | A1 | 11/2021 | Jordan |
| 2021/0344880 | A1 | 11/2021 | Katra et al. |
| 2022/0047894 | A1 | 2/2022 | Kenney et al. |
| 2023/0368910 | A1 | 11/2023 | Katra et al. |

FOREIGN PATENT DOCUMENTS

| | | | |
|---|---|---|---|
| CN | 103961722 | A | 8/2014 |
| CN | 104335211 | A | 2/2015 |
| CN | 109310317 | A | 2/2019 |
| CN | 109767822 | A | 5/2019 |
| KR | 200476682 | Y1 | 3/2015 |
| KR | 20160023849 | A | 3/2016 |
| WO | 2008013722 | | 1/2008 |
| WO | 2009089278 | A1 | 7/2009 |
| WO | 2013082289 | A1 | 6/2013 |
| WO | 2013152077 | A1 | 10/2013 |
| WO | 2013188470 | | 12/2013 |
| WO | 2014040061 | A1 | 3/2014 |
| WO | 2014123978 | A2 | 8/2014 |
| WO | 2015200704 | | 12/2015 |
| WO | 2017083494 | A1 | 5/2017 |
| WO | 2017096224 | A1 | 6/2017 |
| WO | 2017106858 | | 6/2017 |
| WO | 2018/144715 | A1 | 8/2018 |
| WO | 2018/210692 | A1 | 11/2018 |
| WO | 2019/030384 | A1 | 2/2019 |
| WO | 2019/096828 | | 5/2019 |
| WO | 2019/136559 | | 7/2019 |

OTHER PUBLICATIONS

Reply Brief from U.S. Appl. No. 18/355,260, filed Sep. 24, 2025, 11 pp.
Decision on Appeal from U.S. Appl. No. 18/355,260 dated Apr. 30, 2026, 30 pp.

(56) References Cited

OTHER PUBLICATIONS

Examiner's Answer from U.S. Appl. No. 18/355,260 dated Aug. 22, 2025, 12 pp.
Appeal Brief from U.S. Appl. No. 18/355,260, filed Jul. 9, 2025, 34 pp.
"SBP scientist helps develop smartphone app for one-hour identification of bacteria," Sanford Burnham Prebys Medical Discovery Institute, Sep. 20, 2018, 3 pp.
"TYRX® Comments on Medicare Decision to Stop Paying for Infections Following Pacemaker or Defibtillator Implants," Pappas Capital, LLC, retrieved from http://www.pappas-capital.com/tyrx-comments-medicare-decision-stop-paying-infections-following-pacemaker-or-defibrillator-implants/, Aug. 2, 2012, 1 pp.
"Ugandan Student Create Vaginal infection Detection App," retrieved from https://herhealthuganda.com/ugandan-students-create-vaginal-infection-detection-app/, Oct. 17, 2017, 2 pp.
Baddour et al., "Update on Cardiovascular Implantable Electronic Device Infections and Their Management," American Heart Association, Inc., vol. 121, Issue 3, Jan. 26, 2010, 20 pp.
Daneman et al., "The predictors and economic burden of early-, mid-, and late-onset cardiac implantable electronic device infections: a retrospective cohort study in Ontario, Canada," Clin Microbiol Infect, Feb. 2019, 6 pp.
Dillon, "User Interface Design," MacMillian Encyclopedia of Cognitive Science, vol. 4, 2003, 16 pp. (Applicant points out, in accordance with MPEP 609.04(a), that the year of publication, 2003, is sufficiently earlier than the effective U.S. filing date, so that the particular month of publication is not in issue.).
Eby et al., "Analysis of Cardiac Implantable Electronic Device Infection Costs at One Year in a Large United States Health Care Organization," Poster presented at IDWeek, San Diego, CA, Oct. 4-8, 2017, 1 pp.
Greenspon et al., "16-Year Tends in the Infection Burden for Pacemakers and Implantable Cardioverter-Defibrillators in the United States," J Am Coll Cardiol, vol. 58., No. 10, 2011, 6 pp. (Applicant points out, in accordance with MPEP 609.04(a), that the year of publication, 2011, is sufficiently earlier than the effective U.S. filing date, so that the particular month of publication is not in issue.).
Gunter et al., "Evaluating Patient Usability of an Image-Based Mobile Health Platform for Postoperative Wound Monitoring," JMIR Mhealth Unhealth, vol. 4, Issue 3, Sep. 28, 2016, 15 pp.
Gutiérrez-Carretero et al., "Infections on Cardiovascular Implantable Electronic Devices: a Critical Review," Medical Research Archives, vol. 7, issue 3, Mar. 2019, 64 pp.
Harper et al., "Clinical presentation of CIED infection following initial implant versus reoperation for generator change or lead addition," Open Heart, British Cardiovascular Society, 2018, 7 pp. (Applicant points out, in accordance with MPEP 609.04(a), that the year of publication, 2011, is sufficiently earlier than the effective U.S. filing date, so that the particular month of publication is not in issue.).
Henrickson et al., "Antibacterial Envelope Is Associated With Low Infection Rates After Implantable Cardioverter-Defibrillator and Cardiac Resynchronization Therapy Device Replacement," JACC EP. May 2017, 10 pp.
International Search Report and Written Opinion of International Application No. PCT/US2021/028090, mailed Aug. 31, 2021, 9 pp.
Kirsh, "This smartphone app could detect infectious diseases," retrieved from https://www.medicaldesignandoutsourcing.com/this-smartphone-app-could-detect-infectious-diseases/, Nov. 6, 2018, 15 pp.
Li et al., "Imaging in Chronic Wound Diagnostics," Advances in Wound Care vol. 9, No. 5, Mar. 19, 2020, 19 pp.
Mittal et al., "Cardiac implantable electronic device infections: Incidence, risk factors, and the effect of the AigisRx antibacterial envelope," Heart Rhythm Society, Mar. 7, 2014, 7 pp.
Nielsen et al., "Infected cardiac-implantable electronic devices: prevention, diagnosis, and treatment," European Heart Journal, Mar. 6, 2015, 7 pp.
Prosecution History from U.S. Appl. No. 16/863,590, dated Aug. 3, 2021 through Aug. 17, 2023. 192 pp.
Prosecution History from U.S. Appl. No. 17/215,419, dated Feb. 15, 2023 through Feb. 26, 2025, 251 pp.
Prosecution History from U.S. Appl. No. 17/217,632, dated Oct. 13, 2023 through Feb. 13, 2025, 231 pp.
Prosecution History from U.S. Appl. No. 18/355,260, dated Mar. 4, 2024 through Apr. 17, 2025, 267 pp.
Shandrow, "This Smart Skin-Scanning App Could Save Your Life," retrieved from https://wwww.entrpreneur.com/article/237953, Oct. 2, 2014, 8 pp.
Sohail, "Cardiovascular Implantable Electronic Device (CIED) Infection," retrieved from https://www.infectiousdiseaseadvisor.com/home/decision-support-in-medicine/infectious-diseases/cardiovascular-implantable-electronic-device-cied-infection/, Jan. 20, 2019, 12 pp.
Strachan, "Value-Based Healthcare: What role does HTA play?," HTAi 2018 Annual Meeting Vancouver Canada, Jun. 1-5, 2018, 14 pp.
Strickland, "Diagnosing Ear Infections With Your Smartphone," retrieved from https://www.wbur.org/hereandnow/2014/12/17/ear-infections-app, Dec. 17, 2014, 4 pp.
Tarakji, "WRAP-IT Substudy Provides Strong Prospective Support for CIED Infection Prevention," Heart, Vascular, and Thoracic Research, retrieved from https://consultqd.clevelandclinic.org/wrap-it-substudy-provides-strong-prospective-support-for-cied-infection-prevention/, Nov. 18, 2019, 3 pp.

POST OPERATIVE IMPLANTATION SITE MONITORING

This application is a continuation of U.S. patent application Ser. No. 17/215,419, filed Mar. 29, 2021, and entitled "POST OPERATIVE IMPLANTATION SITE MONITORING," which claims priority to and the benefit of U.S. Provisional Application Ser. No. 63/018,063, filed Apr. 30, 2020, the entire content of each of which is incorporated herein by reference.

FIELD

This disclosure relates to medical devices, and in some specific examples, relates to computing devices configured to evaluate a patient's recovery from implantation of a medical device that is presently implanted in the patient.

BACKGROUND

Medical devices may be used to treat a variety of medical conditions. Example medical devices include implantable medical devices (IMDs), such as cardiac or cardiovascular electronic implantable devices (CIEDs). An IMD, also referred to at times as an "implanted medical device," may include a device implanted in a patient at a surgically or procedurally prepared implantation site. The IMD may include a diagnostic device configured to diagnose various ailments of a patient, monitor a health status of the patient, etc. In addition, or alternatively, an IMD may also be configured to deliver electrical stimulation therapy to a patient via electrodes, such as implanted electrodes, where the device may be configured to stimulate the heart, nerves, muscles, brain tissue, etc. In any case, the IMD may, in some instances, include a battery powered component, such as when referring to implantable cardiac pacemakers, implantable cardioverter-defibrillators (ICDs), other electrical stimulators including spinal cord, deep brain, nerve, and muscle stimulators, infusion devices, cardiac and other physiologic monitors, cochlear implants, etc. In such instances, the battery powered component of the IMD may be implanted, such as at a surgically or procedurally prepared implantation site. In addition, associated devices, such as elongated medical electrical leads or drug delivery catheters, can extend from the IMD to other subcutaneous implantation sites or in some instances, deeper into the body, such as to organs or various other implantation sites.

While preparation and implantation are conducted in a sterile field, and the IMD components are packaged in sterile containers or sterilized prior to introduction into the sterile field, there can still be a risk of introduction of microbes into the sites. Implanting clinicians therefore typically apply disinfectant or antiseptic agents to the skin at the surgical site prior to surgery, directly to the site before the incision is closed, and prescribe oral antibiotics for the patient to ingest during recovery. Despite these precautions, infections can occur.

Accordingly, infection associated with implantation of medical devices remains a health and economic concern. If an infection associated with an IMD occurs, explanting the device can often be the only appropriate course of action. In addition, once a site becomes infected, the infection can migrate, e.g., along the lead or catheter to locations in which the lead and/or catheter are implanted. Removal of a chronically implanted lead or catheter, e.g., in response to such an infection, can be difficult. Aggressive systemic drug treatment is prescribed to treat such infections. However, early detection of infections associated with IMDs may allow for earlier intervention, resulting in fewer device explants.

In some instances, patients who have had certain medical devices implanted, such as CIEDs, are required to have a post-implant follow-up consultation visit with a healthcare professional (HCP). The HCP visit typically occurs anywhere from a few days to a few weeks after the implantation. These visits are non-remarkable and brief in the majority of cases, at a level as high as over 90%. However, the post-implant follow-up visit may still constitute for the patient a required checkpoint with the HCP. In some cases, this follow-up visit uncovers a potential infection or device-related complications that potentially warrant clinical intervention.

SUMMARY

While the actual follow-up consultation visits with the HCP tend to be relatively short, the visits can still constitute a burden on the patient's life, the physician's clinic, and on the healthcare system overall. Aspects of this disclosure are directed to one or more computing devices having processing circuitry, where the processing circuitry is configured to facilitate or simulate a virtual check-in for a patient, such as a virtual follow-up or other wellness check, where a patient and/or physician may check on the status of an IMD, specifically an implantation site of an IMD.

A system of processing circuitry of the one or more computing devices may implement various tools and techniques (hereinafter, "tools," a system of processors, or a processing circuitry system) in order to provide a virtual check-in for the patient. The processing circuitry system may be configured to provide an option for the patient to engage in a virtual check-in process as part of a post-implant evaluation, for which the patient can undergo a virtual check-in process remotely, as in remotely from a formal doctor's office setting or other HCP setting. In some examples, processing circuitry of a mobile or portable computing device may be configured to manage the virtual check-in process, such that a user may be able to effectively navigate the check-in process from any remote location. In addition, the processing circuitry system may communicate patient and/or medical device data between various computing devices (e.g., end-user mobile devices, camera devices, wearable devices, edge devices, etc.). In some examples, the processing circuitry system may be configured to manage the check-in process to ensure proper interaction with the check-in tools, such that the system may accurately determine whether any complications have arisen with the patient and/or the IMD. The processing circuitry system may communicate such information over a network and/or through implementation of various communication protocols.

In some instances, the processing circuitry system may implement the virtual check-in process in a secure setting, such as on an authenticated mobile computing device and/or over a secure data network. In some instances, the processing circuitry system may implement the virtual check-in process on a mobile device configured to perform one or more of the various techniques of this disclosure, with or without the assistance of other devices (e.g., network devices). That is, the mobile device may operate various software tools configured to perform the virtual check-in process. A patient may then conduct an entire session of the virtual check-in process without network access or with limited network use as in the use of wireless communication with an edge device (e.g., an IoT device with additional processing resources to assist or perform the various check-in functions). The mobile device may, at a later point in time following the completion of a check-in session, synchronize the virtual check-in data with other network devices. In this way, a HCP may access the data at that time, where it might not be critical that the HCP access such data in real-time or near real-time as the patient conducts the particular check-in session.

In accordance with techniques of this disclosure, a processing circuitry system is configured to provide a site-check user interface (UI) to a user (e.g., the patient). The processing circuitry of a computing device may determine an imaging program configured to receive imaging data of an implantation site. In some instances, the imaging program may include UI program data. In such instances, processing circuitry of the computing device may implement the UI program data in order to provide an imaging program, via the UI, that is configured to allow a user to perform a site-check process, in accordance with one or more of the various techniques of this disclosure. The processing circuitry of a computing device may initialize imaging devices (e.g., one or more cameras, augmented reality imaging devices, etc.) that may be configured to operate according to various imaging modes (e.g., video capture mode, still-image mode, burst shot modes, infrared modes, motion photos modes, zooming modes, etc.), where the various imaging modes may be configured to supplement (e.g., complement) one another during an image capture process. The processing circuitry of the computing device may trigger (e.g., transition between) various imaging modes in order to obtain image(s) of an implantation site, and when warranted, supplemental image(s), for a site-check analysis. The processing circuitry of the computing device may cause such transitions based on one or more image captures. That is, the processing circuitry of the computing device may transition from a first image capture mode to a supplemental image capture mode based on an analysis of an obtained image, such as, an analysis for any abnormalities at the implantation site. The computing device may perform the analysis or in some instances, a separate device (e.g., an edge device, network server, etc.) may perform the analysis. The separate device may be in communication with the computing device of a user (e.g., smartphone, tablet, etc.) or may interface with communication circuitry of an imaging device, in cases where the imaging device is separate and/or different than the computing device.

In some examples, the processing circuitry of the computing device may execute an imaging program configured to provide a site-check UI to the user. In doing so, the processing circuitry of the computing device may generate UI program data and/or access UI program data from memory. Likewise, the processing circuitry of the computing device may generate imaging program data and/or access imaging program data from memory, where the imaging program data may define UI program data for a site-check UI. In some instances, the processing circuitry may access UI program data and/or imaging program data from a separate computing device of a virtual check-in computing system. In some instances, the processing circuitry of the computing device may tailor the imaging program (e.g., UI program data) to each particular user or class of users. In some instances, the processing circuitry system may tailor the imaging program by deploying various artificial intelligence (AI) algorithms and/or machine learning (ML) models that are configured to determine a UI that reflects the particular user or class of users and the one or more medical devices corresponding to the particular user or class of users. In any case, the processing circuitry system may be configured to provide, via a display device, a site-check UI to the user of a user-operated computing device.

In a non-limiting examples, the implantation site-check process may be implemented as part of a comprehensive UI that may include multiple interactive UI check-in elements configured to guide a patient systematically through a more comprehensive virtual check-in process, including a UI check-in element for initiating the implantation site-check process. The UI check-in elements may be configured to actively assist a particular patient with providing specific patient input to the system (e.g., images of an implantation site). The patient input may include specific types of information and particular amounts of information. In some examples, the processing circuitry system may use the information to, for example, identify various maladies of the patient, such as device pocket infections, or otherwise, identify abnormalities with an implantation site, the medical device, and/or the patient. In some examples, the processing circuitry system may deploy AI and/or ML models in order to evaluate input received via the UI in order to determine a status of the implantation site (e.g., a status of the IMD). In another example, the processing circuitry system may communicate input from the patient to a HCP. The processing circuitry system may, in turn, receive input from the HCP. In such instances, the processing circuitry system may determine, based on the HCP input, the status of the implantation site. In any case, the processing circuitry system may train the AI and/or ML models on patient input and/or on HCP input, where the processing circuitry system may obtain HCP input that, in some instances is based on the patient input (e.g., uploaded images of implantation site, ECG waveforms, etc.). Accordingly, the processing circuitry system may utilize information from multiple sources to determine various maladies of the patient (e.g., potential infections at the implantation site, abnormal healing of the implantation site, etc.). While described, in some instances, with reference to a comprehensive UI, the techniques of this disclosure are not so limited, and it will be understood that the site-check UI may be implemented as a stand-alone UI, that does not involve other UI elements of this disclosure (e.g., device check elements, etc.). That is, processing circuitry of the computing device may include non-site-check UI elements, in only some examples, in order to obtain patient and/or device data that may supplement, or in some instances, complement site-check information (e.g., implantation site images, series of images, imaging sequences, etc.).

It will be understood that the processing circuitry system of this disclosure may implement the various site-check techniques wholly separate or together with any one or more of the other UI check-in elements disclosed herein. In an illustrative and non-limiting example, a system of processors may implement the site-check techniques of this disclosure on a dedicated site-check camera device that is specifically configured to perform the site-check techniques of this disclosure. In another example, the processing circuitry system of this disclosure may implement the site-check techniques of this disclosure on a personal mobile device of a user configured to employ a software application specifically configured to perform the site-check techniques of this disclosure, such as by executing an imaging program in accordance with one or more techniques of this disclosure. In addition and in select instances, the software application may be further configured to generate additional UI data relating to additional UI check-in elements, such as the device check-in element or patient check-in element disclosed herein.

In some instances, a patient may perform such virtual checks periodically to check on a status of the implantation site. That is, the patient may perform wellness checks even after performing a number of virtual check-in sessions that were either mandated or recommended by a HCP following a surgical event of the patient.

The virtual check-in process can replace, and/or in some instances supplement, in-person HCP visits. In some examples, the processing circuitry system of this disclosure may use the results of the computing device-implemented check to determine whether or not to provide an indication to the patient, and in certain cases, a physician or other HCP, as to whether an in-person visit is warranted, or alternatively, if the IMD wound recovery is progressing with the patient as expected. In some instances, the processing circuitry system may obtain information from a user, via one computing device, such as a mobile telephone device, and evaluate the information, via another computing device, such as an edge device or a network server. In such instances, an edge device may deploy AI and/or ML models trained on medical device data, patient data, and/or heuristic data obtained from a network. The processing circuitry system may, in some instances, train the AI or ML models on data obtained from the computing device of the user (e.g., patient data, image data, imaging sequence data) and/or from data obtained directly from the medical devices of the patient. In such instances, those medical devices may be configured to communicate with an edge device, as well as a user computing device.

In one example, the disclosure provides a method of monitoring an implantation site of a patient of an IMD, the method comprising: determining, via a computing device, identification data for the patient; identifying, based at least in part on the identification data, IMD information that corresponds to the IMD; determining, based at least in part on the IMD information, an imaging program that defines one or more parameters for imaging the implantation site; initiating, by the computing device, an imaging device, the imaging device configured to capture, in accordance with the imaging program, one or more frames of image data; receiving, via the imaging device, at least one frame of the one or more frames, the at least one frame including an image of the implantation site; identifying, from the at least one frame of the image data, an abnormality at the implantation site; in response to identifying the abnormality, automatically triggering a supplemental image capture mode, wherein the imaging device, when operating in the supplemental image capture mode, is configured to capture one or more supplemental images of the implantation site; subsequent to triggering the supplemental image capture mode, receiving, by the computing device, the one or more supplemental images of the implantation site; and outputting, via the computing device, the one or more supplemental images of the implantation site.

In another example, the disclosure provides a system for monitoring an implantation site of a patient of an IMD, the system comprising: a memory configured to store image data; and one or more processors in communication with the memory. In such examples, the one or more processors of the system may be configured to: determine identification data for the patient; identify, based at least in part on the identification data, IMD information that corresponds to the IMD; determine, based at least in part on the IMD information, an imaging program that defines one or more parameters for imaging the implantation site; initiate an imaging device, the imaging device configured to capture, in accordance with the imaging program, one or more frames of the image data; receive, from the imaging device, at least one frame of the one or more frames, the at least one frame including an image of the implantation site; identify, from the at least one frame of the image data, an abnormality at the implantation site; in response to identifying the abnormality, automatically trigger a supplemental image capture mode, wherein the imaging device, when operating in the supplemental image capture mode, is configured to capture one or more supplemental images of the implantation site; subsequent to triggering the supplemental image capture mode, receive the one or more supplemental images of the implantation site; and output the one or more supplemental images of the implantation site.

The disclosure also provides non-transitory computer-readable media comprising instructions that cause a programmable processor to perform any of the techniques described herein. In an example, this disclosure provides a non-transitory computer-readable storage medium having stored thereon instructions that, when executed, cause one or more processors to: determine identification data for a patient, the patient having an IMD; identify, based at least in part on the identification data, IMD information that corresponds to the IMD; determine, based at least in part on the IMD information, an imaging program that defines one or more parameters for imaging an implantation site; initiate an imaging device, the imaging device configured to capture, in accordance with the imaging program, one or more frames of image data; receive, via the imaging device, at least one frame of the one or more frames, the at least one frame including an image of the implantation site; identify, from the at least one frame of the image data, an abnormality at the implantation site; in response to identifying the abnormality, automatically trigger a supplemental image capture mode, wherein the imaging device, when operating in the supplemental image capture mode, is configured to capture one or more supplemental images of the implantation site; subsequent to triggering the supplemental image capture mode, receive the one or more supplemental images of the implantation site; and output the one or more supplemental images of the implantation site.

The disclosure also provides means for performing any of the techniques described herein.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

Figure 1:
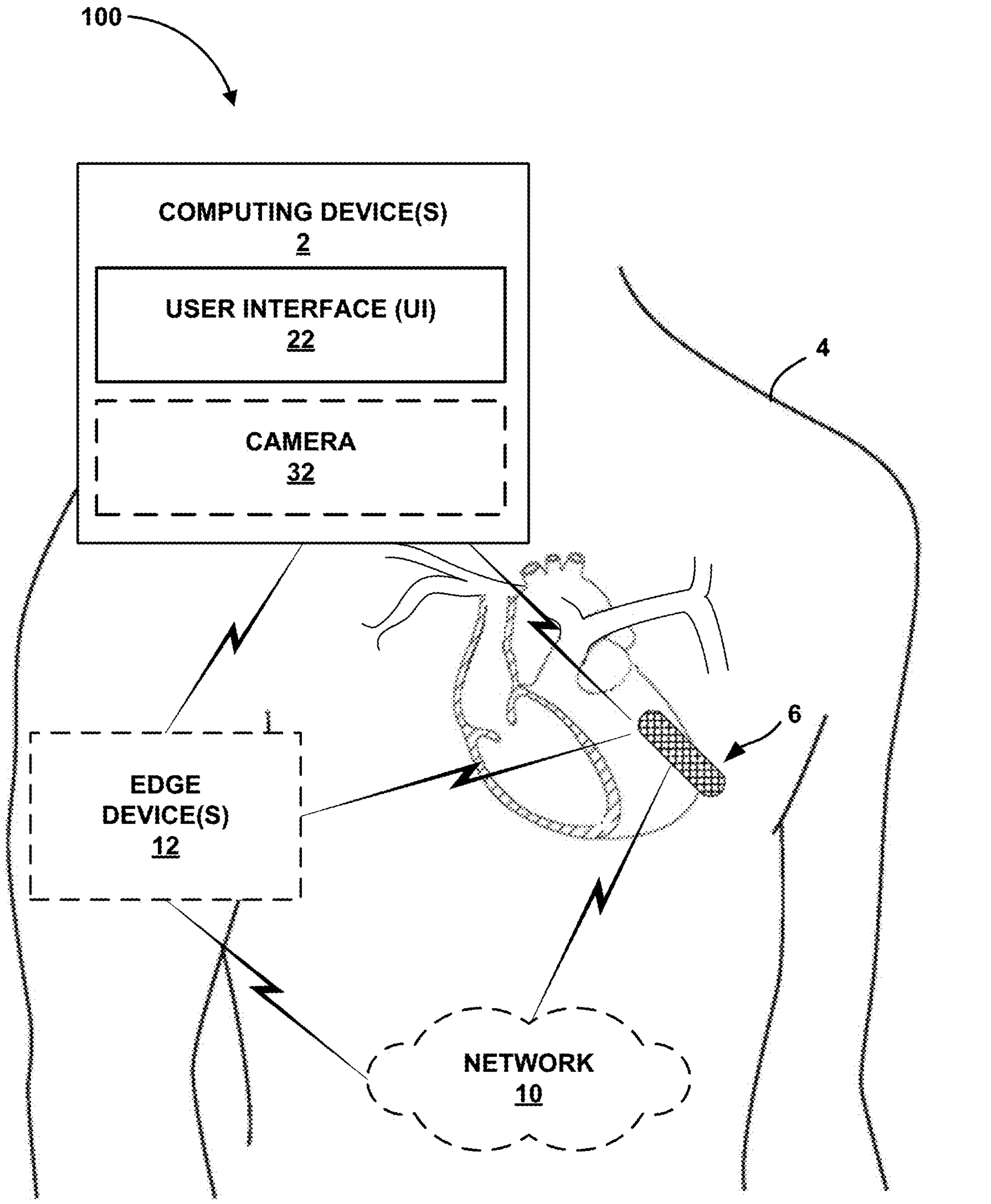
FIG. 1 illustrates the environment of an example monitoring system in conjunction with a patient, in accordance with one or more techniques disclosed herein.
Figure 4:
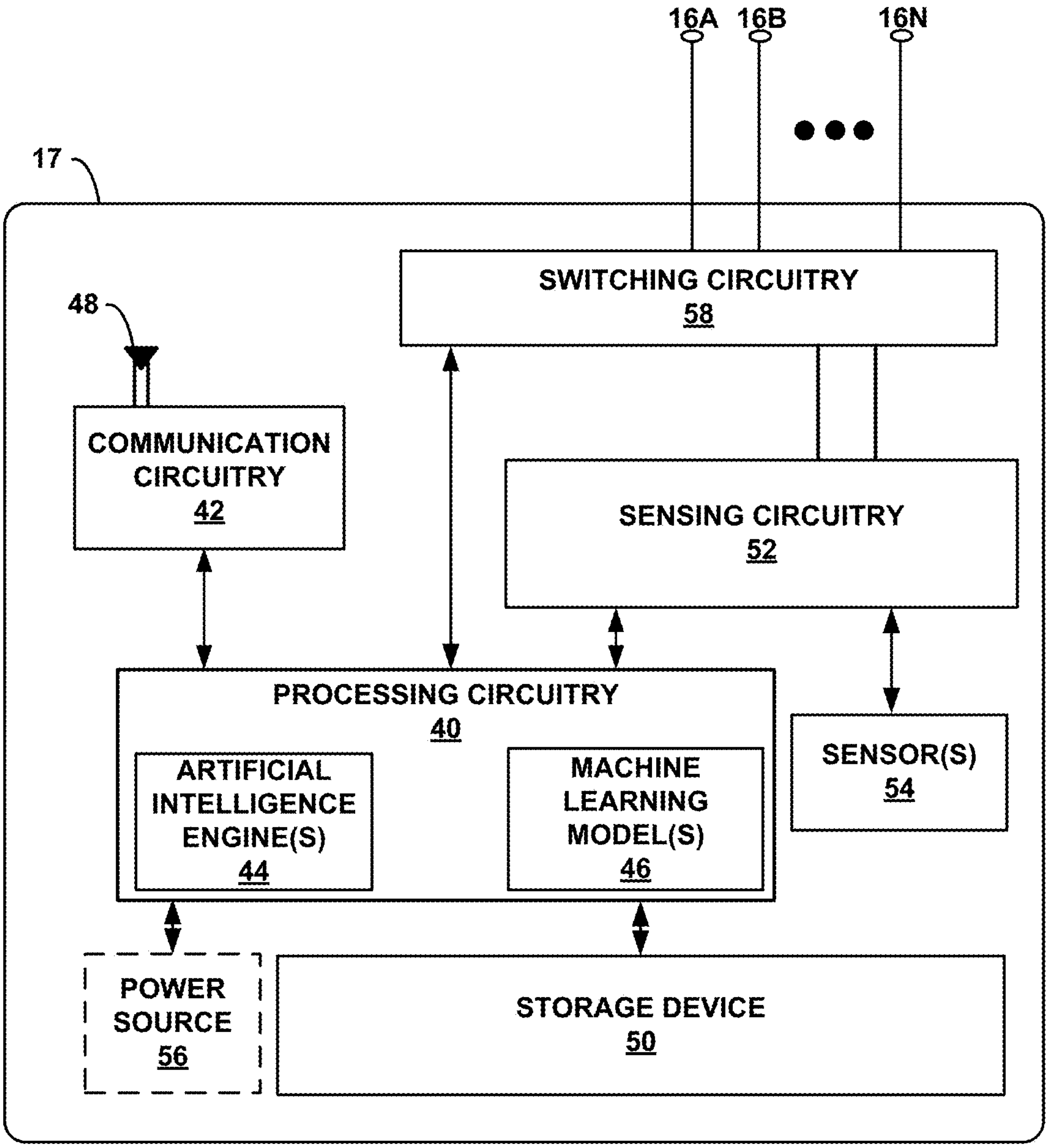

FIG. 4 is a functional block diagram illustrating an example configuration of a medical device of FIGS. 1 and/or 3, in accordance with one or more techniques disclosed herein.

Figure 2:
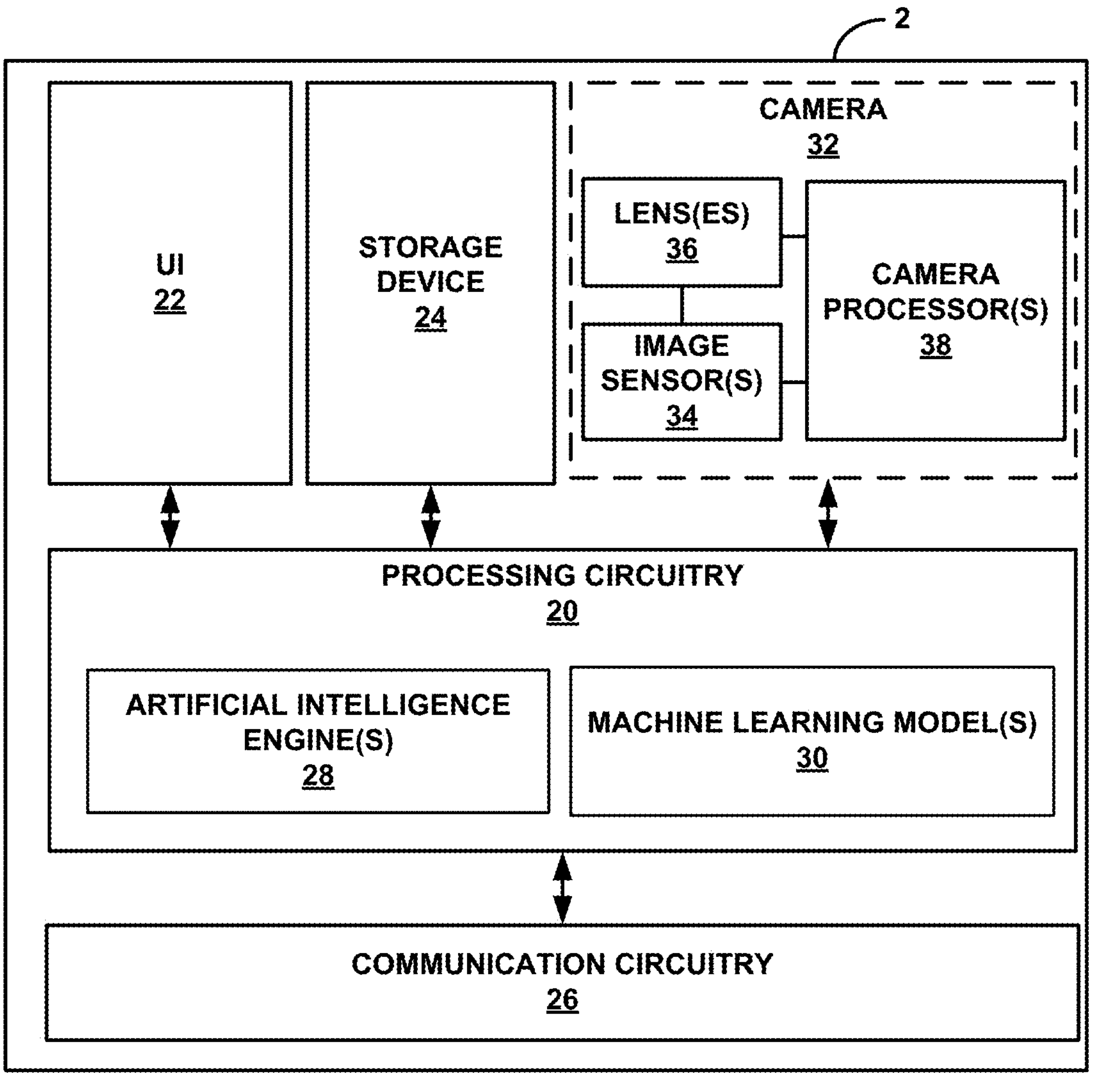
FIG. 2 is a functional block diagram illustrating an example configuration of an example computing device of FIG. 1, in accordance with one or more techniques disclosed herein.
Figure 3:
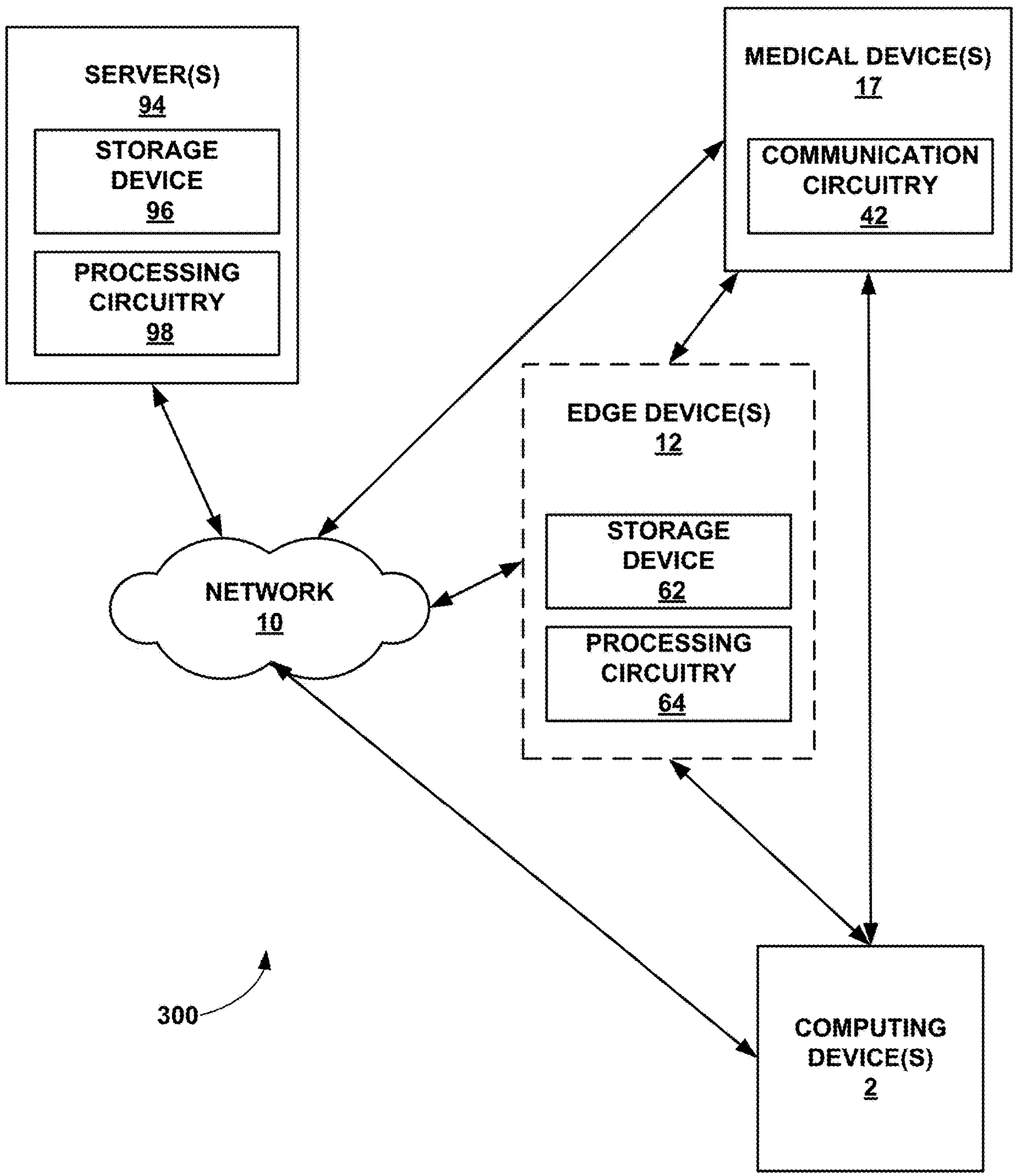
FIG. 3 is a block diagram illustrating an example network system that includes example computing device(s) of FIG. 1 or 2, a network, edge device(s), and server(s), in accordance with one or more techniques disclosed herein.
Figure 5:
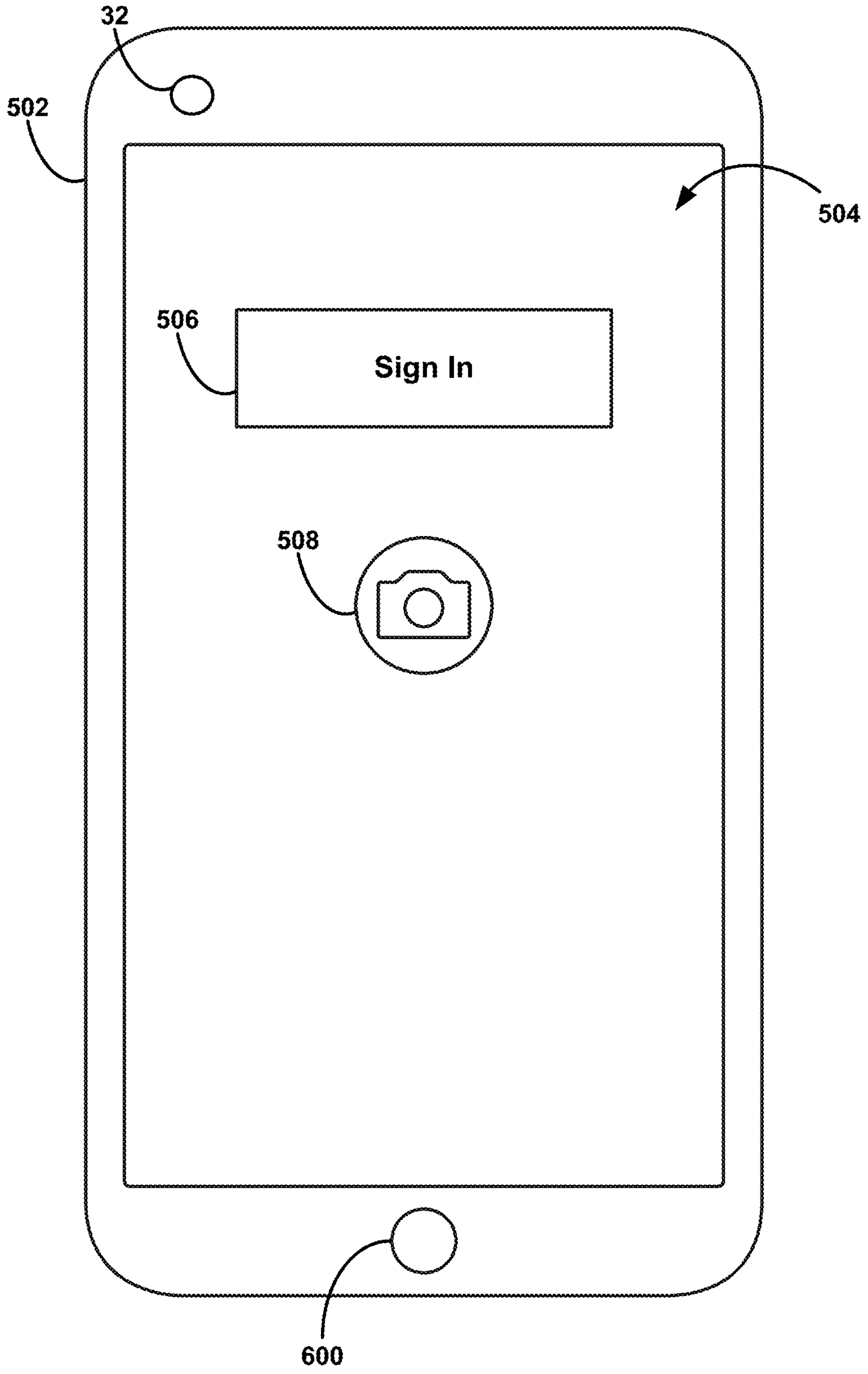

FIG. 5 is an example user interface (UI) visualization of an example computing device of FIG. 1, 2, or 3, in accordance with one or more techniques of this disclosure.

Figure 6:
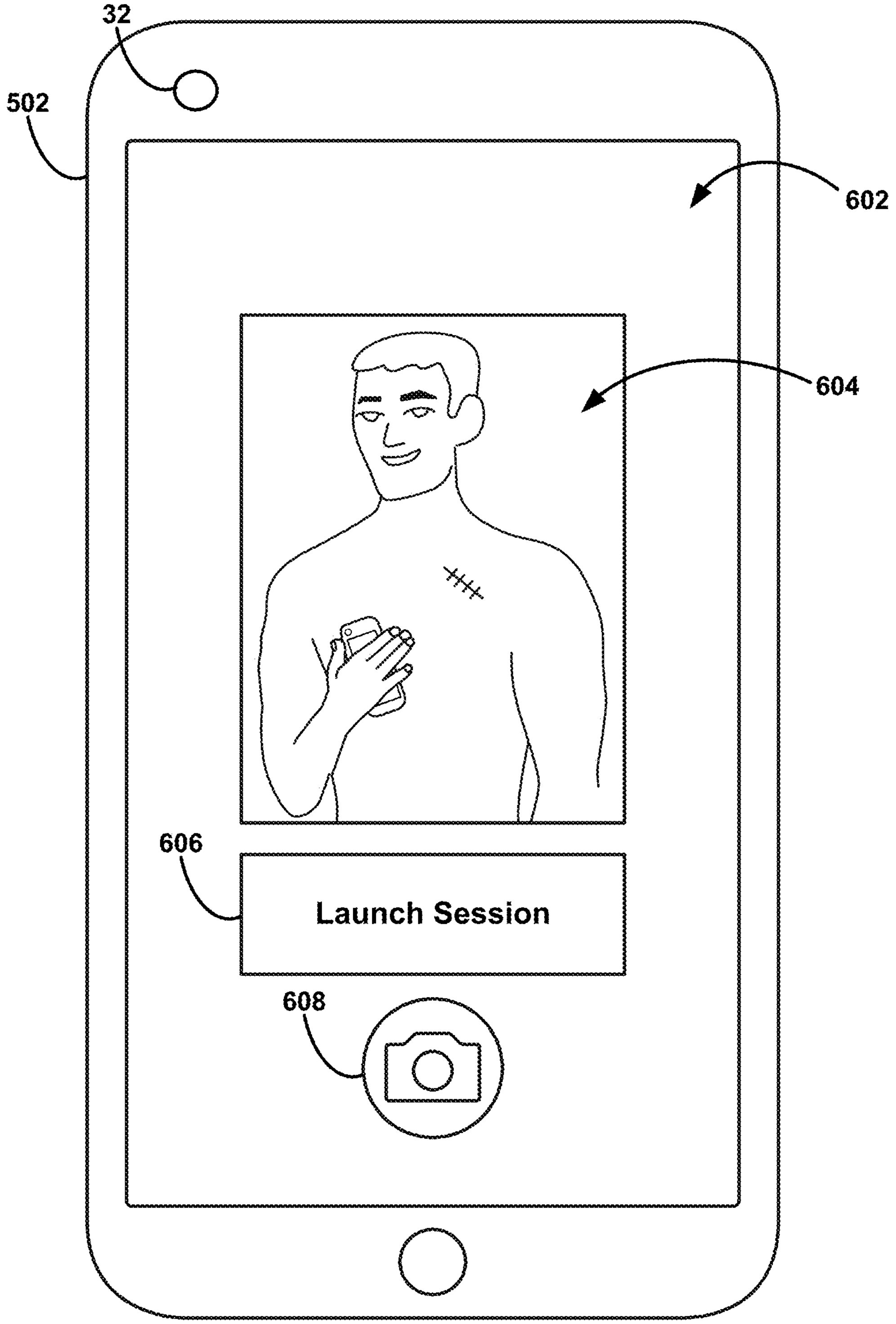

FIG. 6 is an UI visualization of an example launch session interface, in accordance with one or more techniques of this disclosure.

Figure 7:
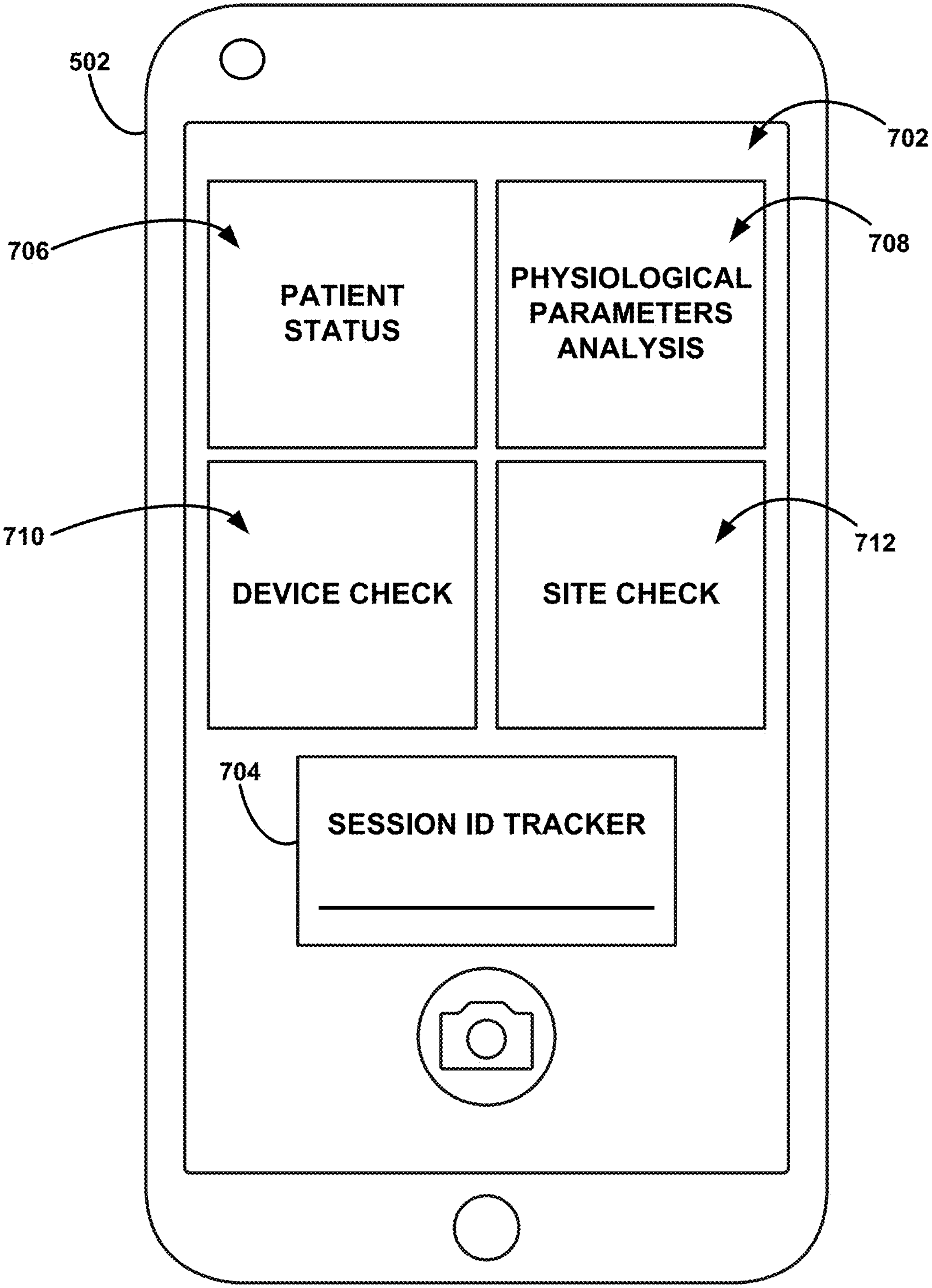

FIG. 7 is an UI visualization of an example menu interface, in accordance with one or more techniques of this disclosure.

Figure 8:
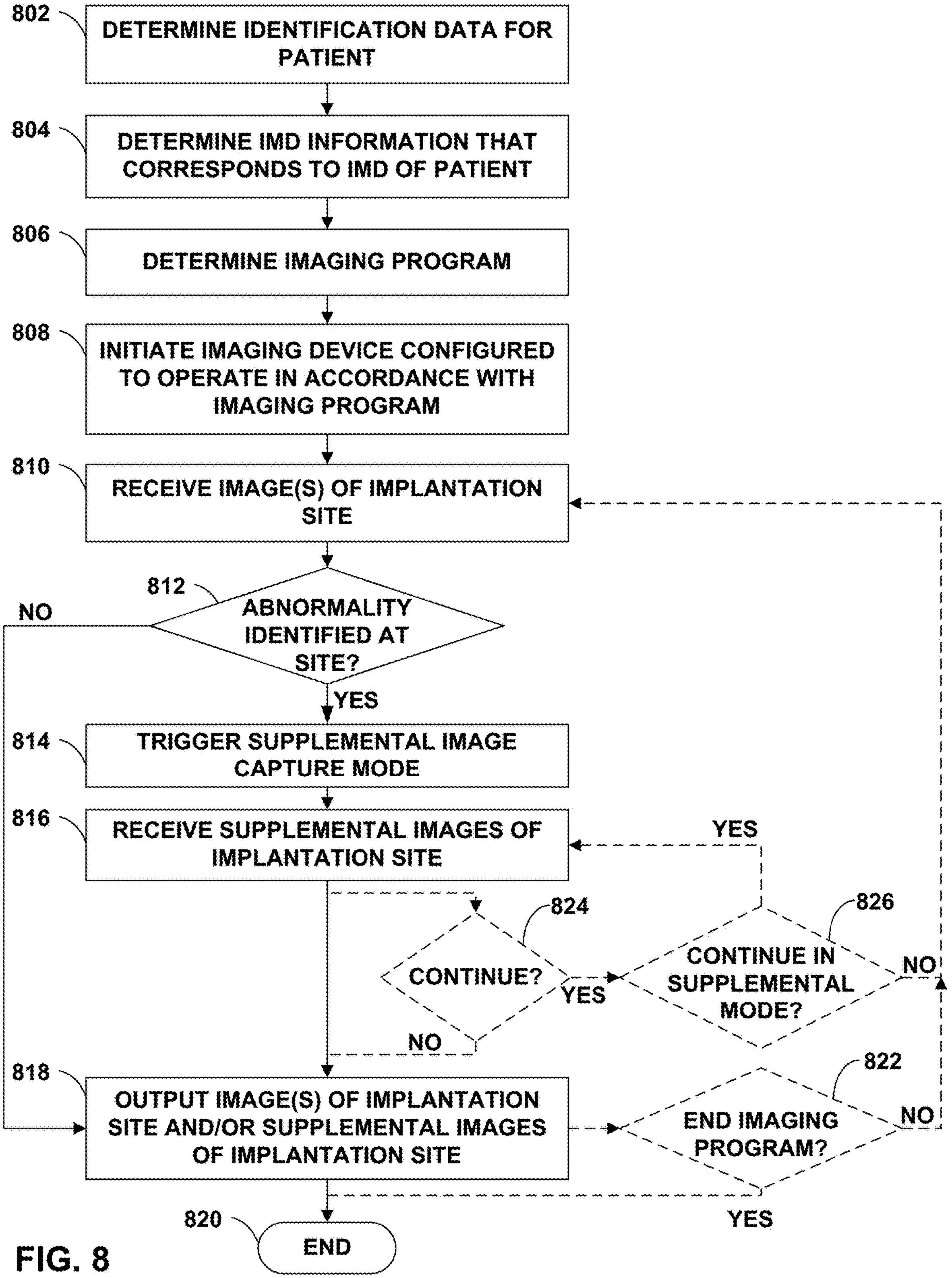

FIG. 8 is a flowchart illustrating an example method of utilizing imaging techniques, in accordance with one or more techniques of this disclosure.

Figure 9:
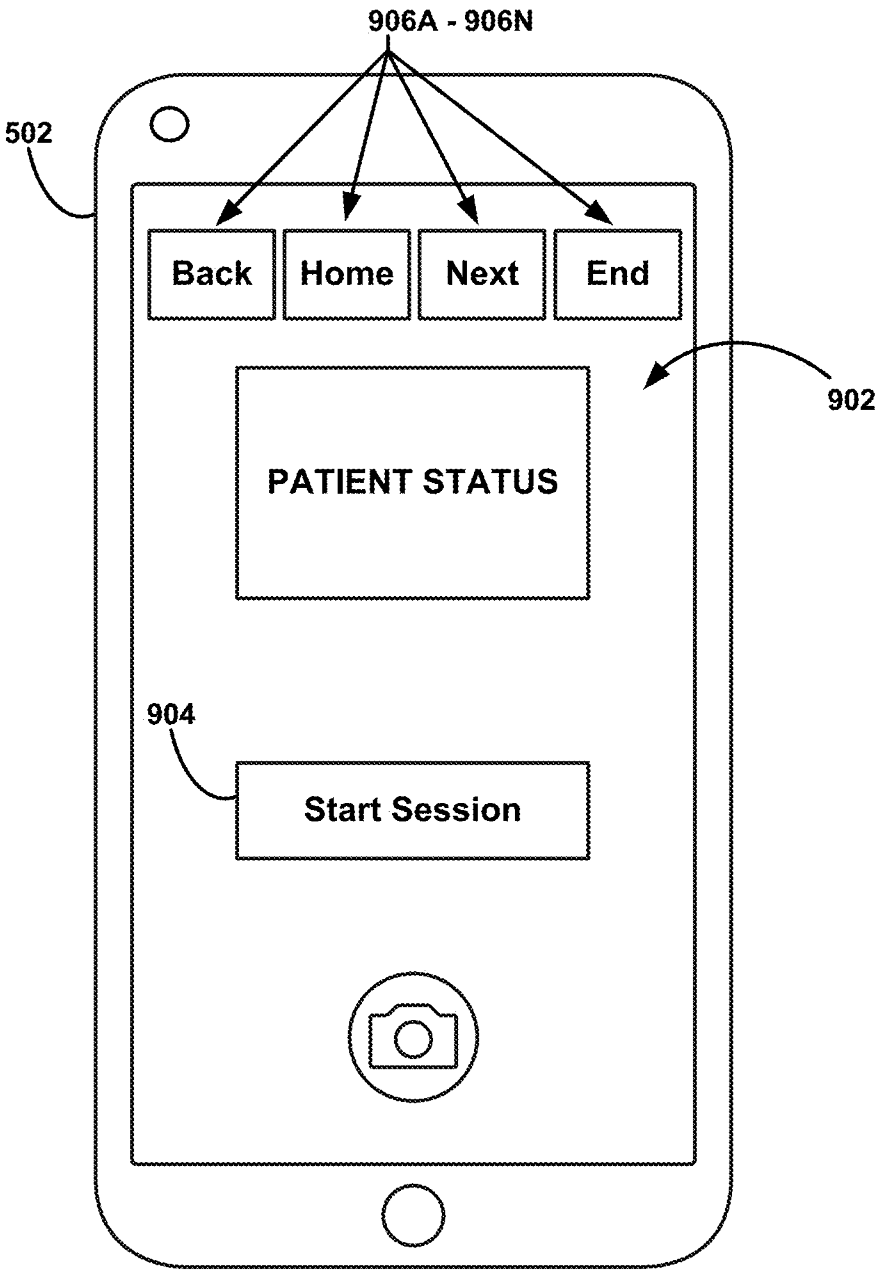

FIG. 9 is an UI visualization of an example patient status interface that presents upon user request of patient status interface illustrated in FIG. 7, in accordance with one or more techniques of this disclosure.

Figure 10:
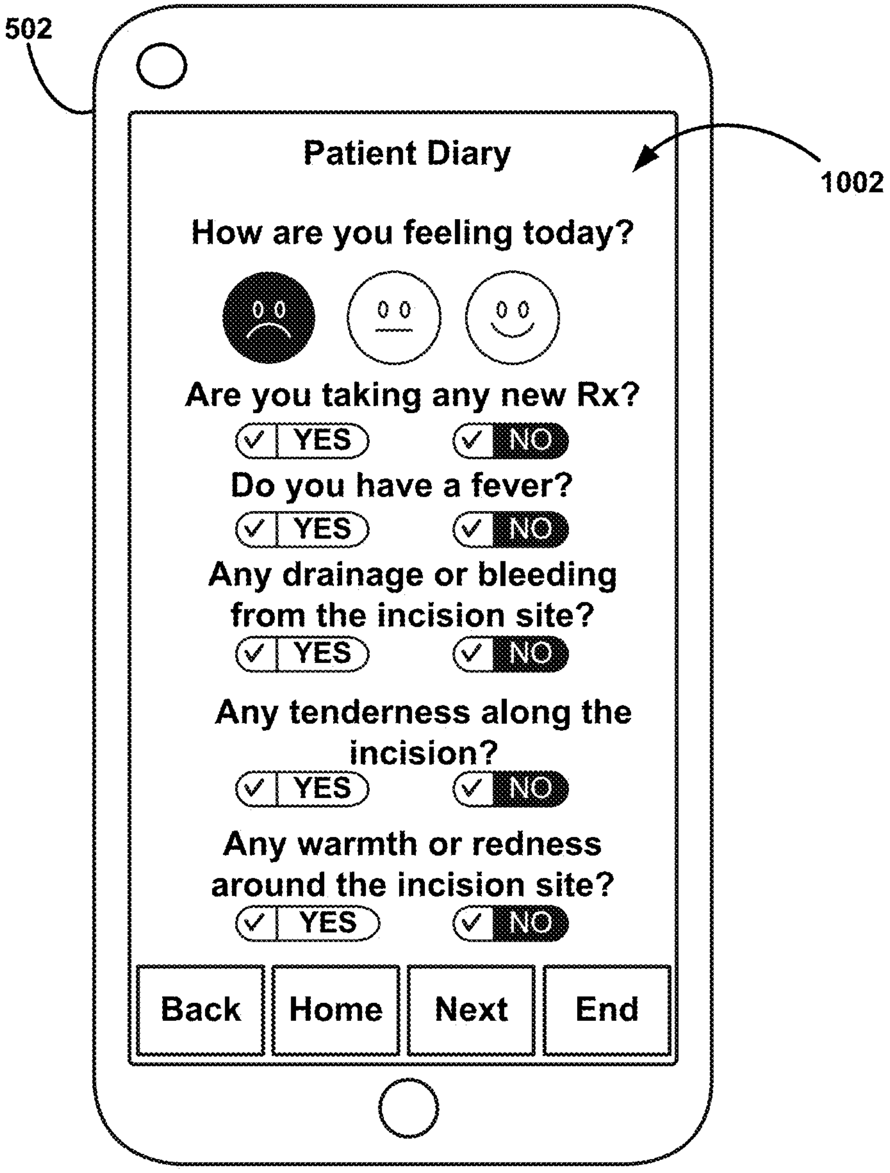

FIG. 10 is a UI visualization of an example patient status interface, in accordance with one or more techniques of this disclosure.

Figure 11:
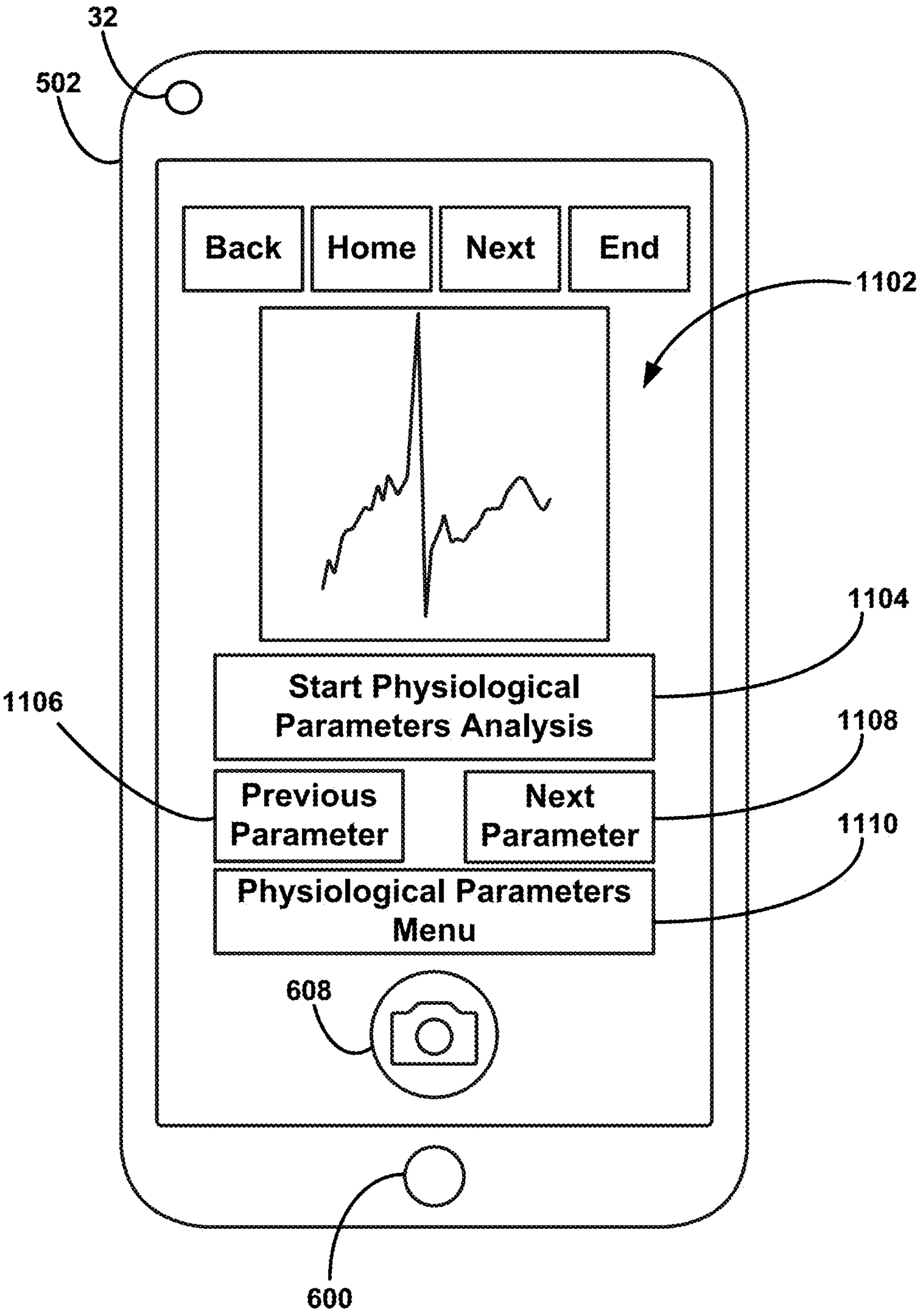

FIG. 11 is a UI visualization of an example physiological parameter check interface, in accordance with one or more techniques of this disclosure.

Figure 12:
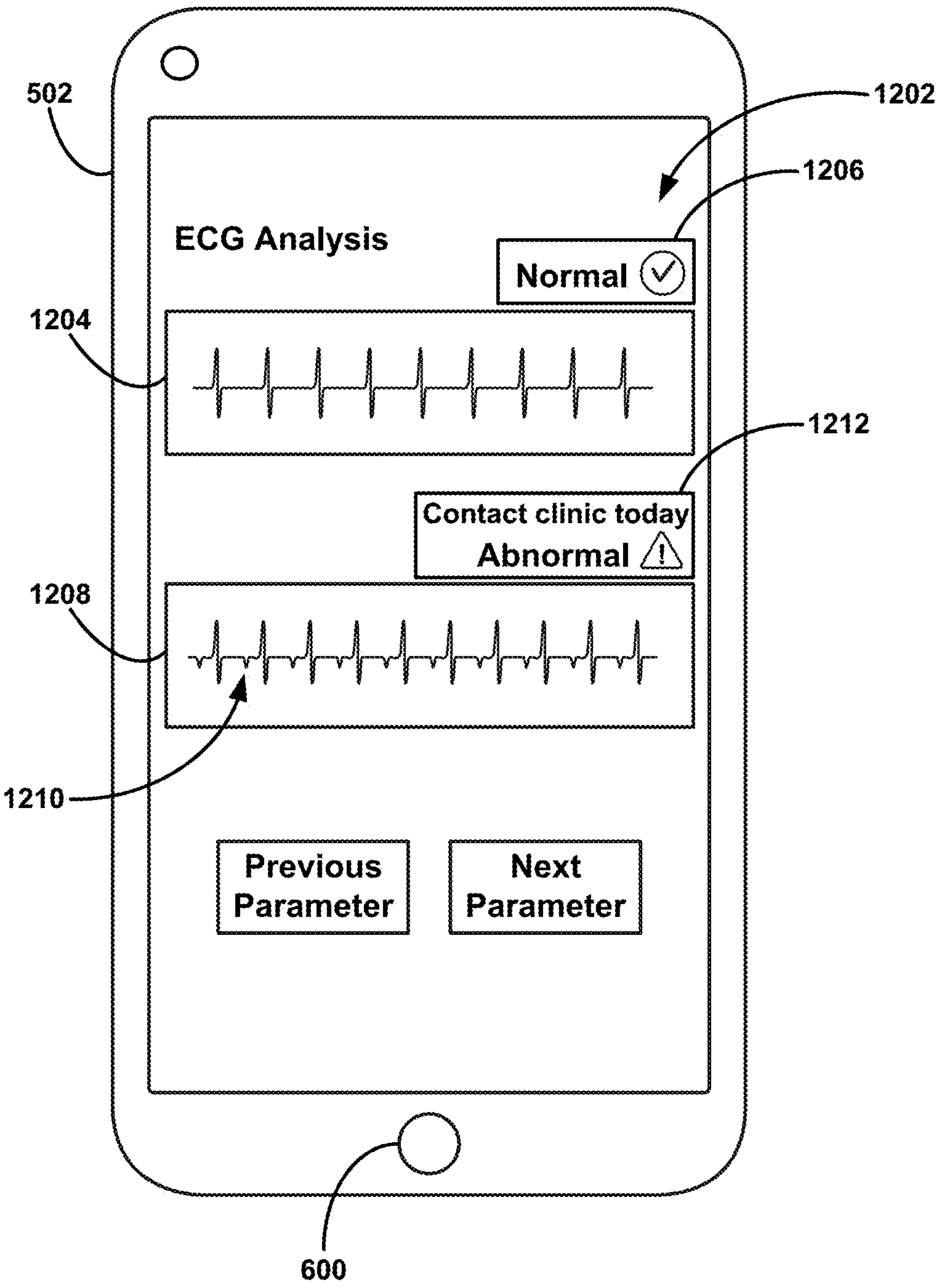

FIG. 12 is a UI visualization of an example physiological parameter check interface, in accordance with one or more techniques of this disclosure.

Figure 13:
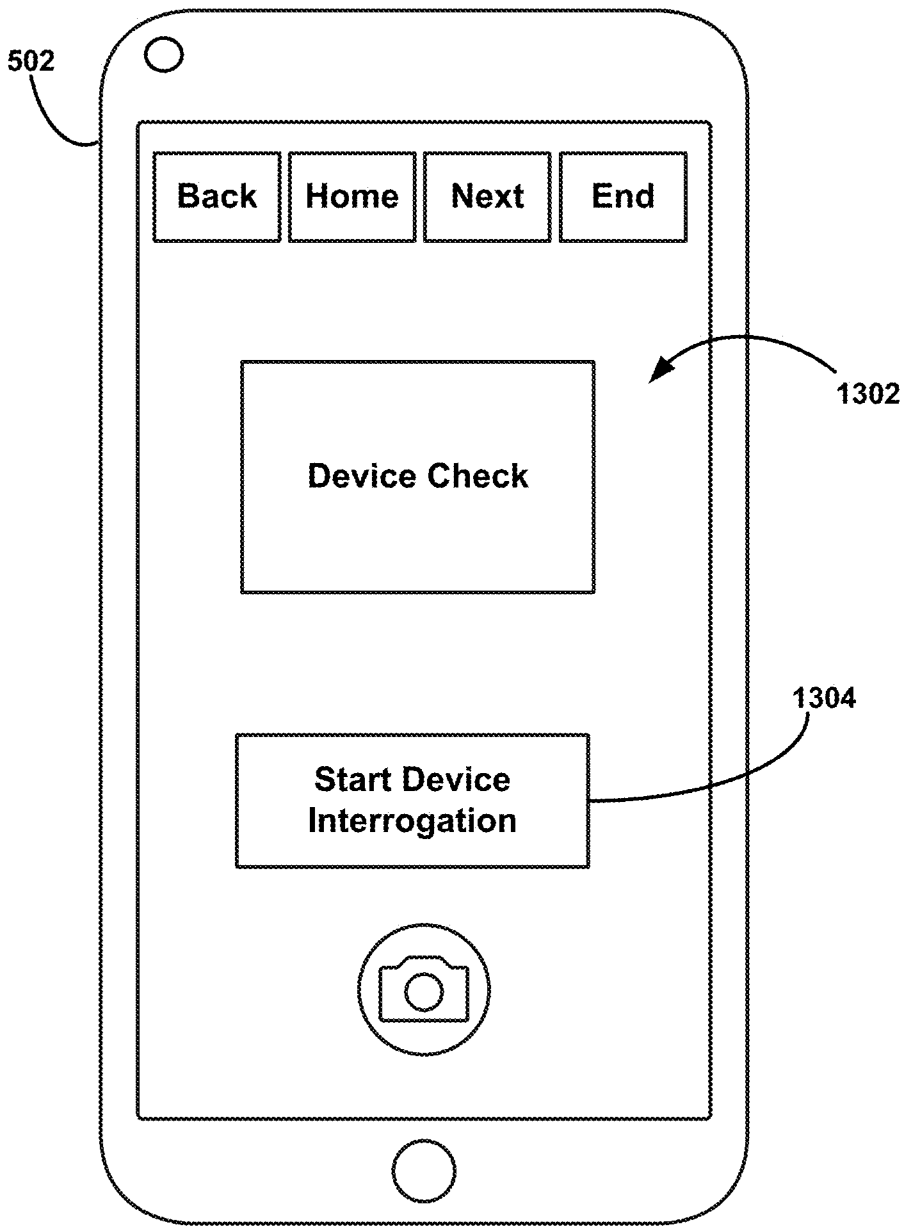

FIG. 13 is a UI visualization of an example device check interface, in accordance with one or more techniques of this disclosure.

Figure 14:
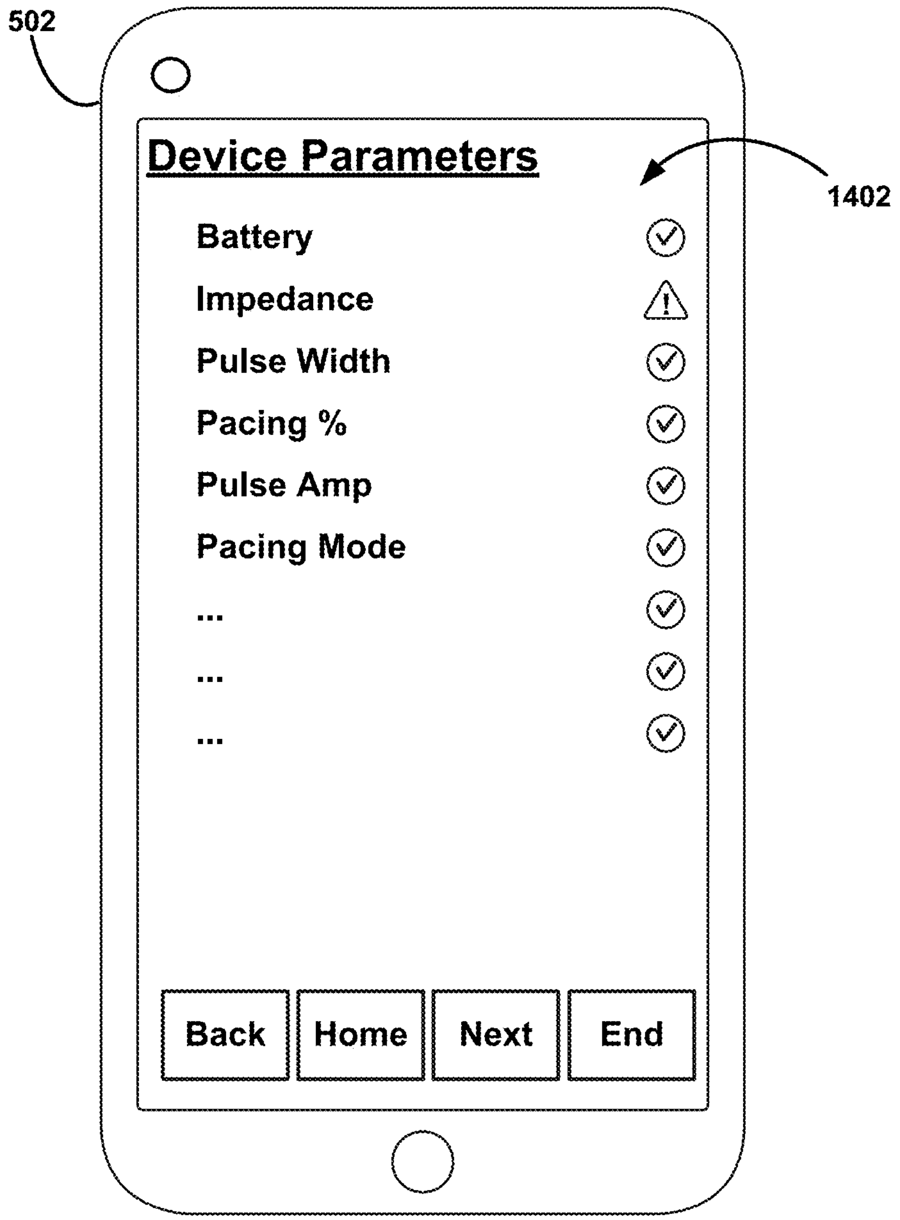

FIG. 14 is a UI visualization of an example device check interface, in accordance with one or more techniques of this disclosure.

Figure 15:
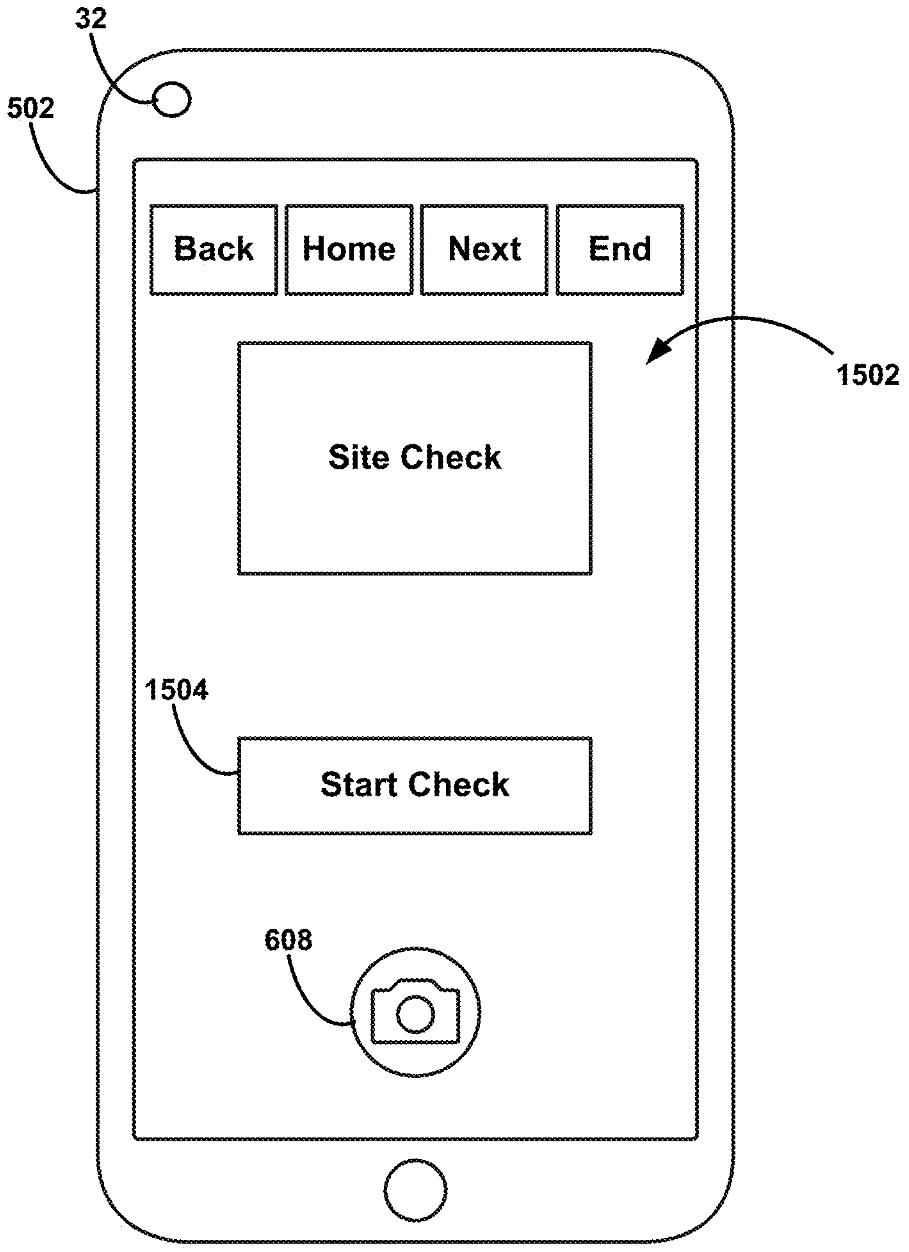

FIG. 15 is a UI visualization of an example site check interface, in accordance with one or more techniques of this disclosure.

Figure 16:
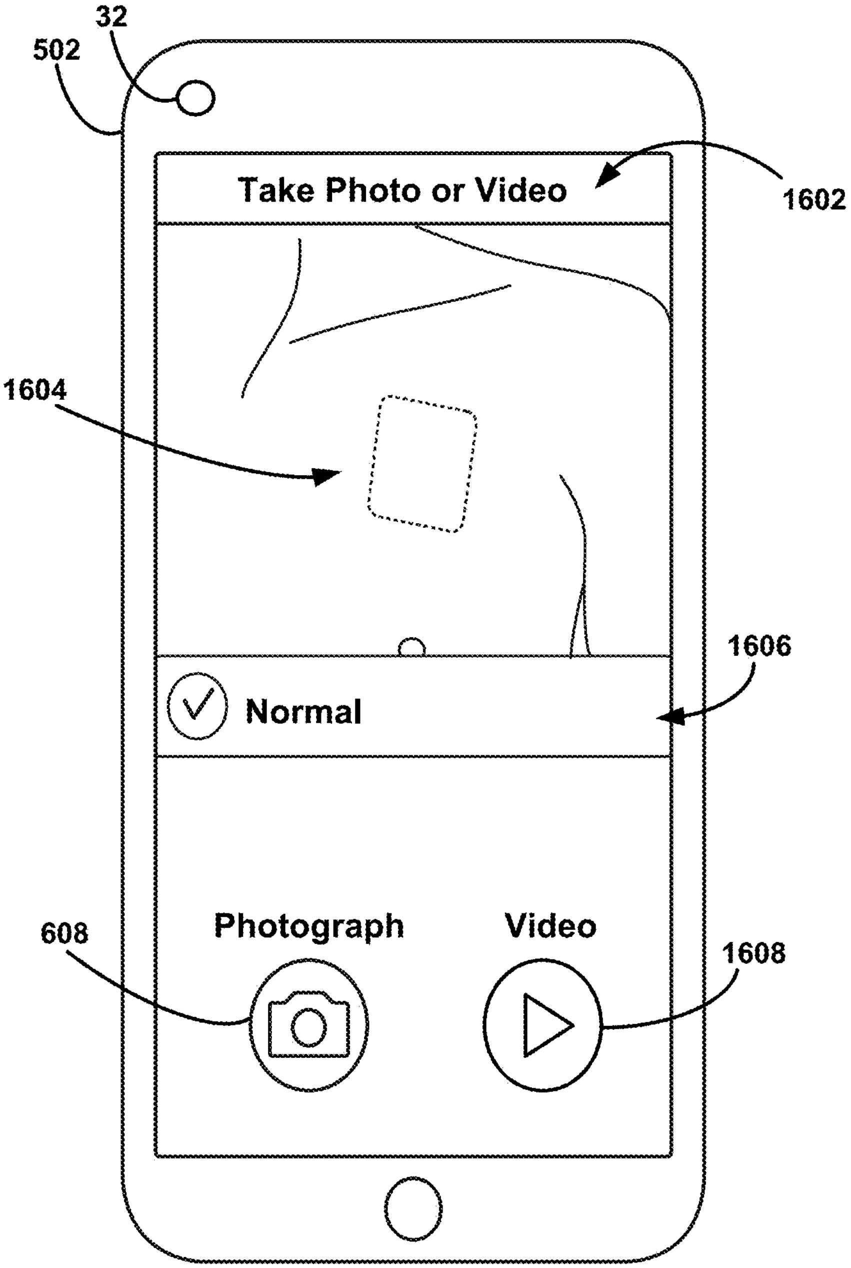

FIG. 16 is a UI visualization of an example site check interface, in accordance with one or more techniques of this disclosure.

Figure 17:
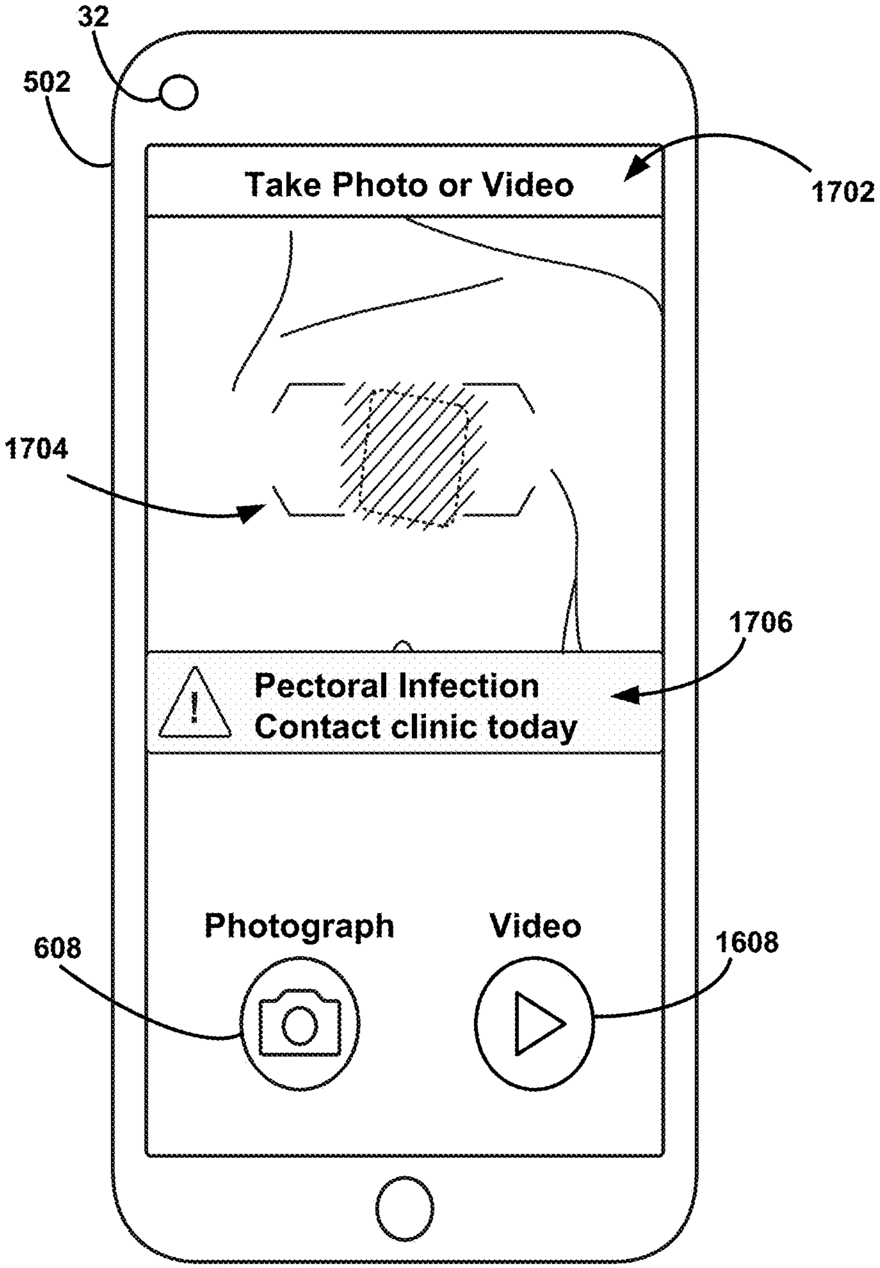

FIG. 17 is a UI visualization of an example site check interface, in accordance with one or more techniques of this disclosure.

Figure 18:
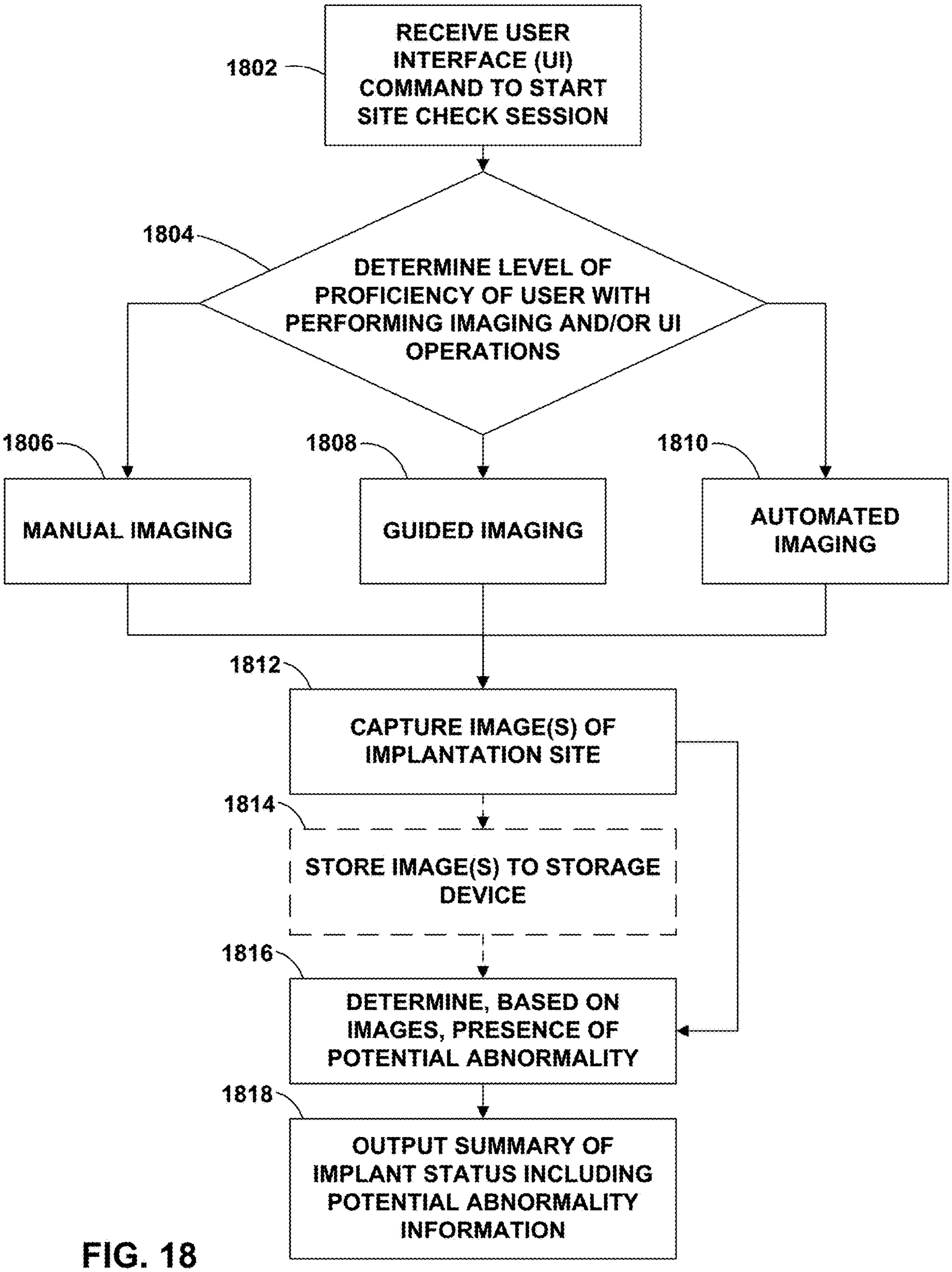

FIG. 18 is a flowchart illustrating an example method of utilizing imaging techniques pursuant to various proficiency levels, in accordance with one or more techniques of this disclosure.

Figure 19:
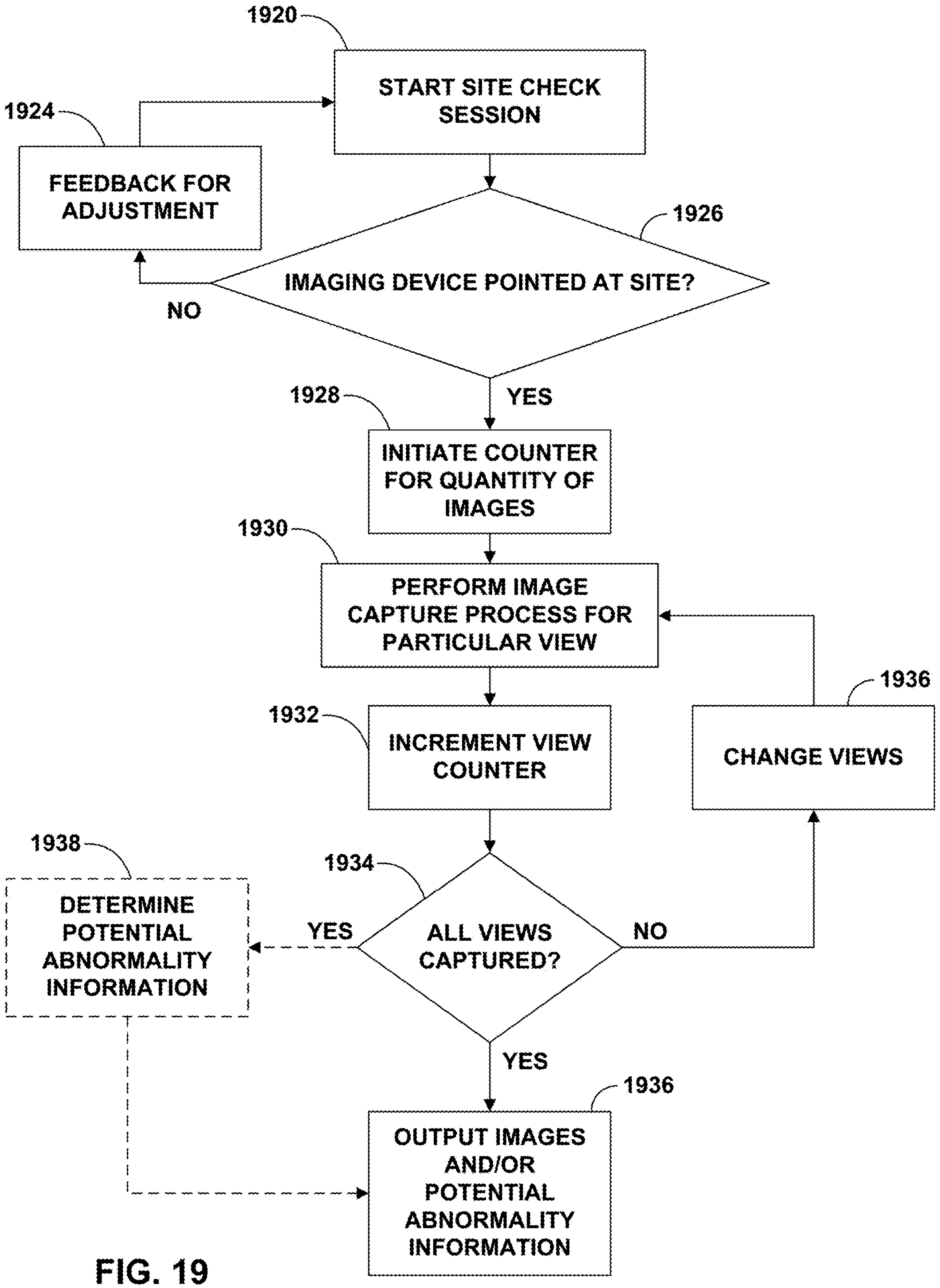

FIG. 19 is a flowchart illustrating an example method of performing a site-check process including an image capture process, in accordance with one or more techniques of this disclosure.

Figure 20:
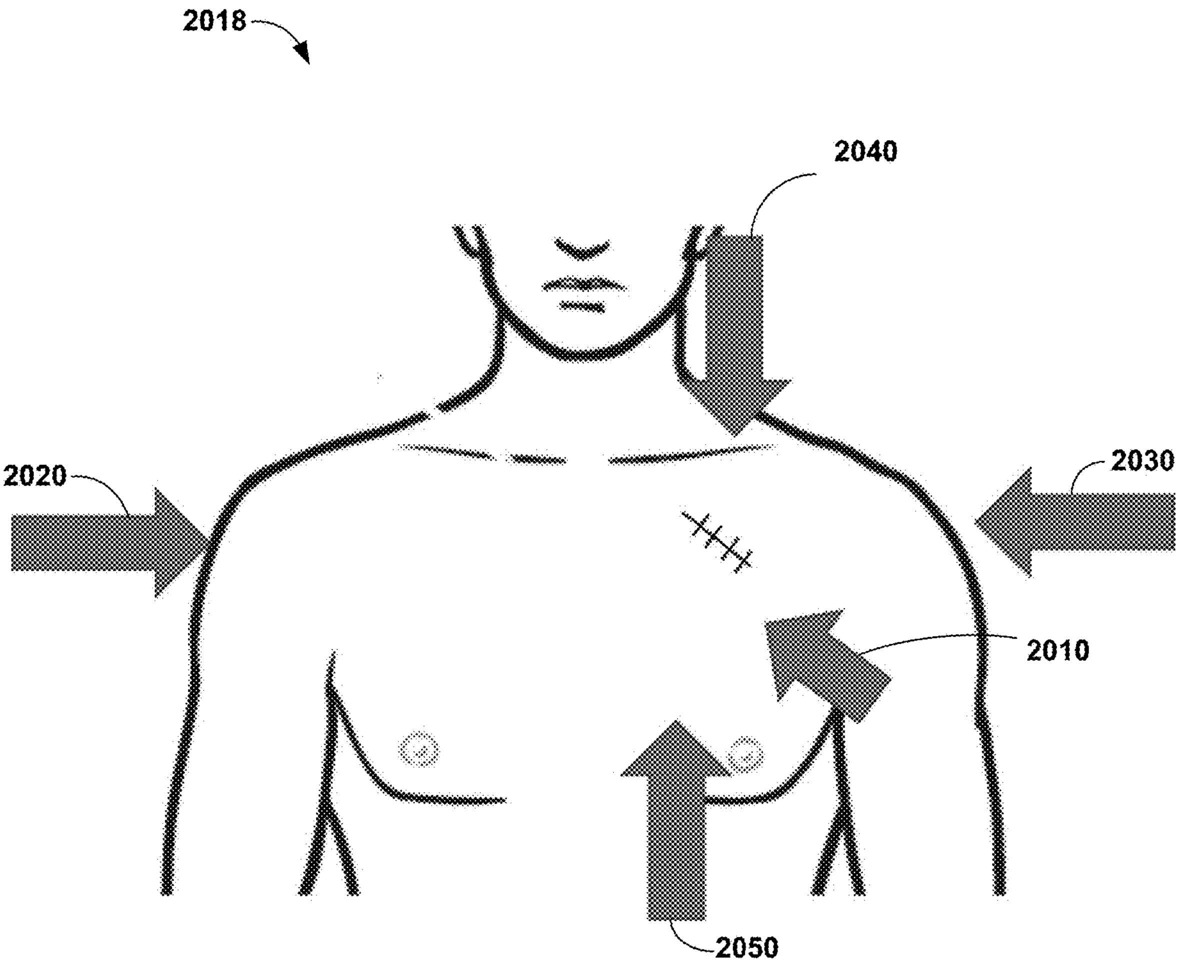

FIG. 20 is an example illustration of a plurality of perspective views of an example implantation site, in accordance with one or more techniques of this disclosure.

Figure 21:
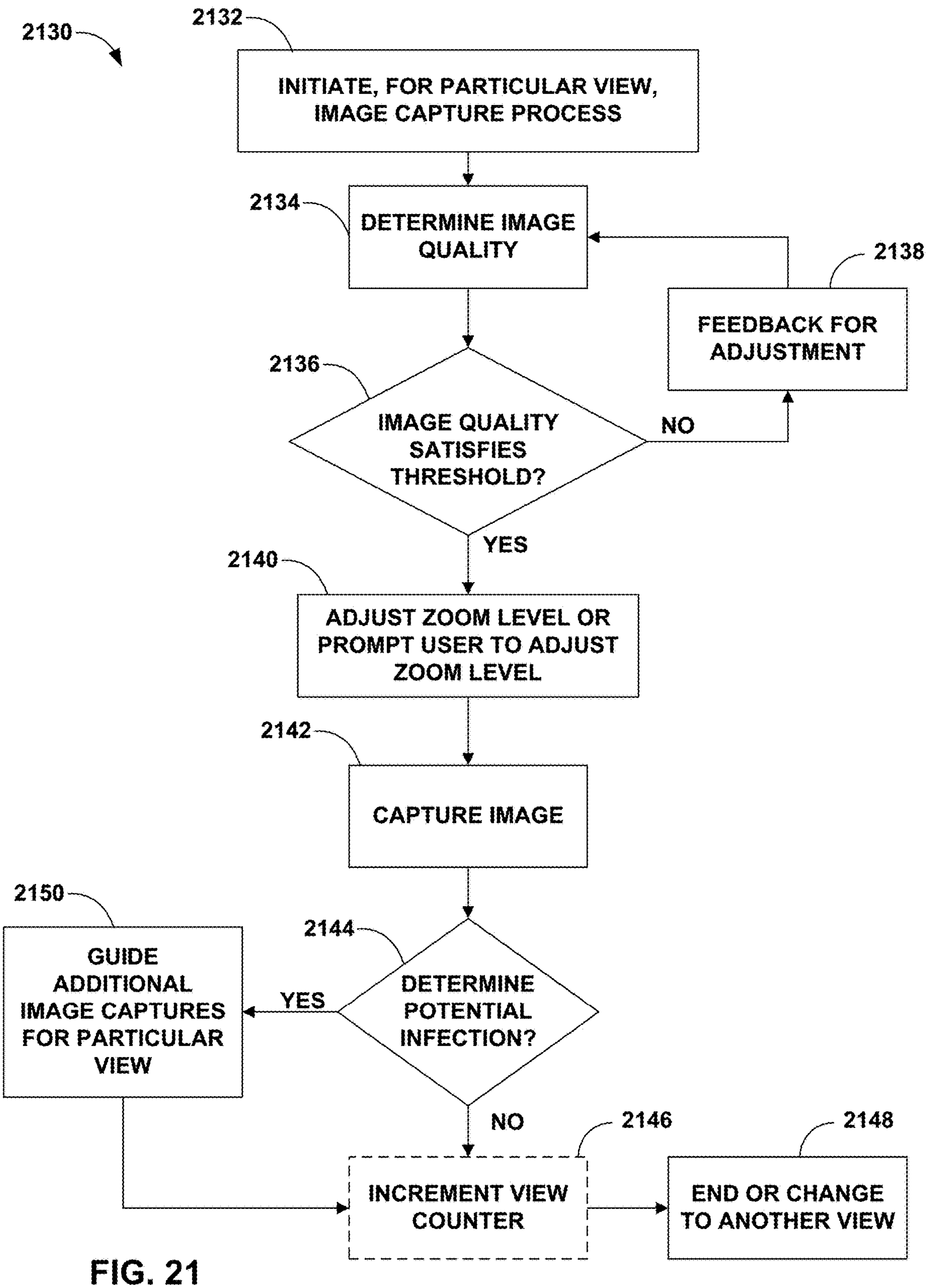

FIG. 21 is a flowchart illustrating an example method of performing an image capture process, such as the image capture process of FIG. 18, in accordance with one or more techniques of this disclosure.

Figure 22:
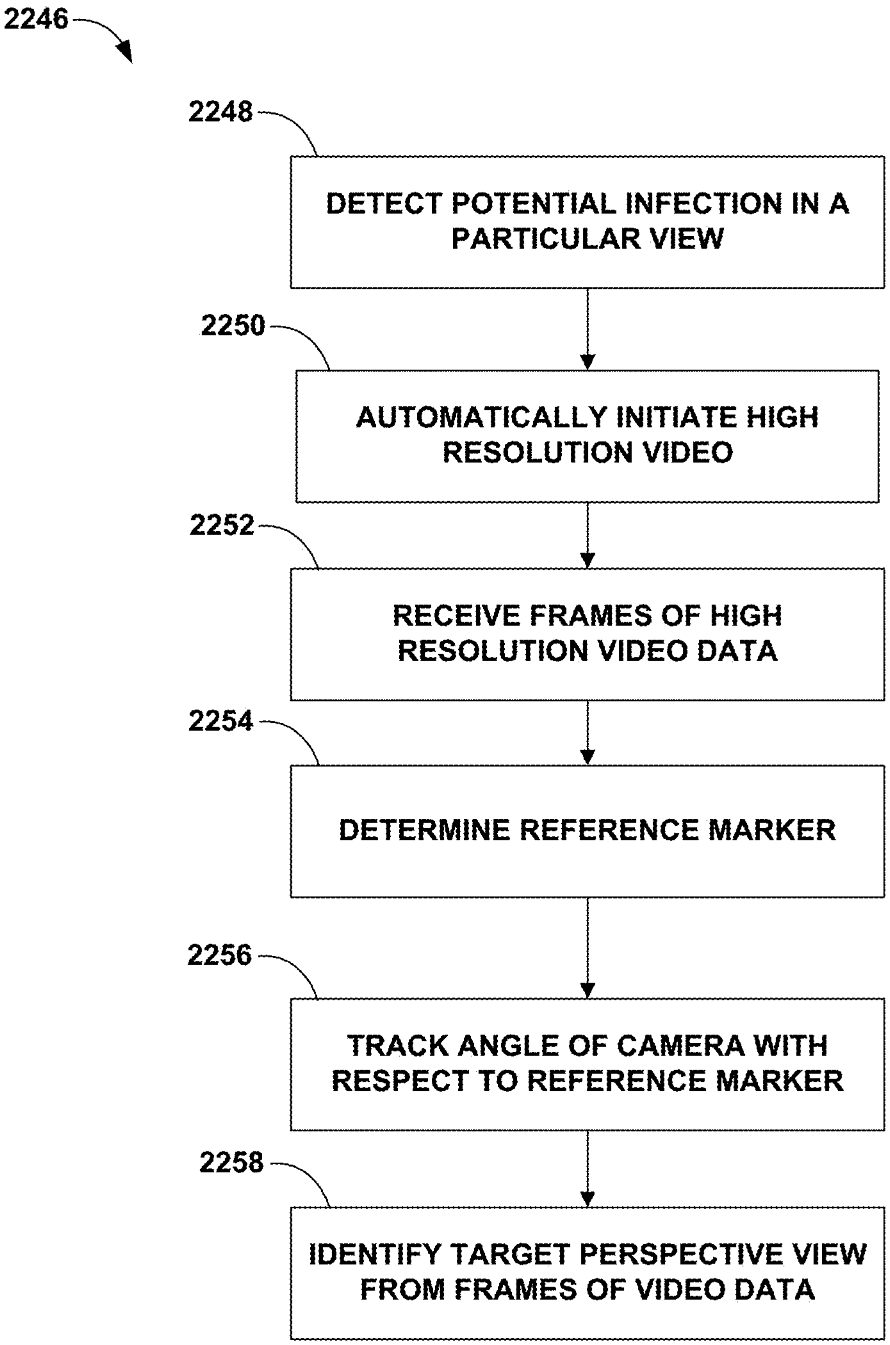

FIG. 22 is a flowchart illustrating an example method of utilizing imaging techniques, in accordance with one or more techniques of this disclosure.

Figure 23:
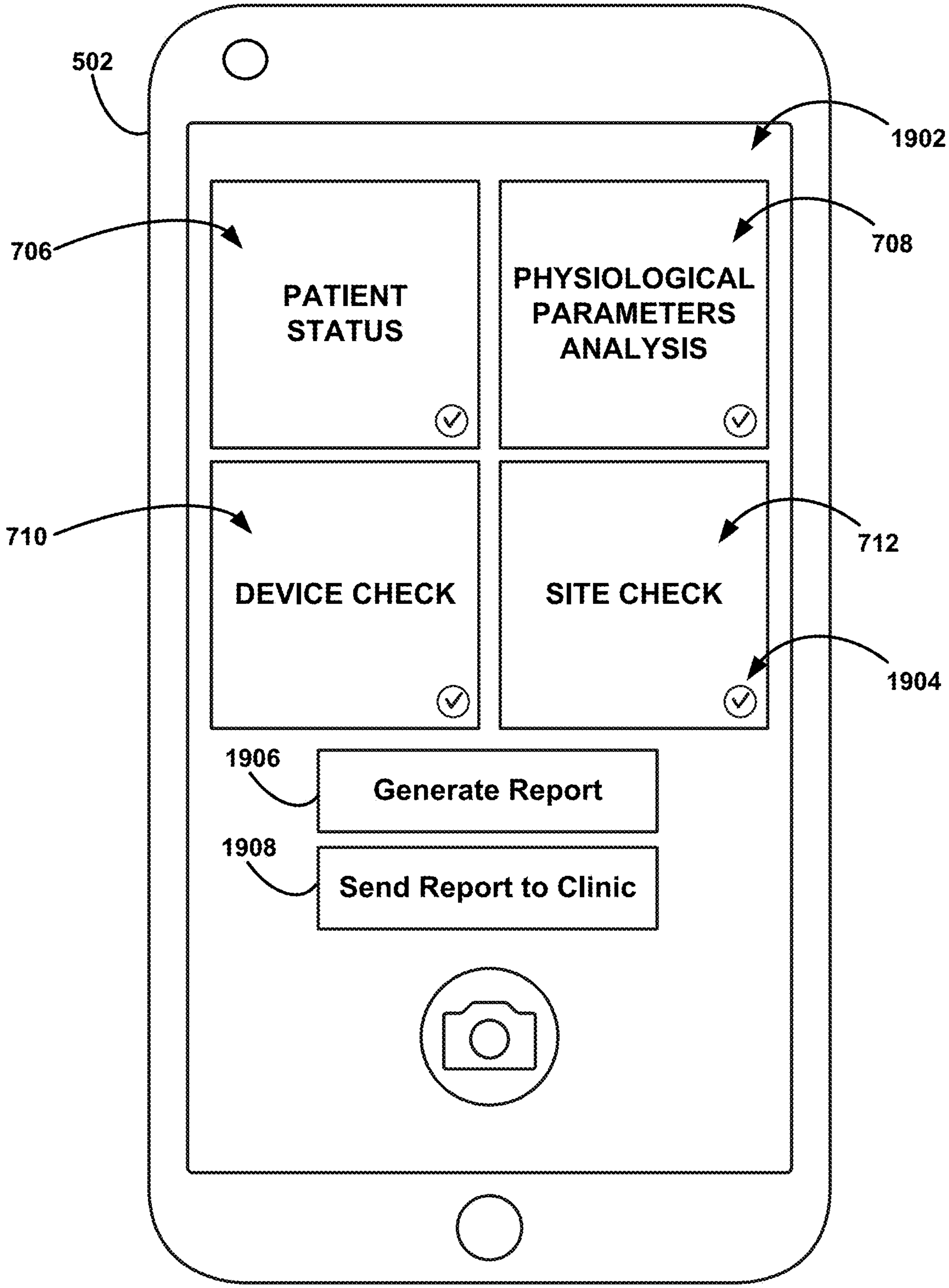

FIG. 23 is a UI visualization of an example complete check-in interface, in accordance with one or more techniques of this disclosure.

Figure 24:
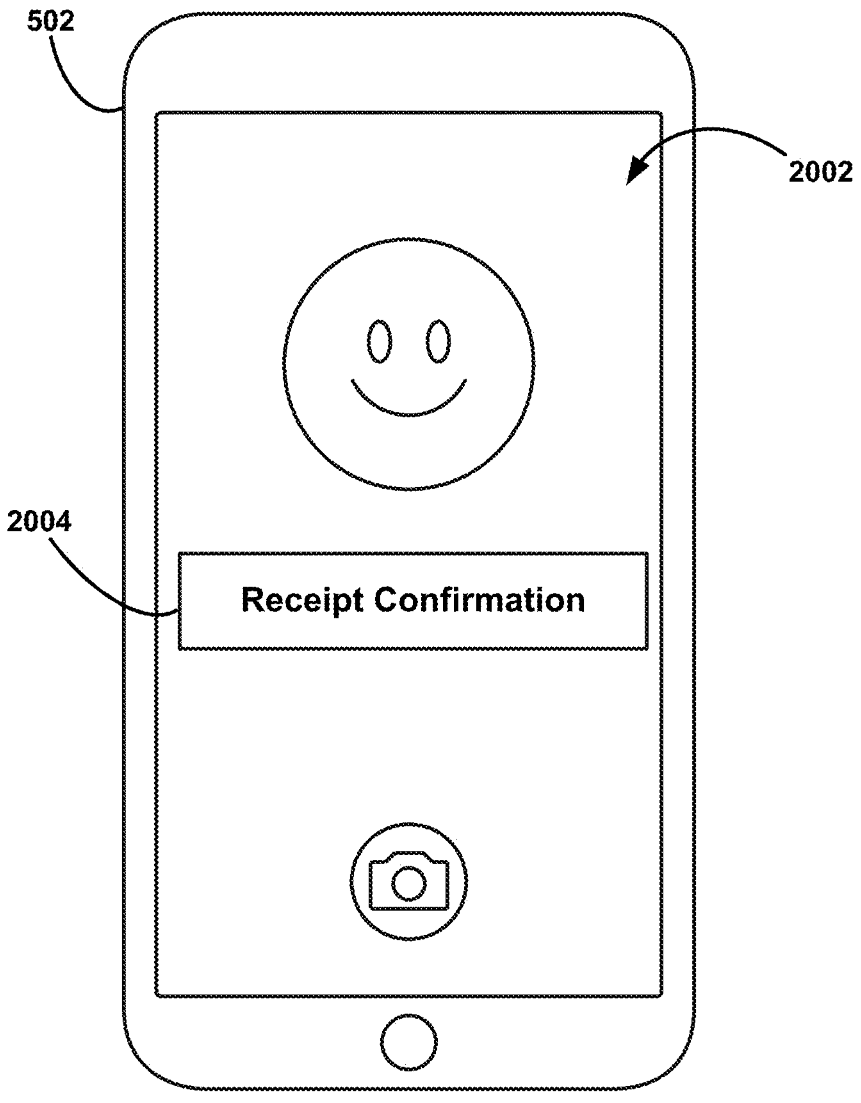

FIG. 24 is a UI visualization of an example complete check-in interface, in accordance with one or more techniques of this disclosure.

Figure 25:
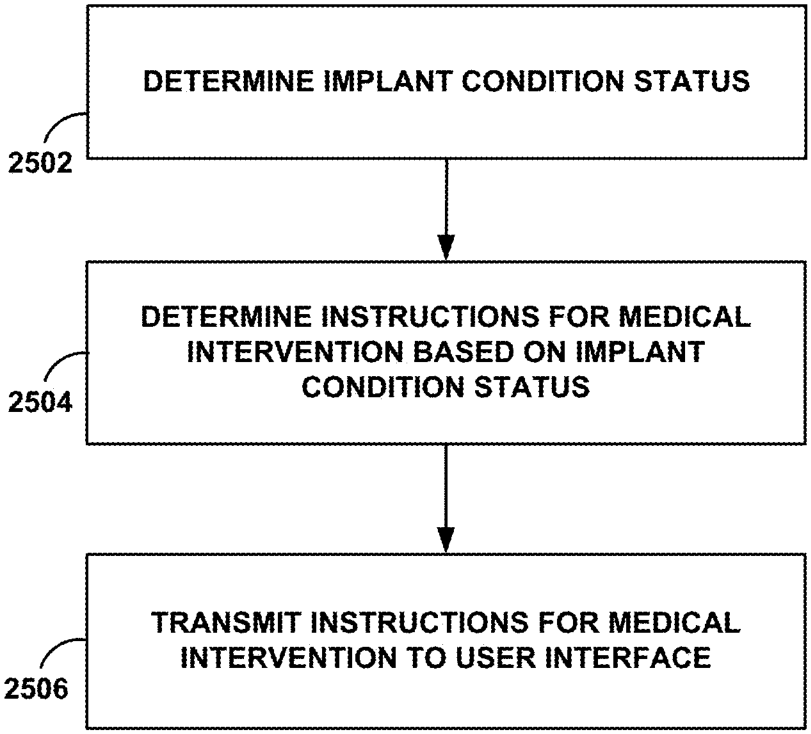

FIG. 25 is a flowchart illustrating an example method of determining instructions for medical intervention concerning an IMD patient, in accordance with one or more techniques of this disclosure.

Like reference characters denote like elements throughout the description and figures.

DETAILED DESCRIPTION

In 2019, over 1.5 million implantable medical device (IMD) implants were expected to be implanted in patients worldwide. Per Heart Rhythm Society (HRS) and European Heart Rhythm Association (EHRA) guidelines, each of those implants should have had an in-person follow-up within two to twelve weeks. Patient adherence with the post-implant visit improves mortality and patient outcome. Patient compliance with this visit, however, ranges from 55-80%. For 93-99% of these visits, patients present without abnormalities (e.g., infections). That is, many of these visits could be performed virtually.

This disclosure presents systems and methods for remote post-IMD monitoring for implantation site infections. Implantation infections are estimated to occur in about 0.5% of IMD implants and about 2% of IMD replacements. Early diagnosis of IMD infections can help drive effective antibiotic therapy or device removals to treat the infection. This is done in an in-hospital, post-op setting where the patients can be continuously monitored.

A post-discharge infection diagnosis typically follows when patients feel any infection-related symptoms, such as pain or fever. However, for the subset of asymptomatic patients with infection that are unable to self-report any implantation site abnormalities, there is a need for expert review. Since having all patients come-in for a physical infection review can be cumbersome for both patients and caregivers, there is a need for remote monitoring of implantation sites.

In general, this disclosure is directed to a browser interface or a mobile device app that can be operated via a variety of user-facing computing devices, including, but not limited to, a smartphone, tablet computer, mobile device, virtual reality (VR), augmented reality (AR), or mixed reality (MR) headset, etc. The computing device may execute a software app that causes the computing device to perform various functionalities described herein either locally, using the computing resources of the computing device, or via cloud computing, such as by transmitting captured data via a network interface to a backend system (e.g., a server system) that performs some or all of the analysis described herein. In addition, as described herein, some or all of the analysis may be performed, via edge computing, such as by transmitting captured data to an edge device (e.g., an IoT device or another computing device). In some examples, edge devices may include user-facing or client devices, such as smartphones, tablet computers, PDAs, and other mobile computing devices. In any case, a backend system may or may not include certain edge devices as part of the backend system. In one examples, a network may interface with one or more edge devices operating at the edge of the backend system, so as to form an intermediary between a computing device of a user and the various servers of a network. In such examples, a computing device may perform the various techniques of this disclosure by leveraging edge computing, cloud computing, or a combination thereof. An example combination of edge and cloud computing may include distributive computing or distributed computing systems. In any case, the computing device may perform the techniques of this disclosure in-app, in-tablet and/or in cloud environments.

In the cloud-based implementations of this disclosure, the mobile device app may receive various types of post-analysis data from the backend system, and present the data to the user, either in as-received form, or after performing some additional processing or formatting of the data locally.

The computing device executing the app (e.g., a virtual check-in process) may perform various functionalities described below, whether via local computing resources provided by the computing device, via cloud-based backend systems, or both. In some examples, the computing device may implement the app via a web browser. In some examples, the computing device may perform a device check. In such examples, the computing device may implement one or more interrogations of one or more medical devices (e.g., IMDs, CIEDs, etc.). In some instances, the computing device may receive medical device interrogation data over a network, directly from the one or more medical devices, from one or more edge devices, or any combination thereof. In such examples, the computing device may analyze medical device settings, parameters, and performance metrics.

In some examples, the computing device may perform a check of one or more surgical implantation sites (e.g., an implant wound site, an implant-removal site, etc.). In another example, the computing device may perform a check of one or more procedurally prepared implantation site. In an example, an insertable cardiac monitor may be inserted into a procedurally prepared implantation site during a patient visit under local anesthesia.

In some examples, the computing device may implement image processing with respect to an area indicative of an implantation site (e.g., a wound site, a surgical site, a procedurally prepare site, etc.). In some examples, the computing device may perform image processing using camera(s) of, or otherwise communicatively coupled to, the computing device to detect abnormalities, such as in wound healing and/or by determining potential infections at an implantation site. In some examples, the computing device may trigger various camera operating modes in order to obtain supplemental images of an implantation site. In one example, if computing device determines that a potential infection at an implantation site may be present, the computing device may initiate a supplemental capture mode (e.g., video capture mode, frame burst mode, motion photo mode, etc.), where the supplemental capture mode is configured to capture additional images of the implantation site. The computing device may use the additional images to determine the presence of an abnormality and in some instances, the likelihood of an abnormality being an actual abnormality. The computing device may further use images captured in a preceding image capture mode (e.g., an initial image capture mode) or a subsequent image capture mode (subsequent to the supplemental image capture mode) in order to obtain as many different images of the implantation site as is practical for the computing device. In an illustrative example, computing device may initially capture one or more images in a first image capture mode, and based on an abnormality determination, transition to a video capture mode (e.g., a high sample rate video mode), in order to capture an imaging sequence of the implantation site for analysis.

In some examples, the computing device may perform a physiologic check. In such examples, the computing device may enable monitoring and/or analysis of physiologic signals detected from the patient including electrocardiogram (ECG) signals, and other health signals that can be recorded (e.g. respiration, impedance, activity, pressure, etc.). In addition, the computing device may perform a patient status check. The app may implement an interactive logging, journaling, or diary function for the patient to respond to a few key questions regarding patient health information, medications, symptoms, physiological or anatomical metrics, or any relevant patient-reported information.

The tools of this disclosure may, in some examples, use artificial intelligence (AI) engines and/or machine learning (ML) models (e.g., image processing algorithms) in order to assess the health of the patient (e.g., the likelihood of an infection at the implantation site, an unintended rotation of the IMD, etc.). For the site-check process, computing devices executed the site-check process may invoke image recognition or image processing AI that leverages (e.g., is trained using) wound and infection libraries available from various sources. In addition, the computing device may deploy ML models to determine the presence of an infection at an implantation site. Similar to the AI engine, the computing device or another device may train a ML model on, for example, various abnormality libraries (e.g., training sets, wound and infection libraries). In addition, the computing device or another device may train the image processing algorithms on patient input, such as user answers to questionnaires, images of the implantation site, physiological parameters, as well as confirm when a potential infection is confirmed to be an actual infection. As such, the image processing algorithms may fine-tune the detection of an infection based on various correlations between particular data items. In one example, users may indicate particular pain levels when a particular shade of redness occurs around an implantation site. The image processing algorithms may correlate such data in order to provide a more robust detection of a potential abnormality. Likewise, particular ECG data or device parameters (e.g., temperature measurements) may correlate with implantation site infections, and computing devices or other devices may train the image processing algorithms on such data in order to achieve a high accuracy and confidence level of abnormality detections.

In addition, the AI engines may use cohort data to conduct individual checks. A cohort may include any number of cohorts, including a CIED cohort that includes CIED patients, an age cohort, a skin pigmentation cohort, an IMD type cohort, etc. or combinations thereof. In some examples, the ML models may be trained using cohort data to conduct individual checks. To perform ECG checks, the tools of this disclosure may use arrhythmia classification AI with a QRS model to classify normal rhythm and any underlying arrhythmias relative to the patient demographics and characteristics. It will be understood that a QRS model generally refers to a QRS complex that contains a combination of various graphical deflections included with a typical electrocardiogram (e.g., a Q wave, an R wave, an S wave, etc.). To perform device check functionalities of this disclosure, the app may leverage various communication hardware components of the computing device to interrogate the one or more medical devices (e.g., an IMD) to retrieve medical device parameters specific to the medical device family. The processing circuitry system may be configured to compare the retrieved parameters to the physician's earlier-provided settings as well as to comparable medical device families for deviation of normality/normalcy analysis.

The tools of this disclosure may also provide patient status check functionalities using an interactive session with the patient in which the patient provides elicited input to answer questions related to the patient's health and present condition. In various examples, the tools of this disclosure may enable the patient to enter information (e.g., condition information or results) via text entry, dropdown menu selection from prepopulated responses, and/or radio buttons as shown in one or more of the accompanying drawings. In some non-limiting examples, the tools of this disclosure may output questions, to elicit patient responses by which the patient could enter information such as medications, doses thereof, as well as other prompted information.

At the completion of the session, the tools of this disclosure may mark the results on a UI provided via the mobile device app, with date and time stamping. The tools of this disclosure may provide the patient with the capability to generate a report (e.g., as a portable document format (PDF) or in various other formats) for the records of the patient, to email or otherwise transfer the report or select contents of the report to family members or to a doctor (e.g., via a File Transfer Protocol (FTP)), etc. As discussed herein, the UI may, in some instances, provide specific information regarding the site-check aspects of this disclosure and in such instances, a separate UI may be employed with respect to the other UI aspects of this disclosure.

The app of this disclosure may, in some non-limiting examples, provide the patient the capability to save the results locally to the computing device (e.g., a smartphone or tablet computer) for future comparison, reference, or use as a standalone file. In some instances, the computing device may store the results locally to the computing device for use as a retrievable session within the app or other app, or as part of a health kit implemented on the computing device. The app of this disclosure may, in some non-limiting examples, push the report to a proprietary network (e.g., via an online portal). By pushing the report or other data in this way, the tools of this disclosure enable the HCP to review the patient's health information and enter data into an electronic medical records (EMR) database or repository. The tools of this disclosure may generate a confirmation of receipt by the HCP based on various criteria (and in some examples, an indication of whether the report was reviewed by the HCP), and provide this communication to the patient via communication to the mobile device or other patient-accessible computing modality. In some examples, the computing device may be configured to receive an indication as to whether the report was reviewed by the HCP. In such examples, the computing device may be configured to provide, based at least in part on the indication, a user with a status of the report (e.g., HCP reviewed, review in-progress, etc.).

If the tools of this disclosure determine that any one check or any combination of checks described above yielded an abnormal result (or abnormal outside an acceptable margin of normal), the tools of this disclosure may use the mobile device app to output a prompt to the patient. In some examples, the prompt may indicate the abnormality, such as an indication of a potential infection at one or more implantation sites, where the implantation site(s) may include one or more of an implantation site of an IMD, a battery powered component of the IMD, and/or associated devices of the IMD. In some examples, the prompt may include a recommendation or instruction to schedule a follow-up visit with the HCP.

In some examples, the tools of this disclosure may store session information and results of previous checks (e.g., locally at the computing device, to a cloud storage resource, or to both). The computing device may do this in order to assist the patient and/or the HCP in tracking a progress or changes with respect to the patient's wound recovery, the functioning of the medical device, etc. In some examples, the tools of this disclosure may implement a limited date counter with respect to the app in order to deter or prevent the patient from continually using the app after the follow-up time window has expired. Aspects of this disclosure enable bidirectional communication, e.g. to loop in the physician, who may communicate with various messages, such as "call my office," etc.

As would be appreciated by one of skill in the art, the remote medical device monitoring, as disclosed herein, represents a significant technological advance over prior implementations. Specifically, the disclosed techniques can determine potential infections at a first confidence level using a first image capture mode and confirm using a supplemental image capture mode, resulting in an increased efficiency in assessing the status of an implantation site, where the supplemental image capture mode may be used sparingly in order to conserve processing, battery, and memory resources. Further, the disclosed techniques can yield health benefits by dynamically determining the presence of abnormalities by using specific tools that are deployed and implemented at particular moments in order to achieve the highest accuracy of an abnormality detection. A user may also be presented with the relevant control mechanisms that allow the user to intuitively operate the UI in order to capture the correct images and the correct number of images that will be used to achieve the highest accuracy of an abnormality detection. As such, the examples described herein represent significant improvements in this computer-related technology.

Additional examples disclosed herein also represent improvements in computer-related technology. For example, the camera system may use reference markers, such as a reference marker visible or otherwise invisible to a user, in order to track angles of the camera, such that particular perspective views may be obtained in a consistent and reliable manner. Additionally, the monitoring system disclosed herein may, in some examples, be native to other software applications, and thus, the tiles may be displayed using similar UI/UX elements. Other example improvements include the ability to call external sources of information to provide a greater relevance and complexity to a check-in report and in some examples, the ability to call APIs (e.g., language translation APIs, machine learning APIs) to perform additional work within the monitoring system. In one example, a cloud-deployed API may serve as the accessible endpoint for an ML model. In addition, various ML models or AI engines may be deployed as so-called light versions that are configured to operate efficiently on devices with significantly limited resources (e.g., mobile devices, tablets, etc.).

The ideas disclosed herein exist within the realm of computer-related technology. For example, the display of information in a UI where the relevant data does not necessarily reside in a storage device locally coupled to the relevant display device would be virtually impossible to replicate outside the realm of computer-related technology. In a non-limiting example, the imaging programs AI/ML tools may be simultaneously or dynamically obtained from disparate systems and simultaneously or dynamically presented in a UI. Additionally, the monitoring system may intuitively present the data on the proper display, through the proper medium, and/or at the proper moment (e.g., on a static schedule or dynamically-updating schedule). In addition, the techniques of this disclosure provide abnormality determination techniques that may utilize, in some examples, non-visual sensors, such as thermal imaging with cameras in order to detect temperature changes at an implantation site. In addition, various data analysis techniques are described that utilize a particular examples of synthesizing various data items (e.g., images of an implantation site, device status information, etc.), where the information sources may be optimized to provide specific data relative to the specific technical problem of patient monitoring post-implant. That is, the synthesis of data, in some examples, provides a robust algorithm for identifying abnormalities, notwithstanding the algorithms described for obtaining and analyzing specific sections of data, such as image data, for potential abnormalities.

Additionally, it has been noted that design of computer UIs "that are useable and easily learned by humans is a non-trivial problem for software developers." (Dillon, A. (2003) User Interface Design. MacMillan Encyclopedia of Cognitive Science, Vol. 4, London: MacMillan, 453-458.). The various examples of interactive and dynamic UIs of the present disclosure are the result of significant research, development, improvement, iteration, and testing and in some examples, provide a particular manner of obtaining information, summarizing, and presenting information in electronic devices. This non-trivial development has resulted in the UIs described herein, which are likely to provide significant cognitive and ergonomic efficiencies and advantages over previous systems going forward. The interactive and dynamic UIs include improved human-computer interactions that may provide, for a user, reduced mental workloads/burdens, improved decision-making, reduced work stress, etc. For example, a UI with the interactive UIs described herein may provide an optimized presentation of patient-specific information from various sources and may enable a user to more quickly access, navigate, assess, and utilize such information than with previous systems which can be slow, complex and/or difficult to learn, particularly to novice users. Thus, the presentation of concise and compact information on a particular UI that corresponds to a particular patient makes for efficient use of the information available and optimal use of the medical devices and virtual check-up functionalities of this disclosure.

FIG. 1 illustrates the environment of an example monitoring and/or check-in system 100 in conjunction with a patient 4. In some examples, system 100 may implement the various patient and medical device monitoring and abnormality detection techniques disclosed herein. System 100 includes one or more medical device(s) 6 and one or more computing device(s) 2. While medical device(s) 6, in some instances, include an IMD, as shown in FIG. 1, the techniques of this disclosure are not so limited. For illustrative purposes, however, medical device(s) 6 may in some instances be referred to herein simply as IMD 6 or IMD(s) 6.

Computing device(s) 2 may be a computing device with a display viewable by a user. The user, may be a physician technician, surgeon, electrophysiologist, clinician (e.g., implanting clinician), or patient 4. Patient 4 ordinarily, but not necessarily, will be a human. For example, patient 4 may be an animal needing ongoing monitoring for various health conditions (e.g., cardiac conditions, spinal cord conditions, etc.). In such instances, a human caregiver may operate aspects of the disclosed technology that utilize user input that may not be feasibly available from an animal patient 4.

Computing device(s) 2 may be referred to in some instances herein as a plurality of "computing device(s) 2," while in other instances may be referred to simply as "computing device 2," where appropriate. System 100 may be implemented in any setting where at least one of computing device(s) 2 may interface with and/or monitor at least one of medical device(s) 6 and/or an implantation site of medical device(s) 6, in accordance with one or more techniques of this disclosure. Computing device(s) 2 may interface with and/or monitor medical device(s) 6, for example, by imaging the implantation site of the medical device(s) 6, in accordance with one or more techniques of this disclosure.

In some examples, computing device(s) 2 may include one or more of a cellular phone, a "smartphone," a satellite phone, a notebook computer, a tablet computer, a wearable device, a computer workstation, one or more servers, a personal digital assistant, a handheld computing device, virtual reality headsets, wireless access points, motion or presence sensor devices, or any other computing device that may run an application that enables the computing device to interact with medical device(s) 6 or interact with another computing device that is, in turn, configured to interact with medical device(s) 6.

At least one of computing device(s) 2 may be configured to communicate with medical device(s) 6 and, optionally, other ones of computing device(s) 2, via wired or wireless communication. Computing device(s) 2, for example, may communicate via near-field communication (NFC) technologies (e.g., inductive coupling, NFC or other communication technologies operable at ranges less than 10-20 cm) and/or far-field communication technologies (e.g., Radio Frequency (RF) telemetry according to the 802.11, Bluetooth® specification sets, or other communication technologies operable at ranges greater than NFC technologies). In some examples, computing device(s) 2 may include an interface for providing input to edge device(s) 12, network 10, and/or medical device(s) 6. For example, computing device(s) 2 may include a user input mechanism, such as a touchscreen, that allows a user to store images or imaging sequences to a database. In such examples, one of edge device(s) 12 may manage the database, which in some instances, computing device(s) 2 may access via network 10 in order to perform one or more of the various techniques of this disclosure.

Computing device(s) 2 may include a user interface (UI) 22 In some examples, UI 22 may be a graphical UI (GUI), an interactive UI, etc. In some examples, UI 22 may further include a command line interface. In some examples, computing device(s) 2 and/or edge device(s) 12 may include a display system (not shown). In such examples, the display system may comprise system software for generating UI data to be presented for display and/or interaction. In some examples, processing circuitry, such as that of computing device(s) 2, may receive UI data from another device, such as from one of edge device(s) 12 or server(s) 94 (FIG. 3), that computing device(s) 2 may use to generate UI data to be presented for display and/or interaction.

Computing device(s) 2 may be configured to receive, via UI 22, input from the user. UI 22 may include, for example, a keypad and a display, which may for example, be a liquid crystal display (LCD) or light emitting diode (LED) display. In some examples, a display of computing device(s) 2 may include a touch screen display, and a user may interact with computing device(s) 2 via the display. It should be noted that the user may also interact with computing device(s) 2 remotely via a network computing device.

UI 22 may further include, in some examples, a keypad. In some examples, UI 22 may include together the keypad with the display. The keypad may take the form of an alphanumeric keypad or a reduced set of keys associated with particular functions. Computing device(s) 2 may additionally or alternatively include a peripheral pointing device, such as a mouse, via which the user may interact with UI 22. In some instances, UI 22 may include a UI that utilizes virtual reality (VR), augmented reality (AR), or mixed reality (MR) UIs, such as those that may be implemented via a VR, AR, or MR headset.

In some examples, computing device(s) 2 may include an imaging device, such as a camera 32. Camera 32 may be a digital camera built into computing device(s) 2. In some examples, camera 32 may be separate from computing device(s) 2. In such examples, camera 32 may communicate imaging data to computing device(s) 2 and/or other computing device (e.g., edge device(s) 2). In some examples, computing device(s) 2 may include a charge-coupled device (CCD) chip. The CCD chip may be configured to operate in a spectral response analysis mode using flash as an excitation (e.g., white light) light source. In such examples, computing device(s) 2 may employ a CCD chip in order to analyze an image of an implantation site or an imaging sequence of the implantation site. In one example, computing device(s) 2 may employ a CCD chip to provide separate color filtering analysis in different light wavelength to better detect redness and swelling in different skin tones. That is, computing device(s) 2 may perform a color filtering on the images or imaging sequence in order to identify an abnormality from a set of images and/or from an imaging sequence. In another example, computing device(s) 2 may perform a color filtering on an image in order to determine to automatically trigger a supplemental image capture mode to capture supplemental images (e.g., an imaging sequence).

In an illustrative example, computing device(s) 2 may use camera 32 to image an implantation site of patient 4. In such examples, a storage device 24 (FIG. 2) of computing device 2 may store image data (e.g., still-images, video data, etc.). In such instances, processing circuitry, such as processing circuitry 20 (FIG. 2) of computing device 2 and/or processing circuitry 64 (FIG. 3) of edge device(s) 12, may be in communication with storage device 24.

In some examples, processing circuitry, e.g., processing circuitry 20 (FIG. 2) of computing device(s) 2, processing circuitry 64 of edge device(s) 12 (FIG. 3), processing circuitry 98 of server(s) 94 (FIG. 3), or processing circuitry 40 of medical device(s) 17, may determine identification data for patient 4, such as authentication data. In an example, processing circuitry 20 may identify, based at least in part on the identification data, IMD information that corresponds to IMD 6. As such, processing circuitry 20 may determine, based at least in part on the IMD information, an imaging program that defines one or more parameters for imaging an implantation site, such as the implantation site of patient 4. In one example, the imaging program may define one or more parameters for imaging one or more implantation sites of patient 4. The imaging program may include the site-check process application (e.g., mobile app(s) installed from an app store). In some examples, the imaging program may further include a site-check process tailored to the user (e.g., patient 4, HCP, etc.) of computing device(s) 2.

With the imaging program determined, computing device(s) 2 may initiate an imaging device (e.g., camera 32). In such examples, the imaging device may be configured to capture, in accordance with the imaging program, one or more frames of the image data. In an illustrative example, a camera application may be initiated automatically following the execution launch of the imaging program. With camera 32 initiated, computing device(s) 2 may receive, from camera 32, at least one frame of the one or more frames, the at least one frame including an image of the implantation site. From there, computing device(s) 2 may identify, from the at least one frame of the image data, an abnormality at the implantation site, in accordance with the various techniques of this disclosure. In one example, computing device(s) 2 may utilize image processing algorithms (e.g., AI engine(s) 28 and/or ML model(s) 30 (FIG. 2)) in order to identify such abnormalities. In some instances, computing device(s) 2 transmit the images to another that device that then detects an abnormality and transmits details of the abnormality back to computing device(s) 2, such that computing device(s) 2 may identify the abnormality.

In response to identifying the abnormality, computing device(s) 2 automatically trigger a supplemental image capture mode. That is, camera 32, when operating in the supplemental image capture mode, captures one or more supplemental images of the implantation site. In some examples, the supplemental image capture mode includes a video capture mode or other enhanced image capture mode (e.g., burst frames). In any case, with the supplemental image capture mode enabled, camera 32 may capture one or more supplemental images of the implantation site and transfer the supplemental images to computing device(s) 2. As such, computing device(s) 2 may receive the supplemental images of the implantation site. From there, computing device(s) 2 may output the one or more supplemental images of the implantation site. In some examples, computing device(s) 2 may output the one or more supplemental images to storage device 24 or to another device, via communication circuitry 26. The other device or computing device(s) 2 may perform various detection algorithms in order to determine whether the potential abnormality has a high chance of posing a health risk for patient 4. In turn, computing device(s) 2 may provide an implantation status, via UI 22 or to another device, that indicates a status of the implantation site and whether patient 4 should seek additional medical assistance.

In some examples, computing device(s) 2 may include a programming head or paddle (not shown). In such examples, computing device(s) 2 may interface with medical device(s) 6 via the programming head. The programming head may be placed proximate to the body of patient 4 near medical device(s) 6 (e.g., near an implantation site of an IMD, such as IMD 6). Computing device(s) 2 may include a programming head in order to improve the quality or security of communication between computing device(s) 2 and medical device(s) 6. In addition, computing device(s) 2 may include a programming head in order to improve the quality or security of communication between computing device(s) 2, medical device(s) 6, and/or edge device(s) 12.

In the illustrative and non-limiting example of FIG. 1, medical device(s) 6 include at least one IMD. In such examples, the at least one IMD may be implanted outside of a thoracic cavity of patient 4 (e.g., subcutaneously in the pectoral location illustrated in FIG. 1). In some examples, medical device(s) 6 may be positioned near the sternum near or just below the level of the heart of patient 4, e.g., at least partially within the cardiac silhouette. As used herein, an IMD may include, be, or be part of a variety of devices or integrated systems, such as, but not limited to, implantable cardiac monitors (ICMs), implantable pacemakers, including those that deliver cardiac resynchronization therapy (CRT), implantable cardioverter-defibrillators (ICDs), diagnostic devices, cardiac devices, etc. In some examples, the tools of this disclosure may be configured to monitor functioning of or user adaptation to implants other than CIEDs, such as spinal cord stimulators, deep brain stimulators, gastrological stimulators, urological stimulators, other neurostimulators, orthopedic implants, respiratory monitoring implants, etc.

In some examples, medical device(s) 6 may include one or more CIEDs. In some examples, patient 4 may interface with multiple medical device(s) 6, concurrently. In an illustrative example, patient 4 may have multiple IMDs implanted within the body of patient 4. In another example, medical device(s) 6 may include a combination of one or more implanted and/or non-implanted medical devices. An example of a non-implanted medical device includes a wearable device (e.g., monitoring watch, wearable defibrillator, etc.) or any other external medical devices configured to obtain physiological data of patient 4.

In some examples, medical device(s) 6 may operate as a therapy delivery device. For example, medical device(s) may deliver electrical signals to the heart of patient 4, such as an implantable pacemaker, a cardioverter, and/or defibrillator, a drug delivery device that delivers therapeutic substances to patient 4 via one or more catheters, or as a combination therapy device that delivers both electrical signals and therapeutic substances. As described herein, computing device(s) 2 may determine various imaging programs or at least aspects of an imaging program, such as biasing factors, based the type of medical device implanted in patient 4.

It should be noted that, while certain example medical device(s) 6 are described as being configured to monitor cardiovascular health, the techniques of this disclosure are not so limited, and persons skilled in the art will understand that the techniques of this disclosure may be implemented in other contexts (e.g., neurological, orthopedic, etc.). In some examples, one or more of medical device(s) 6 may be configured to perform deep brain stimulation (DBS), spinal cord stimulation (SCS), pelvic stimulation, peripheral nerve stimulation, muscle stimulation, etc.

Moreover, while certain example medical device(s) 6 are described as being electrical devices or electrically-active devices, the techniques of this disclosure are not so limited, and person skilled in the art will understand that, in some examples, medical device(s) 6 may include non-electrical or non-electrically-active devices (e.g., orthopedic implants, etc.). In any case, medical device(s) 6 may be configured to communicate medical data to computing device(s) 2, such as via a telemetry protocol, Radio-Frequency Identification (RFID) transmission, etc. As such, any medical device and/or computing device configured to communicate medical data may be configured to implement the techniques of this disclosure.

In some examples, medical device(s) 6 may be implanted subcutaneously in patient 4. In some examples, at least one of medical device(s) 6 takes the form of the Reveal LINQ™ Insertable Cardiac Monitor (ICM), or another ICM similar to, e.g., a version or modification of, the LINQ™ ICM, available from Medtronic plc. In such examples, medical device(s) 6 may facilitate relatively longer-term monitoring of patients during normal daily activities.

In a non-limiting example, medical device(s) 6 may include an IMD that is configured to operate as a pacemaker, a cardioverter, and/or defibrillator, or otherwise monitor the electrical activity of the heart of patient 4. In some examples, medical device(s) 6 can provide pacing pulses to the heart of patient 4 based on the electrical signals sensed within the heart of patient 4.

In some examples, medical device(s) 6 may also provide defibrillation therapy and/or cardioversion therapy via electrodes located on at least one lead and/or a housing electrode. Medical device(s) 6 may detect arrhythmia of the heart of patient 4, such as fibrillation of ventricles, and deliver defibrillation therapy to the heart of patient 4 in the form of electrical pulses. In some examples, medical device(s) 6 may be configured to deliver a progression of therapies, e.g., pulses with increasing energy levels, until a fibrillation of the heart of patient 4 is stopped. In such examples, medical device(s) 6 detects fibrillation employing one or more fibrillation detection techniques known in the art.

In some examples, system 100 may be implemented in a setting that includes network 10 and/or edge device(s) 12. That is, in some examples, system 100 may operate in the context of network 10 and/or include one or more edge device(s) 12. In some instances, network 10 may include edge device(s) 12. Similarly, computing device(s) 2 may include functionality of edge device(s) 12 and thus, may also serve as one of edge device(s) 12.

In some examples, edge device(s) 12 include modems, routers, Internet of Things (IoT) devices or systems, smart speakers, screen-enhanced smart speakers, personal assistant devices, etc. In addition, edge device(s) 12 may include user-facing or client devices, such as smartphones, tablet computers, personal digital assistants (PDAs), and other mobile computing devices.

In examples involving network 10 and/or edge device(s) 12, system 100 may be implemented in a home setting, a hospital setting, or in any setting comprising network 10 and/or edge device(s) 12. The example techniques may be used with medical device(s) 6, which may be in wireless communication with one or more edge device(s) 12 and other devices not pictured in FIG. 1 (e.g., network servers).

In some examples, computing device(s) 2 may be configured to communicate with one or more of medical device(s) 6, edge device(s) 12, or network 10 operating a network service such as the Medtronic CareLink® Network developed by Medtronic, Inc., of Minneapolis, MN. In some examples, medical device(s) 6 may communicate, via Bluetooth®, with computing device(s) 2. In some instances, network 10 may include one or more of edge device(s) 12. Network 10 may be and/or include any appropriate network, including a private network, a personal area network, an intranet, a local area network (LAN), a wide area network, a cable network, a satellite network, a cellular network, a peer-to-peer network, a global network (e.g., the Internet), a cloud network, an edge network, a network of Bluetooth® devices, etc., or a combination thereof, some or all of which may or may not have access to and/or from the Internet. That is, in some examples, network 10 comprises the Internet. In an illustrative example, computing device(s) 2 may periodically transmit and/or receive various data items, via network 10, to and/or from one of medical device(s) 6, and/or edge device(s) 12.

In addition, computing device(s) 2 may be configured to connect to cellular base station transceivers (e.g., for 3G, 4G, LTE, and/or 5G cellular network access), and Wi-Fi™ access points, as those connections are available. In some examples, the cellular base station transceivers may have connections that provide access to network 10. These various cellular and Wi-Fi™ network connections can be managed by different third-party entities, referred to herein as "carriers."

In some examples, system 100 may include one or more databases (e.g., storage device 96) that store various medical data records, cohort data, image data. In such examples, server(s) 94 (e.g., one or more databases) may be managed or controlled by one or more separate entities (e.g., internet service providers (ISPs), etc.).

In some examples, computing device(s) 2 may be configured to retrieve data from medical device(s) 6. The retrieved data may include values of physiological parameters measured by medical device(s) 6, indications of episodes of arrhythmia or other maladies detected by medical device(s) 6, and physiological signals obtained by medical device(s) 6. In some examples, computing device(s) 2 may retrieve cardiac EGM segments recorded by computing device(s) 2, e.g., due to computing device(s) 2 determining that an episode of arrhythmia or another malady occurred during the segment, or in response to a request, from patient 4 or another user, to record the segment.

In some examples, the user may also use computing device(s) 2 to retrieve information from medical device(s) 6 regarding other sensed physiological parameters of patient 4, such as activity or posture. In some examples, edge device(s) 12 may interact with medical device(s) 6 in a manner similar to computing device(s) 2, e.g., to program medical device(s) 6 and/or retrieve data from medical device(s) 6.

Processing circuitry of system 100, e.g., of medical device(s) 6, computing device(s) 2, edge device(s) 12, and/or of one or more other computing devices (e.g., remote servers), may be configured to perform the example techniques of this disclosure for determining an abnormality status of patient 4. The processing circuitry, may be referred to herein in some instances as a system of processors or a system of processing circuitry. In some examples, the system of processing circuitry of system 100 obtains physiological parameters, images, medical device diagnostics, etc. to determine whether to provide an alert to patient 4 and/or a HCP.

In some instances, processing circuitry of system 100, e.g., of computing device(s) 2, provides an alert to patient 4 and/or other users when a combination of patient health data (e.g., implantation site images, ECG parameters, etc.), medical device diagnostic data, and indicates the onset of an abnormality. The alert may be an audible alert generated by medical device(s) 6 and/or computing device(s) 2, a visual alert generated by computing device(s) 2, such as a text prompt or flashing buttons or screen, or a tactile alert generated by medical device(s) 6 and/or computing device(s) 2 such as a vibration or vibrational pattern. Furthermore, the alert may be provided to other devices, e.g., via network 10. Several different levels of alerts may be used based on a severity of a potential abnormality detected in accordance with one or more of the various techniques disclosed herein.

FIG. 2 is a block diagram illustrating an example configuration of components of at least one computing device 2 of computing device(s) 2. In the example of FIG. 2, the at least one computing device 2 includes processing circuitry 20, communication circuitry 26, storage device 24, and UI 22.

Processing circuitry 20 may include one or more processors that are configured to implement functionality and/or process instructions for execution within computing device(s) 2. For example, processing circuitry 20 may be capable of processing instructions stored in storage device 24. Processing circuitry 20 may include, for example, microprocessors, a digital signal processors (DSPs), an application specific integrated circuits (ASICs), field-programmable gate arrays (FPGAs), complex programmable logic devices (CPLDs), or equivalent integrated or discrete logic circuitry, or a combination of any of the foregoing devices or circuitry. Accordingly, processing circuitry 20 may include any suitable structure, whether in hardware, software, firmware, or any combination thereof, to perform the functions ascribed herein to processing circuitry 20.

A trained ML model 30 and/or AI engine 28 may be configured to process and analyze the user input (e.g., images of the implantation site, patient status data, imaging sequences, such as video data, etc.), device parameters (e.g., accelerometer data), historical data of a medical device (e.g., medical device(s) 17, IMD 6), and/or physiological parameters, in accordance with certain examples of this disclosure where ML models are considered advantageous (e.g., predictive modeling, inference detection, contextual matching, natural language processing, etc.). Examples of ML models and/or AI engines that may be so configured to perform aspects of this disclosure include classifiers and non-classification ML models, artificial neural networks ("NNs"), linear regression models, logistic regression models, decision trees, support vector machines ("SVM"), Naïve or a non-Naïve Bayes network, k-nearest neighbors ("KNN") models, deep learning (DL) models, k-means models, clustering models, random forest models, or any combination thereof. Depending on the implementation, the ML models may be supervised, unsupervised or in some instances, a hybrid combination (e.g., semi-supervised). These models may be trained based on data indicating how users (e.g., patient 4) interact with computing device(s) 2. For example, certain aspects of the disclosure will be described using events or behaviors (such as clicking, viewing, or watching) with respect to items (e.g., wound images, cameras, videos, physiological parameters, etc.), for purposes of illustration only.

In a non-limiting example, patient 4 may have difficulty capturing particular views of the implantation site. This helpful data may be shared across a health monitoring or computing network so that optimal results may be presented to more than one user based on similar interactions and user reactions to various capture modes. For brevity, these aspects may not be described with respect to events or behaviors regarding objects (e.g., data objects, such as augmented reality overlay objects). In some examples, processing circuitry 40 may use ML algorithms (e.g., DL algorithms) to, for example, monitor a progression of a wound that is healing or predict that a potential infection is occurring, for example, with respect to an implantation site of one of medical device(s) 6. In an illustrative and non-limiting example, AI engine(s) 28 and/or ML model(s) 30 may utilize a deep-neural network to localize an implantation site in an image and classify an abnormality status. In another example, AI engine(s) 28 and/or ML model(s) 30 may utilize Naïve Bayes and/or decision trees to synthesize (e.g., combine) data items and the analysis thereof (e.g., image analysis and ECG analysis) in order to obtain a comprehensive abnormality determination for patient 4 and include such comprehensive determinations in a report, such as for patient 4.

In another example, AI engine(s) 28 and/or ML model(s) 30 may be loaded with and trained on cohort parameters (e.g., age cohorts, IMD type cohorts, skin pigmentation cohorts, etc.) and combinations of cohort parameters. In such examples, AI engine(s) 28 and/or ML model(s) 30 may utilize historical reference interrogations for comparison when determining deviations from baseline parameters. In some examples, a physician or other HCP may maintain cohort parameters, such as by updating libraries of cohort parameters. As such, AI engine(s) 28 and/or ML model(s) 30 may be trained on such parameters to tailor an image analysis algorithm and thereby improve accuracy in a detection of an abnormality with respect to patient 4, rather than utilizing an untrained algorithm that may apply broadly to a general population of patients but with potentially less accuracy.

In addition, computing device(s) 2 may utilize different image processing algorithms and/or data synthesis algorithms, such as AI, ML, DL, digital signal processing, neural networks, and/or other techniques, depending on various different contexts and other various different resource constraints (e.g., processing power, network access, battery life, etc.).

In addition, trained AI engine(s) 28 may be used to learn about patient 4 over time and learn about an implantation site of a patient 4. In this way, AI engine(s) 28 may provide a personalized detection algorithm for detected abnormalities for a particular implantation site. In such examples, AI engine(s) 28 may be loaded with and trained on cohort parameters, using historical reference interrogations or images for comparison. In this way, computing device(s) 2 may provide a solution using different algorithm approaches (e.g., AI, ML, DL, digital signal processing, neural networks, and/or other techniques) in order to personalize the site-check process for patient 4.

A user, such as a clinician or patient 4, may interact with one or more of computing device(s) 2 through UI 22. UI 22 includes a display (not shown), such as a liquid crystal display (LCD) or a light emitting diode (LED) display or other type of screen, with which processing circuitry 20 may present health- or device-related information, e.g., cardiac EGMs, indications of detections of infections, changes in coloring around an implantation site, etc. In addition, UI 22 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through UI 22 presented by processing circuitry 20 of computing device(s) 2 and provide input. In one examples, UI 22 may allow a user to rotate images and adjust zoom levels using a touch screen of computing device 2 (e.g., pinch-to-zoom, gestures, gaze tracking, etc.).

As illustrated in the example of FIG. 1, computing device(s) 2 may, in some examples, include an imaging device. In an illustrative example, computing device(s) 2 may include a camera 32 or multiple cameras 32 (e.g., digital cameras), as example imaging device(s). As shown in FIG. 2, camera 32 may refer to a collective device including one or more image sensor(s) 34, one or more lens(es) 36, and one or more camera processor(s) 38 (e.g., image signal processor). In some examples, processing circuitry 20 may include camera processor(s) 38.

In some examples, multiple cameras 32 may be included with a single one of computing device(s) 2 (e.g., a mobile phone having one or more front facing cameras and one or more rear facing cameras). In some examples, computing device(s) 2 may include a first camera 32 having one or more image sensors 34 and one or more lenses 36, and a second camera 32 having one or more image sensors 34 and one or more lenses 36, etc. It should be noted that while some example techniques herein may be discussed in reference to frames received from a single camera (e.g., from a single image sensor), the techniques of this disclosure are not so limited, and a person of skill in the art will appreciate that the techniques of this disclosure may be implemented for any type of camera 32 and combination of cameras 32, such as a combination of cameras 32 that may be included with computing device(s) 2 or otherwise, communicatively coupled to computing device(s) 2. In some examples, image sensor(s) 34 represent one or more image sensors 34 that may include image-sensor processing circuitry. In some examples, image sensor(s) 34 include an array of pixel sensors (e.g., pixels) for capturing representations of light.

While shown as being optionally included with computing device(s) 2 (e.g., via dashed lines), the techniques of this disclosure are not so limited, and in some instances, camera 32 may be separate from computing device(s) 2, such as a stand-alone camera device or separate camera system. In any case, camera 32 may be configured to capture an image of an implantation site and transfer the image data to processing circuitry 20 via camera processor(s) 38. In some examples, camera 32 may be configured to achieve various zoom levels. In one example, camera 32 may be configured to perform cropping and/or scaling techniques to achieve a particular zoom level. In some examples, camera 32 may be configured to manipulate an output from image sensor(s) 34 and/or manipulate lens(es) 36 in order to achieve the particular zoom level.

In addition, camera 32 may be configured to capture a series of images (e.g., burst shot) or an image sequence (e.g., video data) of the implantation site. That is, camera 32 may be configured to operate according to a plurality of image capture modes. In an example, camera 32 may operate according to a first image capture mode, where camera 32 may be configured to capture one or more frames of still-images. In accordance with various techniques of this disclosure, camera 32 may be configured to capture the one or more frames at predefined perspective views of the implantation site, as well as capture the one or more frames at various angles relative to the predefined perspective views. In some examples, processing circuitry 20 may determine the presence of an abnormality (e.g., a potential infection) with respect to the particular view. In such instances, processing circuitry 20 may automatically trigger a supplemental image capture mode. As used herein, "automatically" or "automatic" generally means without user intervention or control. The supplemental image capture mode may be configured to automatically capture one or more supplemental still-images of the implantation site. In another example, the supplemental image capture mode may include a video capture mode in which camera 32 captures an image sequence at a particular frame rate.

In some instances, camera 32 and/or processing circuitry 20 may vary the particular frame rate based on the abnormality (e.g., likelihood of a potential abnormality being an actual abnormality, severity of abnormality, class of abnormality, etc.). In one example, camera 32 and/or processing circuitry 20 may determine a frame rate that is higher in the presence of a potential abnormality that is more likely to be an actual abnormality as compared to that of a lower likelihood potential abnormality determination. In such instances, processing circuitry 20 may initiate a video capture mode so as to capture video at a frame rate of more than the lower likelihood determination, which in some instances may be at least 120 frames per second at the lower end. That is, processing circuitry 20 may initiate the video capture mode at a higher frame rate relative to the 120 frames per second that processing circuitry 20 may initiate in other instances (e.g., less critical abnormality instances).

In some examples, computing device(s) 2 may include audio circuitry (not shown) for providing audible notifications, instructions or other sounds to the user, receiving voice commands from the user, or both. In some examples, computing device(s) 2 may provide audible notifications instructing a user to adjust a position of camera 32. In an illustrative example, computing device(s) 2 may determine that an implantation site is not properly framed within the field-of-view (FOV) of camera 32. In such instances, computing device(s) 2 may determine a target adjustment, such as a movement in a particular direction (e.g., a left or right lateral direction, etc.). In such instances, computing device(s) 2, in addition to or as an alternative to providing visual display of the target adjustment, may provide audible notifications (e.g., audible instructions) guiding the user of computing device(s) 2 in properly framing the implantation site and/or with capturing the target perspective view. In an illustrative example, computing device(s) 2 may provide a visual and/or audible notification requesting camera 32 be rotated in any direction and/or adjusted to a different position altogether, such as perpendicularly with respect to the implantation site (e.g., inward toward the implantation site or away from the implantation site) or positioned in other directions relative to implantation site. It will be understood that movement of camera 32 to different positions may additionally include rotations of camera 32, as well, in yaw, pitch, and/or roll directions of camera 32.

In some examples, computing device(s) 2 may provide audible notifications indicating to a user a direction to proceed through UI and/or the virtual check-in process (e.g., site-check process). In addition, computing device(s) 2 may provide audible notifications that indicate when a task is complete, such as when an imaging task is complete, when an authentication task (e.g., successful login), when an ECG measurement task is complete, or when any other task is complete. In another example, computing device(s) 2 may provide different audible notifications depending on particular outcomes. In one example, computing device(s) 2 may provide a quiet notification when the outcome of the virtual check-in process is such that no follow-up appointment is warranted (e.g., no potential infection, etc.), whereas computing device(s) 2 may provide a louder notification when the outcome of the virtual check-in process indicates that a follow-up appointment is advised, such as when the possibility of an abnormality (e.g., a potential infection) at the implantation site is identified.

Communication circuitry 26 may include any suitable hardware, firmware, software or any combination thereof for communicating with another device, such as medical device(s) 6. Under the control of processing circuitry 20, communication circuitry 26 may receive downlink telemetry from, as well as send uplink telemetry to, medical device(s) 6, or another device. Communication circuitry 26 may be configured to transmit or receive signals via inductive coupling, electromagnetic coupling, NFC, RF communication, Bluetooth®, Wi-Fi™, or other proprietary or non-proprietary wireless communication schemes. Communication circuitry 26 may also be configured to communicate with devices other than medical device(s) 6 via any of a variety of forms of wired and/or wireless communication and/or network protocols.

Storage device 24 may be configured to store information within computing device(s) 2 during operation. Storage device 24 may include a computer-readable storage medium or computer-readable storage device. In some examples, storage device 24 includes one or more of a short-term memory or a long-term memory. Storage device 24 may include, for example, read-only memory (ROM), random access memory (RAM), non-volatile RAM (NVRAM), Dynamic RAM (DRAM), Static RAM (SRAM), magnetic discs, optical discs, flash memory, forms of electrically-erasable programmable ROM (EEPROM) or erasable programmable ROM (EPROM), or any other digital media.

In some examples, storage device 24 is used to store data indicative of instructions for execution by processing circuitry 20. In addition, storage device 24 may store image data and/or supplemental image data. In some examples, storage device 24 may store frames of image data. That is, storage device 24 may store one or more images. In some examples, storage device 24 may store one or more images of a body of patient 4 (e.g., implantation site images, skin images for skin color analytics, skin surfaces proximate lead routings, etc.), physiological parameter images (e.g., ECG images), etc. In addition, storage device 24 may store imaging sequences, such as a sequence of images for video (e.g., video files). Storage device 24 may be used by software or applications running on computing device(s) 2 to temporarily store information during program execution. Storage device 24 may also store historical medical device data, historical patient data, timing information (e.g., number of days since implantation of an IMD, number of days since a particular physiological parameter has been above a certain threshold, etc.), AI and/or ML training sets, image or video data, etc.

Data exchanged between computing device(s) 2, edge device(s) 12, network 10, and medical device(s) 6 may include operational parameters of medical device(s) 6. Computing device(s) 2 may transmit data, including computer-readable instructions, to medical device(s) 6. Medical device(s) 6 may receive and implement the computer-readable instructions. In some examples, the computer-readable instructions, when implemented by medical device(s) 6, may control medical device(s) 6 to change one or more operational parameters, export collected data, etc. In an illustrative example, processing circuitry 20 may transmit an instruction to medical device(s) 6 which requests medical device(s) 6 to export collected data (e.g., ECGs, impedance values, etc.) to computing device(s) 2, edge device(s) 12, and/or network 10. In turn, computing device(s) 2, edge device(s) 12, and/or network 10 may receive the collected data from medical device(s) 6 and store the collected data, for example, in storage device 24. In addition, processing circuitry 20 may transmit an interrogation instruction to medical device(s) 6 which requests medical device(s) 6 to export operational parameters (e.g., battery, impedance, pulse width, pacing %, etc.).

In some examples, computing device(s) 2 may be coupled to external electrodes, or to implanted electrodes via percutaneous leads. In such examples, computing device(s) 2 may receive, from medical device(s) 6, and monitor physiological parameters, ECGs, etc., according to one or more techniques disclosed herein.

In the example illustrated in FIG. 2, processing circuitry 20 is configured to perform the various techniques described herein, such as the techniques described with reference to FIGS. 5-25. To avoid confusion, processing circuitry 20 is described as performing the various processing techniques proscribed to computing device(s) 2, but it should be understood that at least some of these techniques may also be performed by other processing circuitry (e.g., processing circuitry 40 of medical device(s) 17 (FIG. 4), processing circuitry 98 of server(s) 94, processing circuitry 64 of edge device(s) 12, etc.). In an illustrative example, processing circuitry 20 may capture image(s) of an implantation site, output images, for infection detection, to an analysis platform, determine, based on the images, presence of potential infection, output summary of an implantation status including potential infection information, and transmit a summary of the implantation status including the potential infection information. In this example, the analysis platform may be a separate program that processing circuitry 20 executes. In another example, the analysis platform may be a separate program that other processing circuitry from the system of processors executes instead.

FIG. 3 is a block diagram illustrating an example system 300 that includes one or more example computing device(s) 2, one or more medical device(s) 17, network 10, one or more edge device(s) 12, and one or more server(s) 94, in accordance with one or more techniques disclosed herein. In some examples, system 300 is an example of system 100 described with reference to FIG. 1. In another example, system 300 illustrates an example network system that hosts monitoring system 100. In some examples, medical device(s) 17 may be an example of medical device(s) 6 of FIG. 1. That is, medical device(s) 17 may include an IMD, CIED, etc., similar to that as described with reference to FIG. 1. In addition, medical device(s) 17 may include non-implantable medical devices, including wearable medical devices (e.g., smart watches, wearable defibrillators, etc.).

In this example, medical device(s) 17 may use communication circuitry 42 to communicate with one of edge device(s) 12 via a first wireless connection. In some examples, medical device(s) 17 may use communication circuitry 42 to communicate with an access point via a second wireless connection. The access point may include a device that connects to network 10 via any of a variety of connections, such as telephone dial-up, digital subscriber line (DSL), or cable modem connections. In some examples, an access point may be coupled to network 10 through different forms of connections, including wired or wireless connections. In some examples, one of computing device(s) 2 may serve as an access point for network 10. For example, a user device, such as a tablet or smartphone, may be co-located with patient 4 and may be configured to serve as an access point. In any case, computing device(s) 2, edge device(s) 12, and server(s) 94 are interconnected and may communicate with each other through network 10.

Medical device(s) 17, edge device(s) 12, and/or computing device(s) 2 may be configured to communicate, via various connections, over network 10 with remote computing resources (e.g., server(s) 94). The data network (e.g., network 10) may be implemented by server(s) 94 (e.g., data servers, remove servers, analytic servers, etc.). In an example, server(s) 94 may include a data server configured to store data and/or perform computations based on the data. In another example, server(s) 94 may include a data server configured to store data (e.g., a database) and send data to another one of server(s) 94 for data analytics, image processing, or other data computations, in accordance with one or more of the various techniques of this disclosure. In some examples, server(s) 94 may be implemented on one or more host devices, such as blade servers, midrange computing devices, mainframe computers, desktop computers, or any other computing device configured to provide computing services and resources. Protocols and components for communicating via the Internet or any of the other aforementioned types of communication networks are known to those skilled in the art of computer communications and thus, need not be described in more detail herein.

In some examples, one or more of medical device(s) 17 may serve as or include server(s) 94. That is, medical device(s) 17 may include enough storage capacity or processing power to perform the techniques disclosed herein on a single one of medical device(s) 17 or on a network of medical device(s) 17 coordinating tasks via network 10 (e.g., over a private or closed network). In some examples, one of medical device(s) 17 may include at least one of server(s) 94. For example, a portable/bedside patient monitor may be configured to serve as one of server(s) 94, as well as serving as one of medical device(s) 17 configured to obtain physiological parameter values from patient 4.

In some examples, server(s) 94 may communicate with each of medical device(s) 17, via a wired or wireless connection, to receive physiological parameter values from medical device(s) 17. In a non-limiting example, physiological parameter values may be transferred from medical device(s) 17 to server(s) 94 and/or to edge device(s) 12.

In some examples, server(s) 94 may be configured to provide a secure storage site for data that has been collected from medical device(s) 17, edge device(s) 12, and/or computing device(s) 2. In some instances, server(s) 94 may comprise a database that stores medical- and health-related data. For example, server(s) 94 may comprise a cloud server or other remote server that stores data collected from medical device(s) 17, edge device(s) 12, and/or computing device(s) 2. In some cases, server(s) 94 may assemble data in web pages or other documents for viewing by trained professionals, such as clinicians, via computing device(s) 2. In the example illustrated by FIG. 3, server(s) 94 includes a storage device 96 (e.g., to store data retrieved from medical device(s) 17) and processing circuitry 98. As described with reference to FIG. 2, computing device(s) 2 may similarly include a storage device and processing circuitry.

Processing circuitry 98 may include one or more processors that are configured to implement functionality and/or process instructions for execution within server(s) 94. For example, processing circuitry 98 may be capable of processing instructions stored by storage device 96. Processing circuitry 98 may include, for example, microprocessors, DSPs, ASICs, FPGAs, or equivalent integrated or discrete logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server(s) 94 and/or the processing circuitry of computing device(s) 2 may implement any of the techniques described herein to analyze physiological parameters received from medical device(s) 17, e.g., to determine a healing progression of patient 4 or a health of medical device(s) 17.

Storage device 96 may include a computer-readable storage medium or computer-readable storage device. In some examples, storage device 96 includes one or more of a short-term memory or a long-term memory. Storage device 96 may include, for example, ROM, RAM, NVRAM, DRAM, SRAM, magnetic discs, optical discs, flash memory, forms of EEPROM or EPROM, or any other digital media. In some examples, storage device 96 is used to store data indicative of instructions for execution by processing circuitry 98.

In some examples, one or more of computing device(s) 2 may be a tablet or other smart device located with a clinician (or other HCP), by which the clinician may program, receive alerts from, and/or interrogate medical device(s) 17. For example, the clinician may access data collected by medical device(s) 17 through computing device 2, such as when patient 4 is in between clinician visits to check on a status of a medical condition. In some examples, computing device(s) 2 may transmit data regarding images, video data, infection indications, imaging programs, training sets, ML models, IMD information, patient identification data, authentication data, etc. to one or more other computing device(s) 2, to edge device(s) 12, or to server(s) 94. Likewise, computing device(s) 2 may receive similar information.

In some examples, the clinician may enter instructions for a medical intervention for patient 4 into an application executed by computing device 2, such as based on a status of a patient condition determined by another one of computing device(s) 2, medical device(s) 17, edge device(s) 12, server(s) 94, or any combination thereof, or based on other patient data known to the clinician. The patient condition may include an implant status, such as a potential infection at an implantation site of the implant. Computing device 2 of a user may receive the instructions, via network 10. In return, computing device 2 may display a message on a display device indicating the medical intervention message.

In some examples, one of computing device(s) 2 may transmit instructions for medical intervention to another one of computing device(s) 2 located with patient 4 or a caregiver of patient 4. For example, such instructions for medical intervention may include an instruction to change a drug dosage, timing, or selection, to schedule a visit with the clinician, or to seek medical attention. In this manner, patient 4 may be empowered to take action, as needed, to address his or her medical status, which may help improve clinical outcomes for patient 4.

FIG. 4 is a functional block diagram illustrating an example configuration of one or more of medical device(s) 17, in accordance with one or more techniques disclosed herein. In the illustrated example, medical device(s) 17 include processing circuitry 40, a storage device 50, and communication circuitry 42. Additionally, medical device(s) 17 may, in some examples, include one or more electrodes 16, antenna(e) 48, sensing circuitry 52, switching circuitry 58, sensor(s) 62, and power source 56. As previously stated, medical device(s) 17 may be an example of one of medical device(s) 6 of FIG. 1. That is, medical device(s) 17 may include an IMD, CIED, etc., similar to medical device(s) 6 shown and described with reference to FIG. 1. In another example, medical device(s) 17 may include a non-implanted medical device, such as a wearable medical device, a medical workstation cart, etc.

In some examples, one of medical device(s) 17 may be a medical device implanted in patient 4, whereas another one of medical device(s) 17 may include camera 32, and as such, may perform one or more of the various techniques of this disclosure. That is, one of medical device(s) 17 may, via camera 32, capture images and/or the supplemental images, in accordance with one or more of the various techniques of this disclosure.

Processing circuitry 40 may include fixed function circuitry and/or programmable processing circuitry. Processing circuitry 40 may include any one or more of microprocessors, a controllers, DSPs, ASICs, FPGAs, or equivalent discrete or analog logic circuitry. In some examples, processing circuitry 40 may include multiple components, such as any combination of one or more microprocessors, one or more controllers, one or more DSPs, one or more ASICs, or one or more FPGAs, as well as other integrated or discrete integrated logic circuitry. The functions attributed to processing circuitry 40 herein may be embodied as software, firmware, hardware or any combination thereof.

In some examples, processing circuitry 40 may include AI engine(s) 44 and/or ML model(s) 46. AI engine(s) 44 and ML model(s) 46 may be similar to those AI engine(s) and ML model(s) described with reference to FIG. 2. In one example, ML model(s) 46 may include one or more DL models that are trained, for example, on various physiological parameter data, such as ECG data.

In the illustrated and non-limiting example of FIG. 4, medical device(s) 17 includes a plurality of electrodes 16A-16N (collectively, "electrodes 16"). Electrode(s) 16 may be referred to in some instances herein as a plurality of "electrode(s) 16," while in other instances may be referred to simply as "electrode 16," where appropriate. Electrodes 16 may be disposed within one bodily layer of patient 4, whereas at least one other electrode 16 may be disposed within another bodily layer of patient 4. In some examples, electrodes 16 may be configured for implantation outside of a thorax of patient 4.

Sensing circuitry 52 may be selectively coupled to electrodes 16 via switching circuitry 58, e.g., to select the electrodes 16 and polarity, referred to as the sensing vector, used to sense impedance and/or cardiac signals, as controlled by processing circuitry 40. In some examples, processing circuitry 40 may use switching circuitry 58 to select, e.g., via a data/address bus, which of the available electrodes are to be used to obtain various measurements.

In some examples, medical device(s) 17 may operate as a therapy delivery device. In such examples, medical device(s) 17 may include leads. The leads may extend to any location within or proximate to a heart or in the chest of patient 4. In an illustrative and non-limiting example, one of medical device(s) 17 may include a single lead that extends from one of medical device(s) 17 into a right atrium or right ventricle, or two leads that extend into a respective one of a right atrium and a right ventricle.

In some examples, one of medical device(s) 17 may be configured to include sensing circuitry, such as sensing circuitry 52, and one or more sensor(s), such as sensor(s) 54. In addition, in some examples, one of computing device(s) 2 may be configured to also include sensing circuitry, such as sensing circuitry 52, and one or more sensor(s), such as sensor(s) 54. In one example, one of computing device(s) 2 and/or one of medical device(s) 17 may include a heart rate sensor, pulse sensor, photoplethysmogram (PPG) sensor, blood oxygen saturation ($SpO_2$) sensor, etc.

Sensing circuitry 52 may be implemented in one or more processors, such as in one or more processors of processing circuitry 40 of medical device(s) 17 or processing circuitry 20 of computing device(s) 2. Sensing circuitry 52 is, in the example of FIG. 4, shown in conjunction with sensor(s) 54. Similar to processing circuitry 20, 98, 40, 64 and other circuitry described herein, sensing circuitry 52 may be embodied as one or more hardware modules, software modules, firmware modules, or any combination thereof.

In some examples, at least one of medical device(s) 17 may include a sensor device, such as an activity sensor, heart rate sensor, an accelerometer, a wearable device worn by patient 4, a temperature sensor, etc. That is, the one or more other medical device(s) 17 may, in some examples, be an external device that is external to patient 4 relative to a body of patient 4 or relative to medical device(s) 17 implanted in patient 4. In any case, medical device(s) 17 may interface with one another via communication circuitry 42, and may, in some examples, interface, in a similar fashion, with computing device(s) 2, edge device(s) 12, etc.

In one example, computing device(s) 2 may utilize orientation information of the medical device(s) 17, as indicated by the accelerometer data, in order to adjust image processing parameters, for example, of computing device(s) 2. In one example, shadows may be formed based on the orientation of the medical device(s) 17 that affect the image processing techniques of this disclosure, such that the image processing algorithms may adjust the processing techniques based on information about where medical device(s) 17 is situated within patient 4. In such instances, computing device(s) 2 may receive information from medical device(s) 2, such as temperature data and/or orientation data, and utilize such information during an analysis of image data. That is, computing device(s) 2 may analyze the image data received via camera(s) 32 in view of information received from medical device(s) 2 in order accurately characterize a potential abnormality. In a non-limiting and illustrative example, computing device(s) 2 may be analyzing the image data in view of a set of reference images of an implantation site uploaded immediately following implantation, where the set of reference images may no longer align with a positional state of medical device(s) 2 due to movement of medical device(s) 2, and thus, computing device(s) 2 may adjust the image processing techniques in order to maintain a degree of accuracy while, computing device(s) 2 or another device, ultimately performs the abnormality analysis.

In one example, computing device 2 may determine, from physiological parameters obtained via a second subsession, an ECG change that indicates device migration and as such, increases the likelihood that a potential abnormality is being detected from the image data. In such instances, computing device 2 may analyze the image data using a bias toward detecting an abnormality or may include, in a post-implant report, a heightened likelihood (e.g., probability, confidence interval) that is based on the likelihood of a potential abnormality determined from the first and second set data items.

In another example, computing device 2 may determine an ECG signal and utilize the ECG signal to map to an orientation of IMD 6. In some examples, computing device 2 may utilize ECG morphology data to map to an orientation of IMD 6 by identifying deflections in an ECG (e.g., PQRST data) or by comparing the ECG morphology data against a population-wide or cohort database. When an ECG morphology indicates a shift from a baseline ECG of patient 4, then computing device(s) 2 may indicate a device migration abnormality. A device migration abnormality may be indicative of a potential infection abnormality. In such instances, when computing device(s) 2 is uncertain whether a potential infection from a set of images, computing device(s) 2 may bias the determination toward an identification of an abnormality in view of the ECG morphology data. In another example, computing device 2 may obtain, from one or more of medical device(s) 17 (e.g., IMD 6), lead impedance information. Similar to the above, computing device 2 may utilize IMD information (e.g., lead impedance information) as an additional input for abnormality detection and/or prediction.

Communication circuitry 42 may include any suitable hardware, firmware, software or any combination thereof for communicating with another device, such as edge device(s) 12, network computing device (e.g., server(s)), other medical device(s) 17 or sensors, and/or computing device(s) 2. Under the control of processing circuitry 40, communication circuitry 42 may receive downlink telemetry from, as well as send uplink telemetry to, edge device(s) 12 or another device with the aid of an internal or external antenna, e.g., antenna 48. In addition, processing circuitry 40 may communicate with a network computing device via network 10, such as the Medtronic CareLink® Network. Antenna 48 and communication circuitry 42 may be configured to transmit and/or receive signals via inductive coupling, electromagnetic coupling, NFC, RF communication, Bluetooth®, Wi-Fi™, or other proprietary or non-proprietary wireless communication schemes. In one example, processing circuitry 40 may provide data to be uplinked, via communication circuitry 42, to edge device(s) 12, computing device(s) 2, and/or other devices, via network 10. In an illustrative example, computing device(s) 2 may receive a signal (e.g., uplink data) from a particular one of medical device(s) 17 (e.g., IMD 6). In such examples, computing device(s) 2 may determine, from the signal, information relevant to patient 4 and/or the particular one of medical device(s) 17 (e.g., IMD 6). In one example, the information may include device information (e.g., IMD information) that corresponds to the particular one of medical device(s) 17 or that corresponds to a set of medical device(s) 17, where the set may include, in addition to one of IMD(s) 6, other paired medical device(s) 17 (e.g., wearable devices, etc.).

In some examples, processing circuitry 40 may provide control signals using an address/data bus. In some examples, communication circuitry 42 may provide, via a multiplexer, data to processing circuitry 40, where the data is received externally via antenna 48. In some examples, medical device (s) 17 may transmit data to another device using a wired connection, such as a universal serial bus (USB) connection, ethernet connection over network 10 (e.g., a LAN), etc.

In some examples, storage device 50 includes computer-readable instructions that, when executed by processing circuitry 40, cause medical device(s) 17, including processing circuitry 40, to perform various functions attributed to medical device(s) 17 and processing circuitry 40 herein. Storage device 50 may include any volatile, non-volatile, magnetic, optical, or electrical media. For example, storage device 50 may include ROM, RAM, NVRAM, DRAM, SRAM, magnetic discs, optical discs, flash memory, forms of EEPROM or EPROM, or any other digital media. Storage device 50 may store, as examples, programmed values for one or more operational parameters of medical device(s) 17 and/or data collected by medical device(s) 17 for transmission to another device using communication circuitry 42. Data stored by storage device 50 and transmitted by communication circuitry 42 to one or more other devices may include electrocardiograms, cardiac EGMs (e.g., digitized EGMs), and/or impedance values, as examples.

The various components of medical device(s) 17 are coupled to power source 56, which may include a rechargeable or non-rechargeable battery. A non-rechargeable battery may be capable of holding a charge for several years, while a rechargeable battery may be charged from an outlet or other external charging device (e.g., inductive charging). In examples involving a rechargeable battery, the rechargeable battery may be charged on a daily, weekly, or annual basis, for example. In some examples, power source 56 may be separate from medical device(s) 17 and implanted in a separate implantation site of patient 4 that may be monitored for abnormalities, in accordance with one or more of the various techniques of this disclosure.

As described herein, medical device(s) 17 may include medical device 6 (e.g., IMD 6). In such examples, medical device(s) 17 may have a geometry and size designed for ease of implant and patient comfort. Examples of medical device(s) 17 described in this disclosure may have a volume of 3 cubic centimeters ($cm^3$) or less, 1.5 $cm^3$ or less, or any volume therebetween. In addition, medical device(s) 17 may include a proximal end and a distal end that are rounded to reduce discomfort and irritation to surrounding tissue once implanted under the skin of patient 4. An example configuration of a medical device 17 is described, as an example, in U.S. Patent Publication No. 2016/0310031, incorporated herein by reference in its entirety. Computing device(s) 2 may receive IMD information that include such configuration details of medical device 17 (e.g., IMD size, whether ends are rounded, length of elongated leads, if any, etc.). As described herein, computing device(s) 2 may utilize IMD information, such as IMD configuration, to train AI engine(s) 28 and/or ML models(s) 30 to provide an IMD-tailored abnormality assessment, in accordance with one or more of the various techniques of this disclosure.

FIG. 5 is an example UI visualization of an example computing device 502, in accordance with one or more techniques of this disclosure. Computing device 502 may be an example of one of computing device(s) 2 described with reference to FIG. 1, 2, or 3. Computing device 502 may include one or more cameras 32, in accordance with one or more various techniques of this disclosure. As described herein, the one or more cameras 32 may be separate from computing device 502 in some examples. In the illustrative and non-limiting example of FIG. 5 and others illustrating computing device 502, computing device 502 may include a mobile handheld device (e.g., a tablet, smartphone, etc.). While illustrated as a mobile handheld device, the techniques of this disclosure are not so limited. It will be understood that the UI visualization elements may be employed using various other devices and in various other settings, such as in a virtual reality, augmented reality, or mixed reality setting. That is, a user may use cameras 32 of augmented reality headsets in order to image an implantation site of patient 4, as well as navigate one or more of the UIs of this disclosure.

In some examples, a UI visualization or interface, as described herein, may include a UI page or screen of the relevant UI (e.g., UI 22). In some examples, a user may use navigation buttons (e.g., back, next, scroll buttons, etc.) to navigate laterally (e.g., forward, backward, etc.) through various UI pages or screens. In some instances, the UI visualization may include a virtual reality and/or augmented reality visualization, such as when computing device 502 includes a VR, AR, or MR headset. That is, the UI visualization may be presented as an immersive UI program that a user may interact with in a virtual and/or augmented reality space. A person of skilled in the art will appreciate that, although shown as different pages of a UI, computing device 502 may similarly present, instead of UI pages on a screen of a handheld mobile device, VR UI elements that a user may, nevertheless, navigate in order to conduct a virtual check-in process in accordance with the one or more of the various techniques of this disclosure or at least not inconsistent with the one or more of the various techniques of this disclosure.

In some examples, computing device 502 may present an interface 504 (e.g., via UI 22) that includes various sign-in options. In one example, interface 504 may include a sign in tile 506 or other sign in elements (e.g., camera icon 508). Computing device 502 may receive user input, as the user input relates to sign in tile 506, in order to invoke and/or initiate the virtual check-in process (e.g., the imaging program), in accordance with one or more techniques of this disclosure.

In an illustrative example, interface 504 may include a camera icon that first initializes camera 32 for sign in purposes. Computing device 502 may receive images from camera 32 and authenticate the user from the received images. In some examples, computing device 502 may perform facial recognition or implantation site (e.g., wound) characteristics recognition. In some examples, patient 4 may tap computing device 502 to the implantation site for NFC or RFID authentication. That is, computing device 502 may receive NFC or RFID indications. Computing device 502 may use such indications to identify and/or authenticate the particular user. In any case, computing device 502 may load, from storage device 24, the virtual check-in program (e.g., the imaging program) through or based on a reading or scan of a barcode (e.g., a one-dimensional barcode, a two-dimensional barcode, Quick Response (QR) Code™, matrix barcode, etc.). In some instances, the barcode may be included with a flyer given to patient 4 at implant time or shortly before/after the implantation procedure.

In some examples, computing device 502 may use one of medical device(s) 17 to authenticate user. Medical device(s) 17, in this instance, may include a wearable device that is able to authenticate the user (e.g., patient 4, HCP, etc.). The wearable device may, in some instances, include a wristband that includes a barcode, RFID chip, etc. In such instances, the user could tap medical device 17 to computing device 502 or computing device 502 may otherwise scan medical device 17. In some instances, the tap could be a contactless tap, such as an air tap that maintains a small air gap between devices. In any case, in a non-limiting example, computing device 502 may receive the authenticating information from medical device 17 and authenticate the user, such as by allowing the user to proceed to a next interface of the imaging program.

In some examples, UI 22 may include a button 600 (e.g., a soft key, hard key, etc.) that serves as a sign-in element. That is, button 600 may include a multi-function button that provides various sign-in options. In one example, button 600 may include a fingerprint or other biometric scanner. Button 600 may be on the front, back, or on any other portion of computing device 502.

In some examples, computing device 502 may not present interface 504, such as following a first sign in from a user. In such examples, a user may select a "remember this device," "remember me," and/or "I am the only relevant user for this device." Computing device 502 may receive the user input and forego a sign in interface for future sign-in events, accordingly. In some instances, a user may want to re-authenticate for each sign in, such as in cases where multiple IMD patients use the same computing device 502 for implantation site or other IMD monitoring.

FIG. 6 is an UI visualization of a launch session interface 602, in accordance with one or more techniques of this disclosure. In some instances, the launch session interface 602 may include a launch session icon 606 and/or a camera icon 608. Camera icon 608 may be similar to camera icon 508 except that, once already authenticated, camera icon 608 may function as a shortcut to launch a site-check session or other session of the virtual check-in process. In such examples, computing device 502 may receive user input of camera icon 608, and in turn, computing device 502 may initialize an imaging device (e.g., camera 32) and launch a site-check session, as described with reference to FIGS. 8, 15-22, and 25. It should be noted that the virtual check-in process may, in some instances, only include the site check-session, and as such actuation of launch session icon 606 may automatically launch the imaging program of this disclosure, rather than presenting the interface of FIG. 7.

In some instances, launch session interface 602 may include a profile interface 604. Profile interface 604, in some examples, may include an image or imaging sequence of patient 4, an image or imaging sequence of one or more relevant implantation sites of patient 4, or both. In this way, patient 4 may enjoy an even more personalized experience with using the virtual check-in UI. In such examples, computing device 502 may access the images or image sequences from storage device 24 or from another storage device, such as via network 10. The images or image sequences may be images from a previous session, such as from a previous session of computing device 502 executing the imaging program.

In some examples, the virtual check in program may be pushed to a device of patient 4, such as through cloud solutions. In such instances, computing device 502 may receive a push notification from edge device 12 or from another device (e.g., server(s) 94 via network 10). The push notification may, in some instances, originate from computing device 2 of another user, such as from computing device 2 of a HCP. In some instances, computing device 502 may receive a notification prompting a virtual check-in session based on a predetermined scheduling reminder. In such instances, an HCP may program a calendar timer that, when expired, causes computing device 502 to provide a push notification and/or automatically launch the virtual check-in session. In some examples, computing device 502 may, upon determining a schedule trigger or a push notification (e.g., a HCP push), provide an instruction to a user to open (e.g., launch) the virtual check-in program. In some instances, computing device 502 may automatically launch the virtual check-in program upon determining the schedule trigger or the push notification. That is, computing device 502 may automatically present interface 504 of FIG. 5, interface 602 of FIG. 6, or in some cases, may, as a default, present interfaces similar to those described with reference to FIGS. 14-16. In some instances, computing device 502 may determine whether the user requires authentication first or not before presenting various other interfaces.

In a non-limiting and illustrative example, computing device 502 may launch the imaging program (e.g., a virtual check-in) when prompted by patient 4, when scheduled on a specific date post implant, and/or when pushed a request during or around a clinic check. In some examples, computing device 502 may cause the virtual check-in program (e.g., the imaging program) to expire after a given time. In another example, the virtual check-in program (e.g., the imaging program) may not include an explicit expiration date (e.g., a so-called "evergreen" application).

In an illustrative example, computing device 502, when providing an interactive session, may identify a follow-up schedule for the patient. In an example, computing device 502 may receive the follow-up schedule, for example, from one of computing device(s) 2 of an HCP or may access the follow-schedule from a database via network 10. The follow-up schedule may define one or more time periods in which computing device 502 is configured to prompt the user to conduct the interactive session. In an illustrative example, the follow-up schedule may include a first time period for computing device 502 to provide a prompt 15 days after implantation or after removal of medical device 17 (e.g., IMD 6). In another example, computing device 502 may include a variable time period that an AI engine and/or ML model may determine for patient 4, such that different check-in schedules may exist for different patients based on various different criteria. In such examples, computing device 502 may provide the interactive session in accordance with the follow-up schedule.

FIG. 7 is an UI visualization of a menu interface 702, in accordance with one or more techniques of this disclosure. Upon initiation of the virtual check-in program (e.g., an imaging program), computing device 502 may output, via UI 22, an interactive UI, according to the virtual check-in program. In some examples, computing device 502 may provide a top-level interface that includes at least one first interface tile. The first interface tile may correspond to a site-check interface. In such instances, the site-check interface may include a subinterface level that is at a lower level relative to a level of the top-level interface. The interactive UI may present several tiles from which the user can choose. In the example, of FIG. 7, the app of this disclosure outputs a UI program that includes one or more graphical UI visualization elements (collectively, UI elements or "tiles").

While described in some instances as being provided as part of a hierarchal structure with tiered-levels, it will be understood that the techniques of this disclosure are not so limited, and that the subinterfaces may be separate from a menu interface in terms of what a user may see as a default when initialing receiving the site-check and other interfaces. In an example involving a mixed reality context, computing device 502 may present all interfaces at a single level, where a user may access each individual interface, for example, by panning the head of patient 4 around a virtual reality user interface. In an illustrative and non-limiting example, a user may access and/or initiate a site-check interface from the virtual reality user interface, where the virtual reality interface may, in some instances, convert to an augmented reality interface, such as when computing device 502 detects selection of a first tile (e.g., a site-check tile). In such instances, computing device 502 may transition to an augmented reality mode in which the user may, for example, image an implantation site of patient 4 via camera 32 (e.g., a head-worn camera or another camera communicatively coupled to computing device 502), in accordance with one or more of the various techniques of this disclosure. Once the site-check process is complete, computing device 502 may revert to a separate user interface (e.g., the top-level, menu interface or a second interface) that is again, in some instances, presented in a virtual reality context. While several examples may be described herein for user interaction with the site-check process of this disclosure, it will be understood that the site-check process and other processes of this disclosure may be provided in various contexts not necessarily described herein for sake of brevity.

As shown in the illustrative example of FIG. 7, the UI elements of interface 702 may include a patient status tile 706, a physiological parameters analysis tile 708, a device check tile 710, and/or a site check tile 712. The user (e.g., patient 4, caregiver, physician) can select any of these tiles (e.g., via a touch input) to leverage the functionalities associated with the description of each such tile. In some examples, the UI elements may comprise interactive graphical units that may be presented to a user via UI 22. In some examples, actuation of the camera icon may cause computing device 502 to automatically launch a site-check session so as to provide a shortcut to site-check page accessible via site-check tile 712.

In addition, any one of the interfaces described herein may include a session ID tracker tile 704. Session ID tracker tile 704 may provide session tracking information, such as date stamps, timestamps, session ID stamps, user information, etc. The session ID tracker may further include historical data regarding a previous session, such as a summary of the results of a previous report. In any case, computing device 502 may include such session tracking information when generating a new report for each particular session, such as for a site-check session.

In addition, individual interface may include individual tracker UI elements, that when computing device 502 detects selection of a particular tracker tile, computing device 502 may retrieve historical information regarding patient 4 and/or various medical device(s) 17 that correspond to patient 4. Computing device 502 may provide a pop-up interface that provides such information via UI 22 or in some instances, may automatically navigate a user, via UI 22, to a report and/or history interface for further review. In addition, computing device 502 may export such data (e.g., reports, history, etc.) to another interface and/or to another device altogether (e.g., one of computing device(s) 2 of a HCP, one of server(s) 94, edge device(s) 12, etc.). In one example, computing device 502 may export reports in response to detected selection of an export report button (e.g., a soft key), in response to detecting a user selection of a particular tracker tile. The exported reports may include multiple post-implant reports or a compilation report detailing an analysis of a plurality of data items (e.g., image data, ECG data, etc.). In an illustrative example, computing device 502 may detect selection of a site-check tracker tile, via a site-check interface, and in response, may generate and/or export one or more historical reports representing one or more analyses from one or more previously executed site-checks by a user.

In another example, computing device 502 may detect selection of a tracker tile (e.g., tracker tile 704) and in response, may generate and/or export a report corresponding to site-check results, physiological parameter results, and/or a comprehensive report corresponding to multiple results, as well as any individual summary reports (e.g., a historical report of site-check results). In another example, computing device 502 may generate historical reports that include an aggregation of any one or more of the reports, such that in response to detecting a selection of a particular tracker tile, computing device 502 may retrieve historical reports and compile and/or summarize reports from the past in order to produce a single post-implant historical report for export and/or display (e.g., via a pop-up interface). In such instances, computing device(s) 2 of an HCP may receive the post-implant report, via network 10, such that the HCP may review the historical record and/or a summary of the historical record for patient 4 (e.g., for medical device(s) 17 corresponding to patient 4).

FIG. 8 is a flowchart illustrating an example method of utilizing imaging techniques, in accordance with one or more techniques of this disclosure. The imaging techniques of this disclosure may be used to image an implantation site of a patient 4. In some examples, the example imaging method may follow from any one of the UI visualizations described with reference to any of FIGS. 5-7 or from FIG. 15.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may be configured to determine identification data for patient 4 (802). In an example, processing circuitry 20 may determine the identification data for patient 4. The identification data may include one or more of: biometric data, RFID data, NFC data, telemetry protocol data, user login information, authentication data, patient name or user name data, etc. In any case, a user may input identification data via computing device(s) 2 and/or via camera 32. In one example, computing device(s) 2 may include computing device 502 serving as a user check-in device. In such instances, computing device(s) 2 may determine identification data for patient 4 via input received via elements of interface 504 (e.g., via button 600, where button 600 includes a biometric scanner).

In some examples, patient 4 may provide authenticating data in order to gain access to perform the site-check process. The patient 4 may provide biometric data in some examples (e.g., facial data, fingerprint data, iris data, voice data, characteristic implantation site data, etc.). In one example, computing device(s) 2 may include a biometric scanner (e.g., camera 32, fingerprint scanner, etc.) that patient 4 or another user may use to provide authentication/biometric data. In some cases, camera 32 may image the implantation site to identify patient 4, where processing circuitry 20 includes AI engine(s) 28 and/or ML model(s) 30 trained to identify patient 4, to a certain degree of certainty, based on one or more initial images of the implantation site. Processing circuitry 20 may identify patient 4 from unique characteristics of the implantation site of patient 4. In another example, processing circuitry 20 may authenticate user based on wireless communication with IMD 6 of patient 4 (e.g., NFC data, telemetry protocol data, RFID data, etc.).

In some examples, patient 4 may or may not be the main user of computing device(s) 2 for purposes of engaging and/or navigating the site-check process. In an illustrative example, a user, separate from patient 4, may be the user of computing device(s) 2 for purposes of engaging and/or navigating the site-check process. That is, the user may coordinate with patient 4 while navigating the site-check process on behalf of patient 4. In an illustrative, a user, separate from patient 4, may login to access the imaging program. In such instances, the user, upon being authenticated to access the imaging program, may then identify patient 4. In some examples, the user may identify the patient by taking a photo of the patient, entering the patients name, scanning a barcode of the patient, imaging the wound site, etc. In an illustrative example, the user may take a photo of the face of patient 4 or of the implantation site. In any case, computing device(s) 2 may perform facial detection or wound characteristic detection in order to determine patient 4.

Processing circuitry, e.g., processing circuitry 20 of computing device(s) 2, processing circuitry 64 of edge device(s) 12, processing circuitry 98 of server(s) 94, or processing circuitry 40 of medical device(s) 17, may deploy image processing tools (e.g., AI engine(s) 28 and/or ML model(s) 30) in order to perform the authentication process. In an example, processing circuitry 20 may train the image processing tools on patient data, implantation site data, etc. In one example, the imaging processing tools may learn, when scanning an implantation site, for example, how the implantation site is healing over time (e.g., a healing trend). Generally speaking, characteristics of an implantation site may change over time and thus, processing circuitry 20 may, over time, adjust relevant portions of the identification algorithm accordingly. This is especially useful in instances where the identification algorithm of processing circuitry 20 utilizes, for example, image(s) of the implantation site to identify and/or authenticate a user. In such instances, processing circuitry 20 may still be able to accurately identify patient 4, even if an amount of time has passed between check-in sessions.

In some instances, while attempting to identify patient 4 via camera 32, processing circuitry 20 may detect a potential abnormality at this stage. Computing device(s) 2, in such instances, may request additional identification data in order to correctly and/or accurately identify the patient 4. In some instances, processing circuitry 20 may store authentication data (e.g., two-step authentication data) to storage device 24 so as to streamline the authentication and identification process for patient 4 in subsequent sessions. In another example, processing circuitry 20 may query a database (e.g., storage device 96 of remote server(s) 94), via network 10, that maintains patient data (e.g., usernames, passwords, implantation site characteristic data, implantation site images, etc.). In such instances, processing circuitry 20 may identify, from the patient data, patient 4 upon receiving search results from the database. In an illustrative example, processing circuitry 20 may receive user input, via UI 22, indicating a patient name of patient 4. Processing circuitry 20 may query the database and based on a result of the query, identify patient 4 as a known patient of system 100 (e.g., system 300).

Processing circuitry 20 may reference patient data (e.g., patient identifiers) such that the same computing device(s) 2 (or the same algorithm base) can be shared across multiple patients (e.g., in a clinic). As described herein, computing device(s) 2 may adjust, based on patient data, the base of the site-check algorithm in order to tailor the process and UI visualizations in order to accommodate each respective patient. In another example, a common site-check algorithm may be deployed to accommodate all patients of a certain class (e.g., nursing home patients, patients of a particular nursing home, etc.). In this way, the site-check algorithms may maintain and provide a particular level of uniformity for the various users of the site-check process, where those users may be part of a common class.

In some examples, a plurality of computing device(s) 2, while concurrently operating the imaging program, may both capture images of the implantation site of a single patient 4. That is, a computing device 2 of patient 4 may, while operating the imaging program, perform the techniques of this operation, as well as a computing device 2 of a caregiver. In such examples, computing device(s) 2 may synchronize data and/or analysis results in real-time or in some instances, at a later point in time, such as by waiting until a wireless connection between computing device(s) 2 is available or a network connection becomes available (e.g., a connection via network 10). In some instances, until computing device(s) 2 determines to perform a data synchronization process, computing device(s) 2 may store data locally, such as to storage device 24, or in some instances to storage device 62 of an edge device 12.

In some examples, following the receipt of authentication data identifying a user of the imaging program, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the identification data for patient 4. In such examples, the user of the imaging program may include a HCP, a family member of patient 4, patient 4, etc. To illustrate, processing circuitry 20 may authenticate and authorize the user to access the imaging program. Subsequently, processing circuitry 20 may receive, via UI 22, input data, such as user input, that effectively identifies patient 4. In one example, the input data includes barcode scanning data, selection of patient 4 from a dropdown menu (e.g., via a keyword search), manually entered patient information, etc. In any event, computing device(s) 2 may then determine, from the input, identification data for patient 4, such as by determining the name or ID of patient 4.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine IMD information that corresponds to one of medical device(s) 17 (e.g., IMD 6) of patient 4 (804). In an example, processing circuitry 20 may identify, based at least in part on the identification data, IMD information that corresponds to a particular one of medical device(s) 17. In some examples, the IMD information may include IMD implantation site information, such as where the implantation site is located on the body of patient 4, a size and shape of the implantation site, and other information regarding the implantation site. In another example, IMD information may include historical data relating to the implantation site of the IMD and/or historical data relating to the IMD. In some examples, the historical data may include images of the implantation site following the implantation procedure, wound characteristics, shape and size of the implantation site (e.g., the wound size), incision information, history of any complications during surgery, date of the implant, etc. In some examples, IMD information may further include IMD type information, IMD communication protocol information, an estimated orientation of medical device(s) 17 (e.g., IMD 6), data regarding one or more HCPs (e.g., surgeons, clinicians) responsible for implanting (e.g., inserting) medical device(s) 17 (e.g., IMD 6), information relating to one or more methods employed by the one or more HCPs when sealing the implantation site, images of the implantation site over time, etc. Example implantation methods and instruments are described, for example, in U.S. Patent Publication No. 2014/0276928, incorporated herein by reference in its entirety. In any case, computing device(s) 2 may determine the presence of a potential abnormality at the implantation site (e.g., a likelihood that the potential abnormality is an actual abnormality) based on the implantation methods and instruments used during the implantation surgery. In one example, computing device(s) 2 may compare image data of the implantation site against reference image data from a library of reference images, where the library may have tagged the reference images with various details such as implantation methods and instruments (e.g., library metadata). Computing device(s) 2 may determine an abnormality at the implantation site by, at least in part, referencing corresponding images from the reference library that include similar implantation method and instrument attributes to that of the implantation site computing device(s) 2 is imaging.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine an imaging program (806). In one example, processing circuitry 20 may determine, based at least in part on the IMID information, an imaging program that defines one or more parameters for imaging one or more implantation sites, including an implantation site of patient 4. The imaging program may include parameters regarding the proficiency of a user (e.g., novice, guided, manual, etc.) and may be tailored as such. In addition, the imaging program may be determined as part of a virtual check-in program that includes other non-imaging-based programs (e.g., device check programs). In some instances, processing circuitry 20 may tailor the imaging program, via AI engine(s) 28 and/or ML model(s) 30, in order to provide a further personalized UI experience for the user. In any case, the imaging program may include a program configured to generate UI data in accordance with one or more of the various techniques of this disclosure. In addition, the imaging program may include routines executable by the user, via computing device(s) 2, such as an imaging routine. The imaging routine may be designed to guide a user through a virtual site-check process and in some instances, may guide the user based on the proficiency level of the user (e.g., proficiency with handling imaging devices, proficiency with navigating UIs, etc.). It will be understood that the example UIs of this disclosure may be different for each individual user or class of users, as may be determined by AI engine (28) and/or ML model(s) 30 of computing device(s) 2 or of other devices.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may initiate an imaging device (808). The imaging device may be configured to operate in accordance with the imaging program. In such examples, the imaging device (e.g., camera 32) may be configured to capture one or more frames of image data. That is, the imaging device may be configured to capture the one or more frames of image data in accordance with the imaging program.

In some examples, processing circuitry 20 may cause camera 32 to initiate as the imaging device. In some examples, computing device 2 includes the imaging device. That is, computing device(s) 2 may include an on-board camera 32. In some examples, the imaging device may be a separate imaging device, such as a handheld camera 32. In such instances, computing device(s) 2 may transmit, via communication circuitry 26, a signal to an external imaging device, where the signal provides input to the external imaging device that initiates the imaging device so as to operate in accordance with the determined imaging program.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may receive an image of the implantation site (e.g., an implant-wound site) (810). The implantation site may be a site at which one or more of medical device(s) 17 (e.g., IMD 6) are implanted in patient 4 or in some instances, had been previously implanted in patient 4. In some examples, processing circuitry 20 may receive, via the imaging device (e.g., camera 32), one or more frames of image data, with at least one of the frames including an image of the implantation site.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine whether an abnormality has been identified at the implantation site (812). In an example, processing circuitry 20 may determine whether AI engine(s) 28 and/or ML model(s) 30 are identifying or have identified an abnormality at the implantation site of medical device(s) 17 (e.g., IMD 6).

An abnormality at an implantation site may include various abnormalities that may appear in conjunction with implantation sites of IMDs following implantation of medical device(s) 17 (e.g., IMD 6). Example abnormalities may include a potential infection at the implantation site, an abnormal healing at the implantation site, device migration (e.g., migration of IMD 6), etc. In an illustrative example, abnormal healing may include scar tissue abnormalities, such as raised scar tissue, etc. In addition, an abnormality may include a stitching or adhesive abnormality or another abnormality relating to a closure of the implantation site. In some examples, computing device(s) 2 may deploy various image processing engine(s), such as an image processing algorithm of AI engine(s) 28 and/or ML model(s) 30, in order to identify, classify, or assess a potential abnormality, and/or determine other indications of the abnormality.

In some examples, each class of abnormality may have a predefined severity level. Within each class of abnormality, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the abnormalities as having a range of severity levels. In an example, an implantation site infection may, in general, have a severity level that is higher relative to the severity level of an improper wound healing, for example, due to the formation of excessive scar tissue at the implantation site. This is because, generally speaking, an infection at the implantation site may pose a greater risk to the life of patient 4 compared to the issue of the formation of excessive scar tissue. In such examples, an indication of the abnormality may include the various severity assessments.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may receive an indication of the abnormality. In some instances, processing circuitry 20 may receive, via communication circuitry 26, an indication of the abnormality from another device, such as from one of edge device(s) 12. In such instances, computing device(s) 2 may determine, from internal analysis of the image or series of images and/or from an analysis external to computing device(s) 2, whether an abnormality is present, absent, or whether it is uncertain whether an abnormality is absent or present. An example external analysis includes transmitting the images to another device, such as one of server(s) 94, that performs the abnormality detection or identification. When processing circuitry 20 determine that no abnormality is present or that, based on the image(s) of the implantation site, the likelihood of an abnormality is low, the imaging program may proceed to output the image(s) of the implantation site (818; from NO at 812). In one example, processing circuitry 20 may output the image(s) to an internal storage device (e.g., storage device 24).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may output the image(s) of the implantation site when identifying an abnormality at the implantation site (812). In one example, computing device(s) 2 may output image(s) to an external abnormality determiner (e.g., AI engine(s) 28 and/or ML model(s) 30) that may determine the presence of a potential abnormality and/or the likelihood of the potential abnormality being an actual abnormality. In such instances, upon determining that no abnormality is present or that, based on the image(s) of the implantation site, the likelihood of an abnormality is low, computing device(s) 2, rather than continue outputting image(s), may proceed to the end of an imaging routine of the imaging program (820).

In some examples, the imaging program may involve the capture of multiple sets of images of the implantation site (e.g., various perspective views). In such examples, processing circuitry 20 may at determine to proceed with executing the imaging program (NO at 822). As such, processing circuitry 20 may cause camera 32 to capture the remaining images. That is, computing device(s) 2 may continue to receive, via the imaging device, image(s) of the implantation site (810).

In some instances, processing circuitry, e.g., processing circuitry 20 of computing device(s) 2, processing circuitry 64 of edge device(s) 12, processing circuitry 98 of server(s) 94, or processing circuitry 40 of medical device(s) 17, may identify an abnormality at the implantation site (YES at 812). In an example, processing circuitry 20 may determine whether an abnormality has been identified at the implantation site. In any case, processing circuitry 20 may identify the abnormality based on at least one frame of the image data. In one example, processing circuitry 20 may identify, from an analysis of the at least one frame, a potential abnormality.

In an illustrative and non-limiting example, processing circuitry 20 may determine, as the potential abnormality, the presence of a potential infection at the implantation site. That is, processing circuitry 20 may, in identifying the abnormality at the implantation site, determine the presence of a potential infection at the implantation site. In some examples processing circuitry 20 may detect the potential abnormality at the implantation site based on an analysis of the at least one frame. In another example, processing circuitry 20 may determine the potential abnormality by transmitting, via communication circuitry 26, an image or series of images to edge device(s) 12. That is, computing device(s) 2 may transmit one or more frames of image data to edge device(s) 12, where the frame(s) include one or more images of the implantation site. In addition, computing device(s) 2 may transmit the image or series of images, via network 10, to edge device(s) 12, medical device(s) 17 (e.g., a wearable device, a bedside workstation), and/or server(s) 94.

In some examples, computing device(s) 2 may transmit the image or series of images to another device, such as server(s) 94, via network 10, in which case, server(s) 94 may transmit the image or series of images to edge device(s) 12 for further analysis. That is, in some examples, computing device(s) 2 may transmit data, such as image or video data, indirectly to edge device(s) 12 and/or server(s) 94, via network 10. In one example, computing device(s) 2 may transmit data to edge device(s) 12, which, in turn, performs processing of the data and/or transmission of the data (e.g., edge-processed data) to server(s) 94 for further analysis. In such instances, edge device(s) 12 and/or server(s) 94 may determine the presence of a potential abnormality based on data (e.g., image data, video data, etc.) received from computing device(s) 2 via communication circuitry 26. In any case, computing device(s) 2 may determine the presence of a potential abnormality at the implantation site upon receiving the potential abnormality information from another device (e.g., edge device(s) 12, server(s) 94, etc.).

In an illustrative example, edge device(s) 12 and/or server(s) 94 may receive the image or series of images from computing device(s) 2. In some instances, edge device(s) 12 and/or server(s) 94 may perform an image processing analysis on the image or series of images prior to transmitting a result of the image processing analysis to computing device(s) 2 and/or edge device(s) 12. In some examples, edge device(s) 12 may identify the presence of the potential abnormality based on an analysis of the at least one frame. In some examples, edge device(s) 12 may deploy image processing engine(s) (e.g., via AI engine(s) 28 and/or ML model(s) 30) to determine the presence of the potential abnormality. In another example, edge device(s) 12 may perform some or all of the analysis with assistance from server(s) 94. That is, in some examples, server(s) 94 or edge device(s) 12 may include image processing engines or various analysis tools, configured to assist in the detection of a potential abnormality. Server(s) 94 and/or edge device(s) 12 may include image processing engines, such as AI engine(s) 28 or ML model(s) 30, described with reference to FIG. 2. In one example, server(s) 94 or edge device(s) 12 may include training sets for training one or more imaging processing engine(s). Server(s) 94 and/or edge device(s) 12 may perform the training of the image processing engine(s) or in some instances, may assist computing device(s) 2 with training the image processing engine(s). In another example, server(s) and/or edge device(s) 12 may transmit training sets to computing device(s) 2. In such instances, computing device(s) 2 may train the image processing algorithms (e.g., via AI engine(s) 28 and/or ML models(s) 30). In any case, computing device(s) 2 may determine, from the at least one frame, the presence of the potential infection at the implantation site based on an analysis of the at least one frame.

In addition, when identifying the abnormality, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine the likelihood that the potential abnormality is an actual abnormality (e.g., a severity metric, probability metric, etc.). In one example, processing circuitry 20 may determine the likelihood that the potential abnormality is an actual abnormality based on information that defines the potential abnormality (e.g., class of abnormality, abnormality characteristics, IMD type, etc.). In some instances, processing circuitry 20 may determine the likelihood by receiving, from another device (e.g., edge device(s) 12, server(s) 94, etc.), data indicating a likelihood of the potential abnormality being an actual abnormality or in some instances, data indicating a likelihood that the potential abnormality poses a health risk, whether serious or not. In a non-limiting example, processing circuitry 20 may determine the likelihood that a potential infection determined from a set of images represents an actual infection.

As a person skilled in the art would appreciate, an actual infection (e.g., a real infection) may be evidenced by a confirmed or verified presence of an infectious agent at the implantation site. In other words, a potential infection determination is an unverified determination that an implantation site has become infected with an infectious agent. That is, computing device(s) 2 may determine a potential infection as a possible infection based on data available to computing device(s) 2, but computing device(s) 2 may not diagnose an actual infection without additional input indicating that the infection is, in fact, an actual infection. In any case, computing device(s) 2 may determine, based at least in part on the at least one frame, a likelihood that the potential infection at the implantation site is an actual infection. In addition, an actual abnormality, such as a healing abnormality, may be evidenced by an actual abnormality in the healing process, such as may be confirmed or verified by another source (e.g., an HCP).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may use weighting factors (e.g., a built-in bias, error margins, etc.) when determining the likelihood of the potential abnormality being an actual abnormality. In one example, processing circuitry 20 may train AI engine(s) 28 and/or ML models(s) 30 on a pool of data, including patient data, implantation site data, rate of false positives, error margin information, etc., in order to determine an accurate likelihood of the potential abnormality being an actual abnormality. In one example, a built-in bias may include a bias toward confirming a potential abnormality as being more likely than not an actual abnormality when the IMD is of a particular type or when a particular number of images indicate a potential abnormality.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may trigger a supplemental image capture mode (814). That is, in response to identifying the abnormality, processing circuitry 20 may automatically trigger a supplemental image capture mode. In such instances, the imaging device may, when operating in the supplemental image capture mode, capture, automatically and/or manually, one or more supplemental images of the implantation site. In some examples, in response to identifying the abnormality, computing device(s) 2 may prompt a user, via UI 22, to manually capture, in accordance with the supplemental image capture mode, supplemental frames of image data. In some examples, processing circuitry 20 trigger the supplemental capture mode by transmitting a signal to camera 32 that causes camera 32 to initiate the supplemental image capture mode.

In some examples, the supplemental capture mode may be substantially the same as a first image capture mode, but where the supplemental capture mode is configured to produce supplemental image pursuant to additional instructions or capture parameters (e.g., zoom levels, flash parameters, contrast adjustments, white balance, so-called 3A parameters (e.g., auto-focus, auto-exposure, auto-white-balance), etc.). In some examples, the supplemental image capture mode may include a second image capture mode configured to capture supplemental images, with the second image capture mode being different than the image capture mode employed to capture the first set of one or more images of the implantation site (e.g., the first image capture mode).

In some examples, the supplemental image capture mode may include a video capture mode. Camera 32, when operating in video capture mode, captures an imaging sequence (e.g., a video sequence) at a particular capture rate. Processing circuitry 20 may receive supplemental images to supplement the previously received image(s) or subsequently received image(s) in order to more accurately determine the presence of an abnormality at the implantation site. In another example, the supplemental image capture mode may include an automatic zoom capture mode, configured to perform an automatic zoom, via camera 32, in order to capture supplemental images of the implantation site at various zoom levels.

Processing circuitry, e.g., processing circuitry 20 of computing device(s) 2, processing circuitry 64 of edge device(s) 12, processing circuitry 98 of server(s) 94, or processing circuitry 40 of medical device(s) 17, may receive supplemental image(s) of the implantation site (816). In an example, subsequent to triggering the supplemental image capture mode, processing circuitry 20 may receive the one or more supplemental images of the implantation site. The supplemental images may include an imaging sequence (e.g., video data) or in some instances, may include one or more images or series of images.

In such examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may output the one or more supplemental images of the implantation site (818). In an example, processing circuitry 20 may output video data to an internal storage or to one or more other devices via communication circuitry 26. In some examples, processing circuitry 20 may output, in addition to an imaging sequence, the still image(s) of the implantation site that processing circuitry 20 received prior to identifying the abnormality. In addition processing circuitry 20 may output an imaging sequence that includes one or more of the still image(s) received when operating camera 32 in a first image capture mode (e.g., a composite imaging sequence). That is, in some examples, processing circuitry 20 may combine one or more frames captured via a first image capture mode with one or more supplemental frames captured via the supplemental image capture mode in order to generate a composite sequence. In addition, computing device(s) 2 may encode, in the case of video data, the supplemental image data to create a compressed video file, and may do so with or without the still-image data from the first image capture mode. Processing circuitry 20 may, in such instances, output the one or more supplemental images as a compressed video file.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may output the image(s) to one or more image processors (e.g., AI engine(s) 28 and/or ML models(s) 30). In an example, processing circuitry 20 may deploy the image processors in order to further identify the potential abnormality. As described herein, in some examples, the image processors may be trained, for example, by processing circuitry 20, on a variety of training sets, such as IMD information, patient identification data, etc. Processing circuitry 20 may train the image processors on such data so that that the image processors may accurately and confidently identify abnormal implantation sites, along with likelihood/severity information, etc., as an imaging program may have defined such information. In some examples, computing device(s) 2 may output the various images to edge device(s) 12 and/or server(s) 94, where edge device 12 or server(s) 94 may advantageously deploy image processors (e.g., AI engine(s) 28 and/or ML models(s) 30). This may be useful where computing device(s) 2 have limited processing, memory, and/or processing resources, such that deploying such image processors may not be feasible from computing device(s) 2.

In some examples, prior to outputting the images, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine whether to continue with the supplemental mode, whether to revert to another image capture mode, or whether to output the images, end the imaging program, end the site-check process, etc. In an example, processing circuitry 20 may determine, upon receiving the supplemental images, whether to continue with image capture process (824). Processing circuitry 20 may determine not to continue (NO at 824), in which case processing circuitry 20 may output the images (818), end the imaging program (YES at 822), or end the site-check process altogether (820).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine to continue with the image capture process (YES at 824). Processing circuitry 20 may also determine whether to continue in the supplemental capture mode (826). If so, processing circuitry 20 may continue to cause camera 32 to capture the supplemental images (YES at 826). That is, processing circuitry 20 may continue to receive the supplemental images of the implantation site (816; from YES at 826). Otherwise, processing circuitry 20 may transition to another image capture mode, such as the first image capture mode, where processing circuitry 20 may continue to receive frames of image data representing the implantation site (NO at 826). In such instances, similar to the NO branch from 822, computing device(s) 2 may generate a prompt for the user to adjust the imaging device, such that computing device(s) 2 may receive, for example, images of the implantation site at various different perspectives.

FIG. 9 is an UI visualization of a patient status interface 902 that presents upon user request of patient status interface illustrated in FIG. 7. That is, FIG. 9 illustrates a UI visualization screenshots of invocation and initiation of UIs of the user-facing mobile device app of this disclosure upon the user selection of the patient status tile illustrated in FIG. 1. Various UI visualizations of this disclosure may include navigation buttons 906A-906N. The navigation buttons may include a back button 906A, a home button 906B, a next button 906C, an end button 906N, etc. In some instances, button 600 may function as a home button 906B that returns a user to a home of the computing device 502 or a home page of the application, such as interface 602 or 702. Interface 902 may include a start session tile 904, which when actuated, may launch a patient status UI configured to elicit or solicit patient input. In some examples, patient status interface 902 may serve as a hub for health information for patient 4. In one example, in addition to health information received via computing device 502, computing device 502 may also receive health information from other devices, wearable devices, or other software applications.

FIG. 10 is a UI visualization of an example patient status interface 1002, in accordance with one or more techniques of this disclosure. FIG. 10 illustrates a non-limiting example of a patient status questionnaire that either the backend system or the mobile device application of this disclosure may generate. The patient status questionnaire may be used to gauge information on a general health picture of patient 4, on implant-recovery-specific symptoms, medications that the patient has taken recently or will take soon, etc. Patient status interface 1002 may be a UI page that allows patient 4 or another user to enter information about patient 4, for example, via free text, dropdown menus, radio buttons, etc. In some examples, computing device(s) 2 may train AI engine(s) 28 and/or ML model(s) 30 on patient health information in order to more accurately determine abnormality information for an implantation site (e.g., severity of abnormality type, etc.). In one example, computing device(s) 2 may receive user input indicating soreness, redness, etc. at the implantation site. In such instances, AI engine(s) 28 and/or ML model(s) 30 may utilize such information when determining a potential abnormality. In some instances, computing device 502 may receive the patient health information as audio data, in which case, computing device 502 may train AI engine(s) 28 and/or ML model(s) 30 on the audio data.

FIG. 11 is a UI visualization of an example physiological parameter check interface 1102, in accordance with one or more techniques of this disclosure. The physiological parameter check interface 1102 may include buttons including, start physiological parameters analysis 1104, previous parameter 1106, next parameter 1108, and a physiological parameters menu. In some cases, physiological parameter check interface 1102 illustrates the interface that is invoked or initialized upon the user selecting the physiological parameters analysis tile illustrated in FIG. 7 (e.g., tile 708).

FIG. 12 is a UI visualization of an example physiological parameter check interface 1202, in accordance with one or more techniques of this disclosure. In an illustrative example, physiological parameter check interface 1202 includes an ECG analysis page. Physiological parameter check interface 1202 illustrates, as a non-limiting example, two outcomes, namely, a normal ECG analysis 1204 and an abnormal ECG analysis 1208 (e.g., as indicated by an abnormality 1210 observed in the ECG). The ECG may be received from one of medical device(s) 6, medical device(s) 17 (e.g., an IMD), or another device such as a watch, fitness tracker, or other wearable device configured to collect ECG data. In any case, computing device(s) 2 may obtain ECG data for analysis. In a non-limiting and illustrative example, the analysis may include a normal result 1206 or abnormal result 1212, in which case an alert to contact a clinic may be warranted.

Examples of ECG collection aspects include ECG collected directly from one of medical device(s) 17 (e.g., medical device(s) 6). In some examples, medical device(s) 17 may include a wearable device, such as an activity tracker, heart rate monitor, pulse monitor, pulse oximetry monitor, temperature monitor (e.g., core temperature monitor, surface temperature monitor). In addition, computing device(s) 2 may receive ECG that is collected from wearables or other ECG devices (e.g., medical device(s) 17). In some examples, computing device(s) 2 may provide for programmed connectivity (e.g., via a dropdown menu) with medical device(s) 17. Computing device(s) 2 may receive input, via the dropdown menu, from patient 4 or HCP indicating a target programming connection for one or more of medical device(s) 17 (e.g., a wireless connection). In some examples, the virtual check-in application of this disclosure includes a device-aware application. That is, computing device(s) 2 may store information regarding what device computing device(s) 2 is communicating with. In some instances, computing device(s) 2 may determine such information through a pairing process. In another example, computing device(s) 2 may receive such information as a download from a physician. In some examples, computing device(s) 2 may determine such information from user selection from a dropdown menu (e.g., a device dropdown menu).

In some examples, computing device(s) 2 may include device-aware aspects that are based on an interrogation of one of medical device(s) 17. In another example, computing device(s) 2 may receive device parameters and information as pushed from another device, such as from a push notification. In some examples, computing device(s) 2 may receive device information from another one of computing device(s) 2 operated by a HCP, where the HCP may populate the correct information via UI 22.

In some instances, computing device(s) 2 may receive physiological parameters or physiological parameter analysis results directly from another device or indirectly from another device, such as over network 10. In an illustrative example, computing device may receive an ECG or an image of an ECG from another device. That is, a scanner program may scan an ECG and upload the scan in any suitable document format. Likewise, a loader program may upload an image of an ECG for use by computing device(s) 2. In some instances, computing device(s) 2 may include the scanner program and/or the loader program. In such instances, computing device(s) 2 may upload the physiological parameter information to another device or store the parameter information to an internal storage (e.g., storage device 24).

FIG. 13 is a UI visualization of an example device check interface 1302, in accordance with one or more techniques of this disclosure. Device check interface 1302 illustrates an example interface that may be invoked or initialized upon user selection of the device check tile illustrated in FIG. 7 (e.g., tile 710).

FIG. 14 is a UI visualization of an example device check interface 1402, in accordance with one or more techniques of this disclosure. Invocation of device check interface 1402 may cause computing device(s) 2 to interrogate medical device(s) 17 (e.g., IMD 6). In an example, computing device(s) 2 may interrogate medical device(s) 17 via various close-range wireless communication protocols and telemetries. That is, processing circuitry 20 may receive, via a computing network, the second set of data items. In some examples, the computing device may receive medical device interrogation data over network 10, directly from the one or more medical device(s) 17, from one or more edge device(s) 12, or any combination thereof.

Computing device(s) 2 may populate device check interface 1402 with various parameters for the device check portion, as shown. In various examples, the backend system of a cloud-based implementation may push the interrogation information to the mobile device, or the mobile device app may initiate the interrogation locally at the mobile device. In any case, users may then audit the performance of medical device(s) 17 (e.g., IMD 6), by invoking the app and pinging the statistics as shown in FIG. 14. In the example of FIG. 14, the monitored statistics include, but are not necessarily limited to, battery strength, impedance, pulse width, pacing percentage, pulse amplitude, and pacing mode. In some instances, computing device(s) 2 may automatically schedule a routine device-check or follow-up based on the results of the interrogation.

FIG. 15 is a UI visualization of an example site check interface 1502, in accordance with one or more techniques of this disclosure. Site check interface 1502 illustrates the invocation or initiation of a site-check process upon the user selection of the site check tile illustrated in FIG. 7 (e.g., tile 712). As described herein, however, site check interface 1502 may, in some instances, be decoupled from the virtual check-in interface 702 of FIG. 7. As such, site check interface 1502 may, in some examples, exist as a standalone UI that includes site check interface 1502 or a similar site check interface. In such examples, a standalone site-check UI may, in addition, include sign-in and launch session interfaces, similar to those described with reference to FIGS. 5 and 6.

Site check interface 1502 may include a start check 1504 button and a camera icon 608 button. Camera icon 608 may automatically start a session, such as when a user does not wish to adjust any camera parameters. In some examples, however, a user may wish to adjust camera parameters prior to starting. Although not illustrated, site check interface 1502 may include additional options to adjust various camera parameters. In addition, a user may adjust camera parameters on the fly while using the camera to capture images of the implantation site. In some examples, camera parameters include adjusting between a front-facing camera and another camera, lighting, zoom levels, focus, contrast, etc.). Once ready, processing circuitry 20 may receive user selection, via UI 22, of start check 1504 in order to advance to a next page or interface of the site-check process (e.g., a next graphical interface of the site-check UIs).

FIG. 16 is a UI visualization of an example site check interface 1602, in accordance with one or more techniques of this disclosure. Site check interface 1602 includes a photographs icon 608 configured to cause camera 32 to capture images of implantation site 1604. Similarly, site check interface 1602 includes a video icon 1608 configured to cause camera 32 to capture video of implantation site 1604. Processing circuitry 20 may, in some examples, automatically trigger such video capture as a supplemental image capture mode. In addition, a user may enter video capture mode manually. A user may set a video capture parameter for either automatic or manual mode, such as a frame rate, sample rate, etc. In some examples, processing circuitry 20 may receive such video capture parameters in terms of lower and upper limits. In an illustrative and non-limiting example, processing circuitry 20 may receive user input that defines the lower limit for video capture at 120 frames per second and defines the upper limit at 140 frames per second. When processing circuitry 20 triggers a video capture mode as the supplemental image capture mode, processing circuitry 20 may initialize the video camera at a parameter that satisfies a particular frame rate, such as one defined by an upper and lower limit and/or defined by default. In the above illustrative example, processing circuitry 20 may determine 125 frames per second as the camera parameter and initialize the video camera accordingly. Processing circuitry 20 may do so, in some instances, based on various camera limitations, memory storage limitations, potential abnormality detections, etc.

In some instances, a user may point the camera at implantation site 1604, in which case, processing circuitry 20 may automatically perform an abnormality detection, with or without already receiving a command to capture an image. In addition, processing circuitry 20 may cause camera 32 to automatically capture an image of the implantation site when processing circuitry 20 detects an abnormality. Once a photo has been captured, an implant status indicator 1606 may appear indicating a status of the implant, including the implantation site 1604. In the example of FIG. 16, the implantation site is indicated as being "Normal".

In some examples, processing circuitry 20 may implement regional comparison zones for differential diagnostics (e.g., Dx). Processing circuitry 20 may perform a gradient analysis of implantation site 1604 and, for example, sternum areas for different skin tones, to determine a differential diagnostic. Processing circuitry 20 may reference the differential diagnostic to determine whether a potential abnormality is present at implantation site 1604. AI engine(s) 28 and/or ML model(s) 30 also use various measurements in the user-provided picture to determine whether the implantation site is within a threshold of the "normal" state. In some instances, processing circuitry 20 may overlay a ruler or other augment or overlay on the image to assist the user with capturing an image useful for measurements. That is, processing circuitry 20 may provide an augment or another frame that the user can use to get the correct distance and/or perspective of the implantation site. In an illustrative example, processing circuitry 20 may guide a user to image the implantation site where camera 32 is a target distance from the implantation site and in some instances, from a second target distance from the implantation site. Processing circuitry 20 may further guide a user to image the implantation site at a target angle relative to the implantation site or relative to a reference plane of camera 32 (e.g., a starting position of computing device(s) 2). In such examples, processing circuitry 20 may use overlays, augmented rulers, etc., such as in an augmented reality implementation, in order to capture each view at particular distances, angles, etc.

In some examples, processing circuitry 20 may train AI engine(s) 28 and/or ML model(s) 30 to discern relative measurements with respect to color and marks. In this way, processing circuitry 20 may compensate for different appearances of a wound on different skin colors, across different patient demographic cohorts, etc. In some examples, the image processing AI may use regional comparisons within the same picture to distinguish the implantation site from areas of the skin of patient 4 that are unaffected by the implantation (e.g., to derive relative or delta information). The image processing AI may also be trained to compensate for differences between systemic infections and implant site-originated infections, such as at the pocket or incision. In some examples, processing circuitry 20 may deploy AI engine(s) 28 and/or ML model(s) 30 to determine, from a captured image, Red, Green, and Blue (RGB) image details, Pantone®, and other color schemes. In addition, AI engine(s) 28 and/or ML model(s) 30 to determine, from a captured image, shape of an implantation site wound closure, whether the image comprises glossiness, etc. Processing circuitry 20 may, based on the various image processing techniques, determine whether an image of an implantation site includes a potential abnormality or if the implantation site otherwise satisfies the predefined threshold of the "normal" state.

FIG. 17 is a UI visualization of an example site check interface 1702, in accordance with one or more techniques of this disclosure. The example site check interface 1702 of FIG. 17 illustrates an abnormal implantation site outcome. When detecting an abnormality processing circuitry 20 may provide a visual alert 1706. Processing circuitry may include in visual alert 1706 descriptive information regarding the potential abnormality. In some examples, processing circuitry may include with visual alert 1706 a medical intervention instruction for the user to perform some action (e.g., contact clinic, etc.).

In some examples, processing circuitry 20 may provide augmented reality overlay 1704 on interface 1702. Processing circuitry 20 may do so in order to assist a user in capturing an image or imaging sequence of the implantation site at a particular angle and with a size reference. In addition, AI engine(s) 28 and/or ML model(s) 30 may provide adjustments for a respective algorithm based on a tendency that, as an implantation site slowly heals, the post-op image will change gradually. In some examples, processing circuitry 20 may train AI engine(s) 28 and/or ML model(s) 30 to detect deviations from the "healthy" state, in some examples. The healthy state may include characteristics of the implantation site from a previous site-check session in which no abnormality was detected.

When processing circuitry 20 determines an abnormality, processing circuitry 20 may automatically trigger a supplemental image capture mode. In an example involving a video capture mode, processing circuitry 20, while capturing video data, may automatically take photographs during the video capture. In some instances, processing circuitry 20 may automatically trigger the supplemental capture mode, even before a user commands any capture of any image. That is, processing circuitry 20 may determine an abnormality from an image captured by one of image sensor(s) 34 prior to a user actuating photograph button 608 requesting longer term capture of an image. In another example, processing circuitry 20 may wait until an image is captured, via an explicit command from a user before determining whether to trigger the supplemental capture mode.

FIG. 18 is a flowchart illustrating an example method of utilizing imaging techniques pursuant to various proficiency levels, in accordance with one or more techniques of this disclosure. Described with reference to the interfaces of FIGS. 15-17, for example, processing circuitry, e.g., processing circuitry 20 of computing device(s) 2, processing circuitry 64 of edge device(s) 12, processing circuitry 98 of server(s) 94, or processing circuitry 40 of medical device(s) 17, may receive a UI command to start the site check session (1802). In one example, processing circuitry 20 may receive indication of user input selecting start check icon 1504.

During the site-check session, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine a level of proficiency of a user (1804). The level of proficiency may be with respect to proficiency in performing imaging techniques or more specifically, imaging implantation sites of IMDs. In addition, or alternatively, the level of proficiency may be with respect to proficiency with performing UI operations. The levels of proficiency may include manual imaging (1806), guided imaging (1808), or automated imaging (1810). Because clear images of the implantation site help with accurate infection diagnosis, the processing circuitry 20, via the imaging program, can provide "novice" and "intermediate" user guides. In addition, processing circuitry 20 may automate capture of multiple images of the implantation site, in some examples.

In some examples, processing circuitry 20 may determine the imaging program by determining the proficiency level of a user. Processing circuitry 20 may determine the proficiency level based on user data, such as how long a user has been using the program. In another example, processing circuitry 20 may test the user to determine the proficiency of the user.

In some examples, processing circuitry 20 may determine, based on the proficiency level, an imaging mode. Example imaging modes include: (i) "novice" (e.g., an elderly patient taking photos themselves), (ii) "intermediate" (e.g., a smartphone-proficient patient or caregiver), (iii) "expert" (a clinic technician trained with using the infection-detection program and system). The "expert" can be a trained professional who can take the multiple views of a patient's wound-site with clarity. As such, processing circuitry 20 may capture, according to the imaging mode, the at least one frame.

In an illustrative example, a method for manual imaging an implantation site is described. Camera 32 captures image(s) of or adjacent the implantation site during a manual session (1812). Processing circuitry 20 may capture images at a specific point in time following implantation of the medical device 17 (e.g., IMD 6). In some examples, a first one of computing device(s) 2 may store the various images to storage device 24 (1814). In addition, or alternatively, computing device(s) 2 may transmit the various images to a secure backend system. Example backend systems include edge device(s) 12, server(s) 94, and/or other components of network 10 (e.g., Medtronic CareLink® Network). Processing circuitry of the backend system (e.g., processing circuitry 64, processing circuitry 98, etc.) may process the various images and/or route the images to various other devices. Processing circuitry 20 may, in some examples, store image(s) to storage device 50 of medical device(s) 17.

Similarly, processing circuitry 20 may store such data to storage device 62 of edge device(s) 12 or to storage device 96 of server(s) 94.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may utilize guided imaging 1808 or automated imaging 1810 modes in order to increase a scaling capability of system 300. That is, system 300 may seamlessly support an increasing number of implantation events and virtual follow-up visits for the implantations, in accordance with one or more of the various techniques of this disclosure.

In some examples, processing circuitry 20 may support a guided imaging mode (1808). In such examples, guided imaging mode may differ from manual imaging mode 1806 in that, instead of providing implantation site views from a single session post-implant, processing circuitry 20 implements, via UI 22, guidance for a user (e.g., patient 4, caregivers, etc.) to image the implantation site at regular intervals, various perspective views, various zoom levels or with other particular camera parameters (e.g., infrared imaging, etc.), etc., in order to identify abnormalities, implantation site healing or worsening over time, etc. Processing circuitry 20 may guide the user by providing scheduled reminders. The reminders may be pushed to a computing device 2 of the user. In addition, a HCP (e.g., the prescribing physician) can access the imaging program to follow-up on patient 4 when the implantation site does not show signs of healing over time. That is, processing circuitry 20 may determine an abnormality, such as an implantation site that does not display signs of healing over time, and as such, may transmit a notification to a computing device 2 of the HCP, such that the HCP may access the imaging program, including images, etc., via UI 22.

In some examples, automated core-device analysis methods (1810) may provide further improved scalable solutions for implantation site abnormality diagnosis, as compared to the scaling capability in the manual imaging mode (1806). As described herein, the various techniques of this disclosure are applicable to both a "cloud" implementation (i.e., Medtronic CareLink® Network) and "edge" implementation (i.e., on the app). The applicability of the various techniques of this disclosure may be use-case dependent.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may later synchronize, for ease of access and/or algorithm tuning, the data and results of the image analysis. In one example, processing circuitry 20 may coordinate with other processors of the processing system to synchronize data and results of the image analysis between an edge network (e.g., computing device(s) 2, edge device(s) 12, medical device(s) 17, etc.) and a cloud network (e.g., server(s) 94).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may deploy, as part of the imaging program, a ML model (e.g., a DL model) and/or AI engine that analyzes, for abnormalities, each image and/or imaging sequence obtained during a site-check process. In an illustrative and non-limiting example, the imaging program may provide three levels of detections: "abnormality present," "abnormality absent," "uncertain." In an example, where processing circuitry 20, via the imaging program, detects an abnormality in any of the images with a high likelihood, then processing circuitry 20 may determine an abnormality presence at that time. Where processing circuitry 20 determines there to be no abnormality in all images with a high likelihood, then processing circuitry 20 may determine an abnormality absence at that time. Where processing circuitry 20 does not detect an abnormality in any of the images with a high likelihood, but for some images the detection is uncertain, all the images from that session may be provided for human expert review. If the human expert detects an abnormality, the patient can be asked to follow-up with the prescribing physician.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine thresholds for abnormality presence or absence based on a tradeoff between missed abnormality diagnosis, in which case, patient 4 might get belated care, and false infection diagnosis. In some examples, processing circuitry 20 may, when unable to detect the presence or absence of an infection that satisfies a particular threshold (e.g., "infection uncertain"), processing circuitry 20 may apply a biasing factor to the detection. In one example, processing circuitry 20, when determining whether an infection is present, may strategically err on the side of false detections, such that in such instances of false detection, the images may still be output for further review (e.g., expert review), and the likelihood of missing an abnormality diagnosis, such as an infection diagnosis, is dampened as much as possible.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine parameters of the imaging program, including thresholds for abnormality detection, based on whether the implantation site hosts a first-time implant or an implant that has been changed out, IMD type (e.g., CIED type), skin tone and age of patient 4 being monitored, etc. In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine parameters of the imaging program based on information regarding various abnormality control procedures. In an illustrative examples, an abnormality control procedure may include information that a HCP (e.g., a surgeon or implanting clinician) used Medtronic's TYRX™ Absorbable Antibacterial Envelope, or another similar element, during implantation of the medical device. As will be understood, TYRX™ is a mesh envelope that holds an implantable cardiac device, implantable neurostimulator, or other IMD. Processing circuitry 20 may determine a biasing factor for the based on the presence of such control procedures. This is because TYRX™ is designed to stabilize the device after implantation while releasing antimicrobial agents, minocycline and rifampin, over a minimum of seven days, and thus, the likelihood of an abnormality during that time is lower relative to an implant that does not include such control procedures. In other words, patients with a TYRX™ envelope as part of an implant generally tend to have a lower chance of infection than patients without a TYRX™ envelope. In any case, the various abnormality detection algorithms of this disclosure may be configured to be more sensitive and/or less specific (e.g., imaging program parameters) for non-TYRX™ patients as compared to imaging program parameters used with respect to TYRX™ patients.

In similar respects, processing circuitry 20 may determine imaging program parameters with the objective of increasing the negative predictive value. That is, if processing circuitry 20 determines, in accordance with one or more techniques of this disclosure, that there is no infection, then the likelihood (e.g., probability) of there being no infection may then be determined to be relatively high. Consider an illustrative example involving 1,000 CIED patients with TYRX™ and 1,000 CIED patients without TYRX™, where the prevalence of infections in the TYRX™ group is 10% and the prevalence of infections in the non-TYRX™ group is 20%. Using an algorithm with [90, 90] sensitivity specificity for the TYRX™ group and [95, 85]sensitivity specificity for the non-TYRX™ groups yields a similar net present value (NPV) of ~99% for both groups.

The literature suggests that a first-time implant has infection rate under 1% while a change out of an IMD is up to 7%. Similar to having different sensitivity vs. specificity tradeoffs mentioned above for TYRX™ vs. non-TYRX™, different operating thresholds may be used for first-time vs. repeat implants.

In addition, the imaging program may include a sensitivity level that is based on a type of IMD. In some examples, medical device(s) 17 (e.g., IMD 6) may include a CIED. In addition, the CIED may be an ICD implant, whereas in other cases, the CIED may be a pacemaker implant. In such instances, processing circuitry 20 may employ a detection algorithm that has a higher sensitivity level compared to that of a sensitivity level used for a pacemaker implants. In some examples, sensitivity levels may include biasing factors or correction factors that, for example, processing circuitry 20 may apply when deploying a detection algorithm or in some instances, may apply to a result of an abnormality detection algorithm. In such examples, processing circuitry 20 may apply a particular sensitivity level, based on various factors that processing circuitry 20 identifies from system 100 and/or system 300, such that processing circuitry 20 may provide particular outcomes (e.g., more or less conservative outcomes) with respect to false positives, false negatives, true positives, true negatives, etc.

In an illustrative example, processing circuitry 20 may determine a sensitivity level for the imaging program (e.g., abnormality detection algorithms, etc.). To determine the sensitivity level, processing circuitry 20 may determine medical device information (e.g., IMD information) with respect to medical device(s) 17, physiological parameters (e.g., ECG), etc. In such examples, processing circuitry 20 may determine the sensitivity level based on the determined medical device information, physiological parameters, etc. In an illustrative and non-limiting example, processing circuitry 20 may determine a prevalence factor that defines the prevalence of abnormalities (e.g., infections) for a particular type of IMD. In another example, processing circuitry 20 may determine an impact factor that defines the impact an abnormality (e.g., device malfunction, infection, etc.) may have with respect to patient 4 and medical device(s) 17 (e.g., IMD 6). Processing circuitry 20 may determine, from such information or other information, a sensitivity level that yields a more conservative algorithm that errs on the side of over detection, rather than under detection, of abnormalities. That is, it may be important to be more conservative and not miss a potential abnormality (e.g., infection, malfunction of an IMD, etc.) because doing so may then provide high-energy life-saving therapy. In one example, an IMD may malfunction to a point where it is unable to determine temperature or migration data of an IMD, such that when a potential abnormality is detected from an image, processing circuitry 20 may determine not to rely on data received from IMD in order to identify, according to an adjusted sensitivity level, a likelihood of the abnormality being an actual abnormality. In one further example, processing circuitry 20 may determine a higher (e.g., more conservative) sensitivity level relative to other less conservative sensitivity levels, when processing circuitry 20 determines, for example, that a stimulation generator (not shown) and leads (not shown) are from different manufacturers but are being combined into a single IMD 6. That is, the likelihood of a potential abnormality may be higher in such instances where different items are being combined from different manufacturers into a single device, and thus, processing circuitry 20 may adjust the sensitivity level so as to be a higher sensitivity level in such instances.

In some examples, processing circuitry 20 may adjust the sensitivity level (e.g., a built-in calculation bias) for identifying particular abnormalities based on a duration of time IMD 6 has been implanted. This is because certain abnormalities (e.g., pocket infections) may be most common during, for example, the first year post-implant, and as such, a higher sensitivity level may be utilized during the particular timeframe (e.g., the first year) and/or a lower sensitivity level may be utilized during another time frame (e.g., after the first year).

In another example, medical device(s) 17 (e.g., IMD 6) may include a LINQ™ ICM. In such instances, processing circuitry 20 may employ a detection algorithm that has a different sensitivity level for the LINQ™ ICM compared to that of a sensitivity level used for other medical device(s) 17 (e.g., a pacemaker implant). That is, the detection algorithm may employ a particular sensitivity level where the medical device information indicates that the medical device was implanted as part of a particular type of procedure (e.g., an out-patient procedure). In addition, processing circuitry 20 may determine from the IMD information that a schedule for virtual check-ins, or other types of check-ins, are scheduled at a particular interval (e.g., regular intervals, irregular intervals, frequent intervals, infrequent intervals, etc.). In another example, processing circuitry 20 may determine a frequency by which the virtual monitoring service is receiving and/or monitoring medical device diagnostics, such as diagnostics from medical device(s) 17 (e.g., IMD 6, wearable heart rate and/or activity monitor, etc.).

In an illustrative and non-limiting example, processing circuitry, e.g., processing circuitry 20 of computing device(s) 2, processing circuitry 64 of edge device(s) 12, processing circuitry 98 of server(s) 94, or processing circuitry 40 of medical device(s) 17, may employ a first sensitivity level when determining an abnormality for a first type of implant (e.g., a pacemaker implant), whereas the processing circuitry may employ a second sensitivity level when determining an abnormality for a second type of implant (e.g., an ICM). In an example, the first sensitivity level may be higher than the second sensitivity level because processing circuitry 20 may have determined that the implant procedure of a second type of implant was out-of-office or out-patient, that there are one or more regularly-scheduled patient follow-ups via system 100 and/or system 300, and that processing circuitry 20 is continuously, or at least semi-continuously, monitoring diagnostic device data of a medical device, such as would results from regular data transmissions from medical device(s) 17 to computing device(s) 2 and/or to other devices (e.g., edge device(s) 12, etc.) of system 300.

In some examples, AI engine(s) and/or ML model(s), e.g., AI engine(s) 28 of computing device(s) 2, AI engine(s) 44 of medical device(s) 17, ML model(s) 30 of computing device(s) 2, or ML model(s) 46 of medical device(s) 17, may determine the sensitivity level based on training of the AI engine(s) and/or ML model(s). In an example, in order to determine sensitivity levels, processing circuitry, e.g., processing circuitry 20 of computing device(s) 2, processing circuitry 64 of edge device(s) 12, processing circuitry 98 of server(s) 94, or processing circuitry 40 of medical device(s) 17, may train the AI engine(s) and/or ML model(s) on data sets, including prevalence data (e.g., rate of infection with particular types of medical device(s) 17), severity data, data on likelihood of abnormalities, potential or actual impacts of particular types of abnormality (e.g., device malfunction and infection abnormalities, etc.), IMD information (e.g., device manufacturing information, implantation procedure information), etc. Upon being trained on such data, the AI engine(s) and/or ML model(s) may determine a sensitivity level that corresponds to each individual monitoring event (e.g., device contexts) or class of monitoring events of patient 4.

Advantages of applying such sensitivity levels include allowing monitoring system 100 to efficiently allocate processing, memory, and/or power resources, by scaling the sensitivity level according to individual needs. In addition, the sensitivity level may govern a rate at which computing device(s) 2 receive data from other devices (e.g., frame rates, transmission rates, etc.). In this way, computing device(s) 2 may receive more data, for example, in situations involving a higher likelihood of an abnormality being present, and receive less data in other situations. This selective use of sensitivity levels may also assist with bandwidth considerations, such as by limiting an amount of communication data that may otherwise consume a large amount of bandwidth of system 100 and/or system 300.

In some examples, the imaging program, including AI engine(s) 28 and/or ML models(s) 30 may be trained on several images/videos that have been labeled as corresponding to an abnormality or not (e.g., infection or not). In such examples, processing circuitry 20 may include an imaging program executed by AI engine(s) 28 and/or ML model(s) 30. AI engine(s) 28 and/or ML model(s) 30 may be trained with data that has been labeled based on improvement of an implantation site. In an example, AI engine(s) 28 and/or ML model(s) 30 can detect, as an implant status, implantation site "improvement" or implantation site "non-improvement" over time.

In some examples, processing circuitry 20 may acquire images of implantation site from multiple sessions over time after the implantation. Processing circuitry 20, via the imaging program, may chronologically analyze the time-aging of the implantation site with different thresholds to detect improvement or non-improvement of the implantation site. The prescribing physician can use the system to only follow-up on patients whose implantation site does not show signs of healing. In some examples, processing circuitry 20 may operate according to a time-lapse mode (e.g., as a supplemental image capture mode or as a process separate from a supplemental image capture mode).

During a time-lapse mode, processing circuitry 20 may, for example, collect images chronologically (e.g., on a daily schedule) and stitch them together over, e.g., a 2-12 week period post implant. This will allow for a time-sequence presentation of the images (e.g., including imaging sequences and still-images as part of the time-sequence) and time-sequence analysis.

In some examples, processing circuitry, e.g., processing circuitry 20 of computing device(s) 2, processing circuitry 64 of edge device(s) 12, processing circuitry 98 of data server(s) 94, or processing circuitry 40 of medical device(s) 17 may train AI engine(s) 28 and/or ML model(s) 30 on historical image captures and imaging sequence (e.g., video) captures. In an example, processing circuitry 20 may train AI engine(s) 28 and/or ML model(s) 30 on a rate of change of implantation site healing (e.g., infection spread or growth). The rate of change may indicate how quickly or slowly an implantation site is healing based on an analysis of successive image captures.

In some examples, rather than assess the implantation site directly (e.g., from a still-image of the implantation site), AI engine(s) 28 and/or ML model(s) 30 may instead analyze the progression of the implantation site healing (e.g., a delta between registered and superimposed successive images that track differences between the images over a multiweek period). In an example, AI engine(s) 28 and/or ML model(s) 30 may analyze a rate of change between an image captured on day X and an image captured on a previous day to determine a difference (e.g., a rate of change) between the images captured on successive days, and based on the difference, determine, from the image captured on day X, the presence of an abnormality at the implantation site.

In some instances, AI engine(s) 28 and/or ML model(s) 30 may track differences between still-images and images from imaging sequences (e.g. video sequences) in order to determine a delta at the implantation site over time (e.g., a delta between healing of the implantation site over time). Processing circuitry 20 may then determine abnormalities based on an analysis of difference(s) at the implantation site as imaged over time (e.g., an analysis of a first difference between a first image and a second image, an analysis of a second difference between the second image and a third image, an analysis of the first difference and the second difference, an analysis of a third difference between the first image and the third image, etc.). In an illustrative example, where processing circuitry 20, via AI engine(s) 28 and/or ML model(s) 30, determines the rate of change between a first, second, and/or third image falls below one or more predefined rate-of-change thresholds, processing circuitry 20 may determine the presence of a potential abnormality based on the delta between the plurality of images and the one or more predefined rate-of-change thresholds.

In some examples, processing circuitry 20 may determine, based on the images, the presence of a potential abnormality (1816). In one example, the backend system may route the various images to a computing device 2 of an expert technician trained in identifying abnormalities from images of implantation sites. In another example, the backend system may route the various images to a second one of computing device(s) 2 that has a particular configuration of AI engine(s) 28 and/or ML model(s) 46 trained in identifying abnormalities from implantation-site images. In some examples, when identifying the abnormality, processing circuitry 20 may determine, based on an image of the implantation site (e.g., the captured image(s) of the implantation site), a likelihood of the abnormality (e.g., a severity of the abnormality). In some instances, processing circuitry 20 may deploy a probability model to determine the likelihood of the abnormality. In one example, processing circuitry 20 may determine a potential severity of the potential abnormality based on an analysis of the captured image(s). In some examples, processing circuitry 20 may trigger a supplemental image capture mode based on the abnormality, such as based on a severity of the abnormality. In such examples, processing circuitry 20 may further identify the abnormality from supplemental images captured during the supplemental image capture mode.

In some examples, processing circuitry 20 may output a summary of the implant status, including potential abnormality information (1818). In one example, the backend system may transmit a report back to the first one of computing device(s) 2 indicating a result of the image analysis performed by the backend system. In an illustrative example, processing circuitry 20 may generate, based on the likelihood of the abnormality, a summary report identifying the abnormality, where the summary may include information regarding a determined potential infection. In some examples, processing circuitry 20 may store all image data and labels (e.g., expert labels) in a database and computation system to continuously improve and deploy the automated abnormality detection system (e.g., AI engine(s) 28 and/or ML model(s) 30). In any case, processing circuitry 20 may output the summary report. In some examples, the summary report includes at least a subset of the one or more frames of the image data. In some instances, the subset of the one or more frames may be derived from an imaging sequence (e.g., video capture) or other supplemental images that processing circuitry 20 obtains during a supplemental image capture mode. In such examples, processing circuitry 20 may generate a summary report including all or less than all of the one or more frames of the image data, where that image data was received prior to the abnormality determination and used at least in part to determine the abnormality. In some instances, the subset includes the frames that correspond to the perspective views in which the potential abnormality was identified (e.g., left lateral vs. right lateral). In some examples, if infection presence is not detected in any of the images with a high likelihood and for some images the detection is uncertain, processing circuitry 20 may output all the images from that session for human expert review.

In some examples, computing device(s) 2 may determine, from the imaging program, whether to configure the site-check process to include a pass-thru mode, where patient 4 does not need to come in for a consultation (e.g., for a post-implantation infection consultation). In such examples, computing device(s) 2 may provide the HCP with access to the various images (e.g., imaging sequences). As such, the HCP may, in some examples, decide whether the implantation site is healing as expected or whether an in-person follow-up is warranted.

In some examples, a HCP may have programmed and transmitted the imaging program to an application database (e.g., a program datastore). In another example, a HCP may have uploaded the imaging program directly to computing device(s) 2. That is, computing device(s) 2 may access the imaging program from an application database. In some instances, the imaging program may include a base imaging program (e.g., a common algorithm base) that may, when launched or before being launch, in different ways. In one example, processing circuitry 20 may tailor the base imaging program to produce an imaging program unique to patient 4, for example. The HCP may configure the imaging program to function in the pass-thru mode where the patient may forego the post-implant consultation entirely until execution of the imaging program results in an identified potential abnormality, such as one that satisfies a predefined threshold, that then warrants an in-person visit. In such examples, the HCP may, in any case, access the images in order to determine whether an abnormality is present, regardless of whether processing circuitry 20 determines the presence of a potential abnormality. In this way, the HCP (e.g., a physician, nurse, etc.) may independently adjudicate the images, series of images, and/or imaging sequences, independent of an automated image analysis of the imaging program, in order to independently determine a status of the implant, including an implantation site healing status.

In some examples, the images, series of images, and/or imaging sequences, may be adjudicated by a teledermatology service. In such instances, the teledermatology service may be configured to generate a report (e.g., a summary report) based on the images, series of images, and/or imaging sequences. In addition, computing device(s) 2 may receive the report from the teledermatology service and provide, via UI 22, the report for review. In such examples, computing device(s) 2 may interface with the teledermatology service via network 10 and/or via an intermediary, such as via one of edge device(s) 12. As described herein, edge device(s) 2 may include one of computing device(s) 2, where the computing device 2 is configured to interface with and/or operate the teledermatology service in order to generate, based on the various images, a summary report for output.

In some instances, processing circuitry, e.g., processing circuitry 20 of computing device(s) 2, processing circuitry 64 of edge device(s) 12, processing circuitry 98 of server(s) 94, or processing circuitry 40 of medical device(s) 17, may generate a summary report that matches a proficiency level of a user. In one example, processing circuitry 20 may identify a particular proficiency level of a user and generate a summary report for the user in accordance with the proficiency level. The proficiency level, in this instance, may represent the proficiency of a user in reviewing reports, such as teledermatology reports. Processing circuitry 20 may determine this proficiency level automatically from user data and/or may receive user input indicating this proficiency level, such as by requesting such information from the user via a questionnaire or other input mechanism.

In an illustrative example, processing circuitry 20 may receive a single report data file. Processing circuitry 20 may then transform the data of the data file in order to generate a user-facing summary report. Processing circuitry 20 may transform the data differently, for example, when processing circuitry 20 determines the report is being presented to a "novice" user (e.g., an elderly patient taking photos themselves) as compared to being presented to another use, such as an "expert" user (e.g., particular HCPs, nursing home workers, etc.). The summary report may include results of a HCP adjudication of the images and/or the results of the automated image analysis of the imaging program.

FIG. 19 is a flowchart illustrating an example method of performing a site-check process including an image capture process, in accordance with one or more techniques of this disclosure. In an example, processing circuitry 20 may receive indication to start a site check session (1920). In addition, processing circuitry 20 may initiate a camera 32, where initiating camera 32 comprises ensuring the camera 32 is able to capture the implantation site. That is, processing circuitry 20 may determine, from the at least one initial frame whether camera 32 is pointed at the implantation site (1926). In such instances, prior to receiving a first frame for analysis, processing circuitry may receive at least one initial frame (e.g., a test frame) of the one or more frames of the image data. At the start of the imaging session, processing circuitry 20 may determine whether the camera is pointed at the implantation site (e.g., the wound site). In a non-limiting example, processing circuitry 20 may, deploy a ML model (e.g., a DL model) that detects scars/wounds. In another example, processing circuitry 20 may, deploy a ML model (e.g., a DL model) that creates and compares wound-site markers for each patient. That is, processing circuitry 20 or another device may store patient-specific markers to a database, such that processing circuitry 20 may authenticate patient 4 based on patient-specific characteristics of the implantation site, and in addition, processing circuitry 20 may determine whether camera 32 is directed toward the implantation site, such that the implantation site is framed within a FOV of camera 32.

If processing circuitry 20 determines that camera 32 is not capturing the implantation site, such that the capture satisfies an imaging threshold, processing circuitry 20 may provide feedback, via UI 22, for adjustment of camera 32 (1924). That is, computing device(s) 2 may provide feedback to the user for adjusting the smartphone/tablet camera position. In doing so, processing circuitry 20 may determine, from the at least one initial frame (e.g., a test frame), a target adjustment of the imaging device. The target adjustment may include directional instructions for the user to adjust camera 32 in a particular way. As such, processing circuitry 20 may prompt the user, via UI 22, to adjust a position of camera 32 according to the target adjustment. In some examples, processing circuitry 20 may prompt the user, via UI 22, to adjust the position of camera 32 by signaling to the user a direction in which to position the imaging device in order to frame the implantation site for capture.

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may initiate a counter for tracking a quantity of images obtained (1928). The counter is used to track if all views of the implantation site have been taken. As described with reference to FIG. 20, the multiple views can include anterior, superior, inferior, right and left lateral. In addition, processing circuitry 20 may determine to capture one or more of the multiple views at two or more zoom levels (e.g., 1.0× and 2.0×, 1.0× and 1.5×, etc.).

FIG. 20 is an example illustration 2018 of a plurality of perspective views of an example implantation site, in accordance with one or more techniques of this disclosure. As described herein, computing device(s) 2 may provide, via UI 22, an interface (e.g., a graphical user interface) configured to guide the user in capturing images at different angles. In any case, computing device(s) 2 may be configured to provide a guide the user to take pictures at different angles to get multiple views of the implantation site of IMD 6 (e.g., wound site). FIG. 20 shows an example set of views (e.g., example of different views of the wound site).

The plurality of views may include an anterior view 2010, a left lateral 2020, a right lateral view 2030, a superior view 2040, and/or an inferior view 2050. In some examples, each view may be captured at a plurality of zoom levels. In a non-limiting example, each view may each be captured at two zoom levels. Zoom levels may be automatic or manual. In some examples, the zoom levels may include a 2× zoom, a 1.5× zoom, a variable zoom determined by AI engine(s) 28 and/or ML model(s) 30, etc.

In some instances, processing circuitry, e.g., processing circuitry 20 of computing device(s) 2, processing circuitry 64 of edge device(s) 12, processing circuitry 98 of server(s) 94, or processing circuitry 40 of medical device(s) 17, may provide a guide for capturing the perspective views. In an example, processing circuitry 20 may provide an augmented overlay of a reference marker, such as one visible to a user in this instance, that guides the user in aligning camera 32 with each perspective views. In some instances, processing circuitry 20 may cause computing device 2 to provide tactile feedback that guides the user, as well. In one example, computing device 2 may vibrate when camera 32 is aligned with a particular view. In another example, computing device 2 may provide audible feedback to guide the user in adjusting camera 32 to capture a particular perspective view.

Returning to FIG. 19, processing circuitry, e.g., processing circuitry 20 of computing device(s) 2, processing circuitry 64 of edge device(s) 12, processing circuitry 98 of server(s) 94, or processing circuitry 40 of medical device(s) 17, may perform an image capture process for a particular view (1930). In an example, processing circuitry 20 may determine an image quality of a captured image, adjust zoom levels, etc. Once processing circuitry 20 receives frames representing the particular view, processing circuitry 20 may increment the view counter (1932). Processing circuitry 20 may then determine whether all views have been captured (1934). In an example, processing circuitry 20 may determine a particular quantity of views that the imaging program will analyze for a potential abnormality. In a non-limiting example, the quantity of views includes five views, as described herein, and in some instances, five views at various zoom levels. Processing circuitry 20 may, in some examples, determine from a view counter whether processing circuitry has images representing all or if not, whether to change views (1936). In some examples, processing circuitry 20 may track the progress of the image capture in other ways, rather than a view counter, such as by labeling each view (e.g., with metadata), and determining which views, if any, are missing from the pool of images.

When processing circuitry 20 determine that the images represent all expected views, processing circuitry 20 may output the images for further analysis (1936). In some instances, processing circuitry 20 may output the images incrementally after capturing each view, rather than waiting to output the image as a single. Optionally, processing circuitry 20 may determine the potential abnormality information from the images representing some or all of the expected views (1938). In such instances, processing circuitry 20 may further output the potential infection information for further analysis and/or in order to trigger a supplemental image mode (1936).

In an illustrative example, processing circuitry 20 may receive a plurality of frames of image data, including at least one first frame and at least one second frame. The first frame may be relative to a first perspective view of the implantation site (e.g., anterior) and the second frame may be relative to a second perspective view of the implantation site (e.g., superior). That is, the first perspective view and the second perspective view may differ from one another. Processing circuitry 20 may determine, from the at least one first frame, a view of the implantation site that is depicted by the at least one frame. In this example, processing circuitry 20 may receive the second frame after receiving the first frame. In some examples, processing circuitry 20 may, when identifying the abnormality, and subsequent to receiving the first frame, identify, from the second frame of the image data, an abnormality at the implantation site corresponding to the second view. In such examples, processing circuitry 20 may determine that no abnormality is present in the first frame or that any potential abnormality detected is likely not a real abnormality. In such examples, processing circuitry 20 may trigger the supplemental capture mode upon determining a potential abnormality corresponding to the second view of the implantation site, such as a potential abnormality that satisfies a predefined likelihood threshold. In some examples, processing circuitry 20 may receive the one or more supplemental images of the implantation site relative to the second view.

In some examples, processing circuitry 20 may receive the one or more supplemental images of the implantation site by determining a view of the implantation site that is depicted by the at least one first or second frame. In an example, processing circuitry 20 may determine the view of the implantation site corresponding to the second frame is of the superior perspective view of the implantation site. As such, processing circuitry 20 may determine to capture supplemental images of the superior perspective view. In such instances, processing circuitry 20 may trigger the supplemental capture mode when processing circuitry 20 detects a frame corresponding to the particular view (e.g., the superior perspective view). Processing circuitry 20 may determine what view is represented by one or more frames by using reference markers, accelerometer data of computing device(s) 2, and/or by deploying AI engine(s) 28 and/or ML models(s) 30 to track various views of the implantation site and learn to identify various perspective views via image training over time. That is, processing circuitry 20 may identify the one or more supplemental images based at least in part on a view represented by the at least one frame. In an illustrative example, computing device(s) 2 may guide the user to angle camera 32 differently with respect to a perspective viewing angle (e.g., superior view) in order to capture different perspectives of substantially the same perspective viewing angle (e.g., superior view). In another example, the supplemental images may include images derived from a high resolution video, where the supplemental images are captured from the imaging sequence with reference to frames of the imaging sequence that processing circuitry 20 determines correspond to particular views (e.g., 3 degrees off center to the right relative to the superior view, X degrees off center to the right relative to the superior view, etc.).

In some example, processing circuitry 20 may automatically trigger the supplemental image capture mode in response to identifying an abnormality in a second frame captured subsequent to a first frame representing a particular view of the implantation site. In some examples, processing circuitry 20 may receive, via the imaging device, each perspective view of the plurality of perspective views, where each view comprises a plurality of zoom levels. In some instances, processing circuitry 20 may cause camera 32 to adjust zoom levels automatically for each perspective view. In another example, processing circuitry 20 may, via UI 22, prompt a user to adjust a zoom level relative to a particular perspective view.

In some examples, processing circuitry 20 may determine a likelihood that a potential abnormality is an actual abnormality by identifying the potential abnormality in a plurality of perspective views, wherein at least one frame represents a particular perspective view of the plurality of perspective views. Processing circuitry 20 may then determine, for each perspective view in which the potential abnormality is identified, a confidence interval for the identification of the abnormality. In some examples, the confidence interval corresponds to the confidence the system has that the identification of the potential abnormality in each respective perspective views is accurate. Processing circuitry 20 may then determine, according to the confidence interval, a number of perspective views of the plurality of perspective views for which the determined confidence interval satisfies a criterion. In such examples, processing circuitry 20 may determine, based at least in part on the determined number of perspective views, the likelihood of the abnormality. That is, computing device(s) 2 may determine a number of perspective views of the plurality of perspective views in which the potential abnormality is identified as comprising a particular confidence interval.

As described herein, images (e.g., photos) of the implantation site (e.g., a wound site) can be analyzed either on the interrogating device (e.g., computing device(s) 2) or on a backend system (e.g., Medtronic CareLink® Network). To illustrate, app-based smartphones have on-board display and computational capabilities, and the interrogated data can be (i) presented for manual analysis on the app and (ii) be processed on the app for automated analysis. An advantage of an app-based analysis platform is that it need not be connected to a communication infrastructure such as Wi-Fi™/4G (which can be challenging in hospital environments) for the analysis. Advantageously, processing circuitry 20 may store the device interrogation and analysis results to internal storage (e.g., memory corresponding to a mobile device app) for later synchronization with network 10, such as Medtronic CareLink® Network. In some examples, computing device(s) 2 may synchronize this information for subsequent retrieval and analysis.

While app-based computation and analysis is advantageous in an in-hospital setting, transmitting image data, via network 10, for remote analysis may be advantageous in a more remote setting. For instance, for regular site-checks/check-ins, computing device(s) 2 may transmit, via communication circuitry 26, the acquired image(s), imaging sequences, and/or preliminary abnormality analysis results, to a server(s) 94 (e.g., a CareLink® device) for remote analysis and viewing. In any case, the physician/caregiver can perform regular remote follow-ups and exception-based monitoring without the patient having to come in physically to the clinic.

In addition to acting as an analysis platforms, both a mobile app executing the imaging program and the cloud may include the ability for approved users (e.g., clinicians, device nurses, monitoring center device technicians, etc.), to input the result of their analysis. In such instances, the processing circuitry may not allow monitoring center customer service reps to input results of an analysis. This is because input from approved users can be used as the "ground truth" to further develop ML models and/or AI algorithms. In this way, processing circuitry 20 may determine that such user input corresponds to a particular level of authority that before allowing the user input to serve as training data for an image processing algorithms (e.g., AI engine(s) 28 and/or ML model(s) 30). In other words, processing circuitry 20 may train AI engine(s) 28 and/or ML model(s) 30 on data accepted only from specifically approved sources.

FIG. 21 is a flowchart illustrating an example method of performing an image capture process 2130, such as the image capture process of FIG. 19, in accordance with one or more techniques of this disclosure. That is, processing circuitry, e.g., processing circuitry 20 of computing device(s) 2, processing circuitry 64 of edge device(s) 12, processing circuitry 98 of server(s) 94, or processing circuitry 40 of medical device(s) 17, may perform one or more of the techniques of FIG. 21, when performing the image capture process (1930) of FIG. 19. The imaging program may identify images with high sensitivity. If the imaging program detects a potential abnormality from a specific view, the imaging program can guide the user (e.g., via UI 22) to capture additional images around the same view. In another example, the imaging program may automatically initiate a high-sample rate video around that view. The objective is to get any image with the imaging program that can show a potential abnormality. In some examples, the tradeoff may include a high false positive rate (e.g., low specificity) from a portion of the imaging program executing on computing device(s) 2, but in accordance with one or more of the various techniques of this disclosure, the processing circuitry system may alleviate this concern by performing additional backend analysis, as described herein.

To illustrate, processing circuitry 20 may initiate, for a particular view, the image capture process (2132). In doing so, processing circuitry 20 may cause camera 32 to image the implantation site, via the imaging program. That is, camera 32 may output frames of image data for preview display. Processing circuitry 20 may then determine the image quality of the image capture (2134). Processing circuitry 20 may do so in order to ensure the image quality satisfies a particular threshold (2136). If not, processing circuitry 20 provides feedback, via UI 22, to the user for adjusting a position of camera 32 (2138). In any case, processing circuitry 20 may, via the imaging program, continuously check if the image quality is good (e.g., not blurred, adequate lighting, etc.) (2136). Processing circuitry 20 may, via the imaging program, provide an analysis that uses the CCD chip on computing device(s) 2 with spectral response analysis mode. That is, processing circuitry 20 may initiate a flash device of camera 32 to serve as an excitation (e.g., white light) light source. In this way, processing circuitry 20 may perform separate color filtering analysis in different light wavelength to detect redness and swelling in different skin tones, as potential abnormalities. In some instances, redness or swelling may indicate a potential infection as the potential abnormality. In another example, the potential abnormality may include healing granulation around edges of an implantation site, discharge from an implantation site, inflammation at the implantation site, tissue erosion at or around the implantation site, etc. As described herein, processing circuitry 20 may provide, via UI 22, reminders for patient 4 to take regularly, or in some instances, irregularly intervaled images (e.g., daily pictures, systematically scheduled pictures). In this way, processing circuitry 20 may strategically capture images of the implantation-site progression over time.

In some examples, processing circuitry 20 may adjust the zoom level or prompt the user, via UI 22, to adjust the zoom level (2140). In some instances, processing circuitry 20 may provide, via UI 22, a zoom-in and out guide that assists the user in capturing images of the implantation site at different zoom levels.

Once a clear image at the particular zoom level is detected, processing circuitry 20 may cause camera 32 to capture the image. Processing circuitry 20 may, in some instances, wait until receiving a user input command to capture the image (2142). In one example, this process is continued until all the prescribed views of the implantation site are captured for analysis. As described herein, where processing circuitry 20 is sensitive to detecting potential abnormalities at the implantation site, processing circuitry 20 may detect a potential abnormality from a specific view (2144). In a non-limiting and illustrative example, processing circuitry 20 may automatically capture a high-sampling rate video around that view for additional review data. In some instances, processing circuitry 20 may perform all image capture and supplemental image capture automatically without input from a user via UI 22. That is, user may point camera 32 at the implantation site and rotate camera 32 around the implantation site. Substantially hidden from the user, processing circuitry 20 may automatically initiate captures of images when processing circuitry 20 determines a particular view is present and may automatically initiate a supplemental image capture mode, such as a video capture mode.

In some examples, upon determining a potential infection, processing circuitry, e.g., processing circuitry 20 of computing device(s) 2, processing circuitry 64 of edge device(s) 12, processing circuitry 98 of server(s) 94, or processing circuitry 40 of medical device(s) 17, may guide additional image capture for the particular view (2150). In an example, processing circuitry 20 may cause computing device 2 to provide tactile feedback to the user. In addition, processing circuitry 20 may perform blur-detection and lighting-level detection. Processing circuitry 20 may further utilize results of such detections in order to guide the user in capturing images when the image is clear with adequate lighting. As described, processing circuitry 20 may provide feedback, via on-app messages or vibration-based tactile feedback, configured to guide patients throughout the imaging process. Optionally, processing circuitry 20 may, upon receiving the additional capture (e.g., supplemental image data), increment a view counter (2146). In any case, processing circuitry 20 may end imaging program or change to capturing a next view (2148).

In some examples, processing circuitry 20 may provide manual and/or automatic video capture of the implantation site, where processing circuitry 20 or other processing circuitry may process the video to identify potentially relevant frames of the image data and supplemental image data, and/or to identify potential abnormalities from the frames. Processing circuitry 20 may determine the example process 2130 is complete once all views are obtained. As such, processing circuitry 20 may output results of the imaging process for storage and/or further analysis.

FIG. 22 is a flowchart illustrating an example method 2246 of utilizing imaging techniques, in accordance with one or more techniques of this disclosure. In some examples, the imaging device (e.g., camera 32) may be configured to operate in a first image capture mode. In addition, the imaging device (e.g., camera 32) may be configured to operate in a supplemental image capture mode. The first image capture mode and the supplemental image capture mode may differ from one another. As such, processing circuitry 20 may receive, via the imaging device operating in the first image capture mode, at least one first frame. In a non-limiting and illustrative example, processing circuitry 20 may detect a potential infection, or another potential abnormality, in a particular view represented by the at least one first frame (2248).

Processing circuitry 20 may automatically initiate a high resolution video as the supplemental image capture mode (2250). Alternatively, the supplemental image capture mode may include altering a camera parameter, such as a contrast level or a 3A parameter. In such examples, processing circuitry 20 may provide, via UI 22, a notification to the user that indicates the imaging device is transitioning from the first image capture mode to the supplemental image capture mode.

Processing circuitry 20 may receive, via the imaging device operating in the supplemental image capture mode, the one or more supplemental images of the implantation site. In this illustrative example, processing circuitry 20 may receive frames of high resolution video data (2252). In another example, processing circuitry 20, when entering the supplemental image capture mode, may prompt the user for additional still images for the particular view where processing circuitry 20 observed the potential abnormality. In some examples, processing circuitry 20 may prompt the user for the additional still images in the current session or in some instances, may prompt the user for the additional still images in another session (e.g., a site-check session scheduled for a next day or week).

Subsequent to receiving the one or more supplemental images of the implantation site, processing circuitry 20 may determine to revert to the first image capture mode. That is, processing circuitry 20 may determine that a supplemental image capture session has timed-out causing processing circuitry 20 to stop the supplemental image capture mode. In such instances, processing circuitry 20 may revert to the first image capture mode. In an illustrative example, processing circuitry 20 may determine that a cease video capture event has occurred, and in response to the cease video capture event, stop the video capture mode. The cease video capture event may be based on processing circuitry 20 detected no abnormality in the supplemental image data or based on user input (e.g., actuation of a stop button).

In some examples, the supplemental image capture mode includes a video capture mode. In such examples, processing circuitry 20 may output one or more supplemental images of the implantation site as an imaging sequence. The imaging sequence may be based at least in part on the one or more supplemental images of the implantation site. In some examples, the one or more supplemental images comprise a first supplemental image. In such examples, the video sequence may be based on the at least one frame of the image data and the one or more supplemental images, where the one or more supplemental images comprise at least one frame of supplemental image data. In another example, the one or more supplemental images comprise a plurality of frames of supplemental image data, where the video sequence is based on the plurality of frames.

In some examples, computing device(s) 2 may output the imaging sequence as a video sequence, a video file, a compressed file, etc. In some examples, the imaging sequence may include augmented features, such as overlay objects or reference markers overlaid on the imaging sequence. In such instances, computing device(s) 2 may output the imaging sequence including the augmented features or may not include the augmented features, in other instances. In an illustrative and non-limiting example, the imaging sequence may include a compressed file that includes video data (e.g., encoded video data), augmentation features (e.g., reference marker overlays, color enhancement features, etc.). In some instances, the imaging sequence may include an uncompressed file. In any case, computing device(s) 2 may output the imaging sequence to storage device 24 or externally, via communication circuitry 26, to another computing device 2, edge device(s) 12, server(s) 94, medical device(s) 17 (e.g., a bedside monitor), etc., for further processing (e.g., performing an abnormality analysis).

In addition, the imaging sequence may include audio captured via audio circuitry of computing device(s) 2, such as audio of one or more users speaking during the capture. That is, the imaging sequence may include audio data (e.g., compressed audio data). Audio features may provide context to AI engine(s) 28 and/or ML model(s) 30, such that AI engine(s) 28 and/or ML model(s) 30 may learn from the audio how to best serve the user in capturing the images or imaging sequences. That is, the AI and/or ML model may learn from the audio and/or from studying movement relating to the imaging sequence, that a user has difficulty rotating in a particular direction (e.g., clockwise around an implantation site) to capture specific view. In such examples, computing device(s) 2 may modify the imaging program, based on the analysis of AI engine(s) 28 and/or ML model(s) 30, to better accommodate the user, such as by allowing rotation in a different direction (e.g., counterclockwise). In some examples, patient data or user data may indicate, for the analysis by AI engine(s) 28 and/or ML model(s) 30, that a user or patient 4 prefers using a right hand or left hand of the user or patient 4 in order to provide input to computing device(s) 2 (e.g., input images). AI engine(s) 28 and/or ML model(s) 30 may study (e.g., be trained on) such data, among other data inputs, in order to tailor the site-check process for the relevant user and/or in order to tailor the abnormality evaluation process to improve detection of the abnormality based on the particular way in which the images and imaging sequences were captured by the user.

In some examples, the audio may provide context for a user evaluating the imaging sequence. In an example, the imaging sequence may be transmitted, via communication circuitry 26, to another device, such as a computing device 2 of a HCP or a separate device that includes AI engine(s) 28 and/or ML model(s) 30. In this examples, the imaging sequence may include an audio portion. The HCP, if reviewing the imaging sequence, may be able to listen to the audio of patient 4 as that patient was conducting the virtual check-in. In any case, computing device(s) 2 may output the imaging sequence, where the imaging sequence is at least based in part on the one or more supplemental images of the implantation site.

In some examples, processing circuitry 20 and camera 32 may be configured to, in accordance with the video capture mode, produce the imaging sequence such that the imaging sequence satisfies a particular criterion (e.g., a video resolution parameter, a file size, etc.). In such examples, computing device(s) 2 may predefine one or more criteria, such as a video resolution parameter (e.g., a resolution criterion). In one example, a first video resolution criterion may be such that a video file is of a particularly high resolution (e.g., 115 frames per second, 120 frames per second, 125 frames per second, etc.). In other examples, the video resolution criterion may be of a substantially higher resolution relative to the first video resolution criterion (e.g., greater than 125 frames per second, etc.).

In some examples, the video resolution criterion may further include 30 frames per second, 60 frames per second, 120 frames per second, etc. In any case, processing circuitry 20 may determine the frame rate based on an identified probability of the abnormality as determined, for example, from a still-frame image. In an illustrative example, when processing circuitry 20 determines the probability of the abnormality to be low, then processing circuitry 20 may utilize a frame rate below a high resolution frame rate (e.g., 120 frames per second, 125 frames per second, etc.) in order to define operation of the supplemental image capture mode. When processing circuitry 20 determines the probability of the abnormality to satisfy a predefined threshold (e.g., greater than 50% chance of an infected wound site), then processing circuitry 20 may utilize, in order to define operation of the supplemental image capture mode, a higher resolution frame rate relative to the frame rate of the low likelihood determination (e.g., 120 frames per second, 125 frames per second, etc.). In another example, when processing circuitry 20 determines a confidence interval satisfies a predefined threshold (e.g., less than 50% confidence interval in accuracy of a detection of an abnormality from a particular still-image capture), then processing circuitry 20 may utilize, in order to define operation of the supplemental image capture mode, a higher resolution frame rate (e.g., 120 frames per second, 125 frames per second, etc.).

In addition, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine anew the criteria for the video capture mode. In one example, a resolution criterion may be based on a variable parameter that processing circuitry 20 determines based on circumstances of the video capture or other image captures (e.g., preceding image capture). In one example, processing circuitry 20 may determine a variable resolution criterion based on a determined likelihood of a potential abnormality (e.g., a potential infection) being an actual abnormality.

In an illustrative example, processing circuitry 20 may determine a video resolution parameter as a variable video resolution parameter. In such instances, processing circuitry 20 may automatically trigger the video capture mode by determining a confidence interval for the identification of the abnormality and determining, based on the confidence interval, a first value for the variable video resolution parameter. In some examples, processing circuitry 20 may determine a first value for a video resolution parameter (e.g., a frequency, sample rate, frame rate, etc.) by deploying AI engine(s) 28 and/or ML model(s) 30 to adjust the resolution parameter based on an assessment of a probability of infection from a first image. In one example, the resolution parameter may be a higher frame rate when the assessment yields a higher probability. On the other hand, the resolution parameter may be higher when the assessment yields a lower probability require a higher frame rate so that the AI engine(s) 28 and/or ML model(s) 30 can confirm that the probability is indeed low as originally assessed. In such examples, the first value of the variable video resolution parameter has a higher resolution value relative to a potential second value of the variable video resolution parameter. The potential second value may be a resolution of at least 120 frames per second.

In some examples, processing circuitry 20 may receive a frame representing a first perspective view. In receiving one or more supplemental images of the implantation site, processing circuitry 20 prompts a user, via UI 22, during the supplemental image capture mode, to adjust camera 32 to capture a second frame representing a second perspective view. In one example, processing circuitry 20 may prompt the user to rotate camera 32 to capture a second view of the implantation site. Processing circuitry 20 may identify, from the one or more supplemental images of the implantation site, the second frame representing the second perspective view. That is, processing circuitry 20 determine, from the video sequence, one or more frames that represent a high resolution view of the implantation site for the second perspective view.

In one example, processing circuitry 20 may do so by determining a reference marker (2254). The reference marker may be internal to the analysis of processing circuitry 20 (e.g., invisible to the user). As the user rotates camera 32, processing circuitry 20 may track the angle of camera 32 with respect to the reference marker, where processing circuitry 20 may fix the reference marker in virtual three-dimensional space. Processing circuitry 20 may use a reference marker to identify a target perspective view (e.g., a second perspective view) from frames of the supplemental image data (e.g., video data, burst shots, etc.) (2258). In such examples, the target perspective view may be offset from the first perspective view by 90 degrees. That is, processing circuitry 20 may capture the second frame when camera 32 has been rotated 90 degrees relative to the reference marker.

In an illustrative and non-limiting example, a user may rotate camera 32 around implantation site while video is being captured. Processing circuitry 20 may isolate a frame from the video that the processing circuitry 20 identifies as representing the second perspective view. Processing circuitry 20 may end the video capture automatically as soon as the second view is captured from the video sequence. In some examples, processing circuitry 20 may end the video capture due the video capture timing out, such as when the user is unable to rotate phone properly in order to adequately capture the second perspective view within a particular amount of time.

FIG. 23 is a UI visualization of an example complete check-in interface 1902, in accordance with one or more techniques of this disclosure. Complete check-in interface 1902 illustrates a UI that processing circuitry 20 may cause to be displayed upon completion of one or more of the virtual check-in processes (e.g., site-check process). In some instances, processing circuitry 20 may output the complete check-in interface 1902 after the information is submitted that is to be forwarded to the HCP/clinician, etc. FIG. 23 illustrates a UI that computing device(s) 2 may generate and present to indicate completion of the virtual check-in process corresponding to all of the four tiles shown in FIG. 7. As described herein, the complete check-in interface 1902 may only relate to site-check tile 712, where the site-check UIs are decoupled from the additional virtual check-in processes. Complete check-in interface 1902 may further include a graphical icon 1904 indicating completion of, for example, the site-check process.

In some examples, complete check-in interface 1902 may provide an option to schedule an in-person clinic follow-up. Processing circuitry 20 may cause this option to be presented, via UI 22, when a potential abnormality is detected or where processing circuitry 20 was unable to rule out an abnormality from an assessment of the camera images.

In addition, complete check-in interface 1902 may include a "generate report" icon 1906 and/or a "send report to clinic" icon 1908. The report may include, among other information, the images and/or imaging sequences captured by processing circuitry 20. In addition, the report may include a synthesis of data including criteria for failure based on severity of failure (e.g., criteria for finding an abnormality), number of failed tests, number of failed attempts, number of tiles failed, etc. In addition, processing circuitry 20 may generate the report based on a physician preference (e.g., type of report, specifics for data weighting, etc.). Processing circuitry 20 may, in addition, transmit the report based on a physician preference regarding notifications and/or notification frequency. Processing circuitry 20 may further synthesize the data based on characteristics of patient 4 and/or type of medical device 17 (e.g., IMD 6).

In an illustrative example, processing circuitry 20 may employ various abnormality scoring algorithms that are based on a severity of a potential abnormality detected in one or more images. The abnormality scoring algorithm may determine an abnormality score that maps to an actionable response (e.g., transmit report to HCP, automatically schedule clinician visit, etc.). Processing circuitry 20 may determine a sensitivity for an abnormality scoring algorithm, e.g., based on a severity of a potential abnormality detected in an image of a bodily site of patient 4 (e.g., an implantation site), based on IMD type, etc. The sensitivity may define a threshold that can range from a conservative threshold that causes a particular output (e.g., failure determination, transmit report to HCP, etc.) in response to a determination of any image indicating an abnormality. In another example, the sensitivity may define a complex threshold that utilizes a weighted composite score that, in a non-limiting example, factors the severity of the failure, along with the underlying algorithms that define the imaging program (whether failed or not), relative to any underlying medical conditions of patient 4, to determine if a failure is determined that warrants a particular response, e.g., based on a mapping of an abnormality score to particular response outputs. In addition, the sensitivity may further define a threshold that factors in physician programmable limits for medical device(s) 17.

In some examples, processing circuitry 20 may provide feedback to patient 4 through graphical simplified icons. In another example, processing circuitry 20 may obtain a preference from a HCP that indicates, rather than simplified icons, to provide complex results. In such instances, processing circuitry 20 may provide feedback to patient 4 as complex results.

FIG. 24 is a UI visualization of an example complete check-in interface 2002, in accordance with one or more techniques of this disclosure. In an example, complete check-in interface 2002 indicates a confirmation of receipt 2004, either by the HCP's office or by an intermediate system that is responsible for submission to the HCP's office. That is, processing circuitry 20 may receive confirmation from an intermediate system (e.g., edge device(s) 12) and in turn, may provide receipt confirmation 2004. Receipt confirmation 2004 may represent receipt of the report at the office of a HCP of patient 4. In another example, receipt confirmation 2004 may represent confirmation that the report has been saved successfully to a database (e.g., one of server(s) 94, a plurality of server(s) 94 comprising a cloud storage database, server(s) 94 and edge device(s) 12 comprising a cloud storage database, etc.). In such examples, authorized HCP may, via computing device 2 of the HCP, access the report from the database. In an illustrative example, receipt confirmation may further include uploading the summary report to an EMR database. As described herein, the techniques of this disclosure are applicable to both a "cloud" implementation (e.g., Medtronic CareLink® Network) and/or "edge" implementation (e.g., on a mobile app). As such, the report may be uploaded and stored in any number of different locations and accessed from those locations in any number of different ways.

FIG. 25 is a flowchart illustrating an example method of determining instructions for medical intervention concerning an IMD patient, in accordance with one or more techniques of this disclosure. In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may determine an implant condition status based on data received via UI 22 (2502). The implant condition status may include an indication that processing circuitry 20 has determined an abnormality at the implantation site of medical device(s) 17. In some examples, processing circuitry 20 may determine the implant condition status based on images and/or imaging sequences received via UI 22. Although described as being generally performed by computing device(s) 2, the example method of FIG. 25 may be performed by, e.g., any one or more of edge device(s) 12, medical device(s) 17, or server(s) 94, e.g., by the processing circuitry of any one or more of these devices.

Processing circuitry, e.g., processing circuitry 20 of computing device(s) 2, processing circuitry 64 of edge device(s) 12, processing circuitry 98 of server(s) 94, or processing circuitry 40 of medical device(s) 17, may determine instructions for medical intervention based on the implant condition status of patient 4 (2504). For example, where processing circuitry 20 determines the presence of an abnormality at the implantation site of one of medical device(s) 17, processing circuitry 20 may determine instructions for medical intervention based on the abnormality. In some examples, processing circuitry 20 may determine different instructions for different severity levels or abnormality categories. For example, processing circuitry 20 may determine a first set of instructions for one abnormality that processing circuitry 20 determines is likely less severe than another abnormality. In some examples, processing circuitry 20 may not determine intervention instructions where processing circuitry 20 determines that the abnormality level does not satisfy a predefined threshold. In some examples, processing circuitry 20 may provide an alert, such as a text- or graphics-based notification, a visual notification, etc. In some examples, processing circuitry 20 may cause an audible alarm to sound or cause a tactile alarm, alerting patient 4 of the determined abnormality. In other examples, computing device(s) 2 may provide a visual light indication, such as emitting a red light for high severity or a yellow light for medium severity. The alert may indicate a potential, possible or predicted abnormality event (e.g., a potential infection).

In some examples, processing circuitry, e.g., processing circuitry 20 of computing device(s) 2, processing circuitry 64 of edge device(s) 12, processing circuitry 98 of server(s) 94, or processing circuitry 40 of medical device(s) 17, may transmit the instructions for medical intervention to be display via a user interface, such as UI 22 (2506). In some examples, processing circuitry 20 may transmit the instructions to a device of a HCP (e.g., a caretaker), such as a pager of the HCP. In examples where processing circuitry 64 generates the instructions, processing circuitry 20 may transmit the instructions for medical intervention to a user interface. The instructions may include the abnormality indication. In some examples, edge device(s) 12, medical device(s) 17 (e.g., IMD 6), server(s) 94, and/or computing device(s) 2 may use the gathered data to predict adverse health events (e.g., worsening infections) using integrated diagnostic methods as described, for example, in U.S. Patent Application No. 62/906,991 by Sarkar et al., entitled "DETERMINING LIKELIHOOD OF AN ADVERSE HEALTH EVENT BASED ON VARIOUS PHYSIOLOGICAL DIAGNOSTIC STATES," filed on Sep. 27, 2019, and incorporated herein by reference in its entirety. That is, computing device(s) 2 may use the abnormality determination, including a likelihood or severity determination, as an evidence node of a probability model deployed, for example, by AI engine(s) 28 and/or ML model(s) 30, in order to determine a probability score indicating the likelihood that an implantation site of patient 4 is infected or is likely to become infected within a predetermined amount of time.

While described from the perspective of a user computing device 2 performing the techniques of this disclosure, it should be noted that the system of this disclosure supports bidirectional communication between a user (e.g., patient 4) and an HCP. The bidirectional communication may function using similar UIs on both ends of the communication line. In such examples, an HCP may, via computing device 2 of the HCP, access images uploaded by the user via computing device 2 of the user, physiological parameter data items, medical device information, patient information, etc. In addition, the HCP may, via computing device 2 of the HCP, determine the presence or absence of an abnormality from the data upload, and transmit a summary report back to computing device 2 of the user (e.g., patient 4), for example, including one or more indications of an abnormality.

Illustrative examples of the disclosure include:

Example 1: A method of monitoring an implantation site of a patient, the method comprising: determining, via a computing device, identification data for the patient; identifying, based at least in part on the identification data, IMD information that corresponds to an IMD of the patient; determining, based at least in part on the IMD information, an imaging program that defines one or more parameters for imaging the implantation site; initiating, by the computing device, an imaging device, the imaging device configured to capture, in accordance with the imaging program, one or more frames of image data; receiving, via the imaging device, at least one frame of the one or more frames, the at least one frame including an image of the implantation site; identifying, from the at least one frame of the image data, an abnormality at the implantation site; in response to identifying the abnormality, automatically triggering a supplemental image capture mode, wherein the imaging device, when operating in the supplemental image capture mode, is configured to capture one or more supplemental images of the implantation site; subsequent to triggering the supplemental image capture mode, receiving, by the computing device, the one or more supplemental images of the implantation site; and outputting, via the computing device, the one or more supplemental images of the implantation site.

Example 2: A method according to Example 1, wherein the abnormality at the implantation site includes one or more of: a potential infection at the implantation site or abnormal healing at the implantation site.

Example 3: A method according to Example 2, wherein identifying the abnormality comprises: determining, from the at least one frame, the presence of the potential infection at the implantation site; and determining, based at least in part on the at least one frame, a likelihood of an actual infection evidenced by the presence of an infectious agent at the implantation site.

Example 4: A method according to any of Examples 1 through 3, wherein initiating the imaging device comprises: prior to receiving the at least one frame, receiving at least one initial frame of the one or more frames of the image data; determining, from the at least one initial frame, a target adjustment of the imaging device; and prompting a user, via a user interface of the computing device, to adjust a position of the imaging device according to the target adjustment.

Example 5: A method according to any of Examples 1 through 4, wherein identifying the abnormality comprises: determining, based at least in part on the at least one frame, a likelihood of the abnormality; generating, based on the likelihood of the abnormality, a summary report identifying the abnormality; and outputting, via the computing device, the summary report.

Example 6: A method according to any of Examples 1 through 5, wherein determining the likelihood of the abnormality comprises: identifying the abnormality in a plurality of perspective views, wherein the at least one frame represents a particular perspective view of the plurality of perspective views; determining, for each perspective view in which the abnormality is identified, a confidence interval for the identification of the abnormality; determining, according to the confidence interval, a number of perspective views of the plurality of perspective views for which the determined confidence interval satisfies a criterion; and determining, based at least in part on the number of perspective views, the likelihood of the abnormality.

Example 7: A method according to Example 6, further comprising: receiving, via the imaging device, each perspective view of the plurality of perspective views as each comprising a plurality of zoom levels.

Example 8: A method according to any of Examples 1 through 7, wherein the at least one frame comprises a plurality of frames of the image data, and wherein receiving the plurality of frames of the image data comprises: receiving a first frame relative to a first perspective view of the implantation site; and subsequent to receiving the first frame, receiving a second frame relative to a second perspective view of the implantation site, wherein the first perspective view and the second perspective view differ from one another.

Example 9: A method according to Example 8, wherein identifying the abnormality comprises: subsequent to receiving the first frame, identifying, from the second frame of the image data, the abnormality at the implantation site.

Example 10: A method according to Example 9, wherein automatically triggering the supplemental image capture mode comprises: in response to identifying the abnormality in the second frame, automatically triggering the supplemental image capture mode.

Example 11: A method according to any of Examples 1 through 10, wherein the at least one frame comprises a first frame representing a first perspective view, wherein receiving the one or more supplemental images of the implantation site comprises: prompting a user, during the supplemental image capture mode, to adjust the imaging device to capture a second frame representing a second perspective view; and identifying, from the one or more supplemental images of the implantation site, the second frame representing the second perspective view.

Example 12: A method according to any of Examples 1 through 11, wherein receiving the one or more supplemental images of the implantation site comprises: determining, from the at least one frame, a view of the implantation site that is depicted by the at least one frame; and identifying the one or more supplemental images based at least in part on the view of the at least one frame.

Example 13: A method according to any of Examples 1 through 12, wherein determining the imaging program comprises: determining a proficiency level of a user, the proficiency level indicative of a proficiency of the user with imaging implantation sites of IMDs; determining, based on the proficiency level, an imaging mode; and capturing, according to the imaging mode, the at least one frame.

Example 14: A method according to any of Examples 1 through 13, wherein the supplemental image capture mode comprises a video capture mode, and wherein outputting the one or more supplemental images of the implantation site comprises: outputting, via the computing device, an imaging sequence, the imaging sequence based at least in part on the one or more supplemental images of the implantation site.

Example 15: A method according to Example 14, wherein the imaging device is configured to, in accordance with the video capture mode, produce the imaging sequence such that the imaging sequence satisfies a particular video resolution parameter.

Example 16: A method according to Example 15, wherein the particular video resolution parameter comprises a variable video resolution parameter, and wherein automatically triggering the video capture mode comprises: determining a confidence interval for the identification of the abnormality; and determining, based on the confidence interval, a first value for the variable video resolution parameter.

Example 17: A method according to Example 16, wherein the first value of the variable video resolution parameter comprises a higher resolution value relative to a potential second value of the variable video resolution parameter, wherein the potential second value comprises a resolution of at least 120 frames per second.

Example 18: A method according to any of Examples 1 through 17, wherein the imaging device is configured to operate in a first image capture mode, wherein the first image capture mode and the supplemental image capture mode differ from one another, and wherein the method further comprises: receiving, via the imaging device operating in the first image capture mode, the at least one frame; providing a notification that indicates the imaging device is transitioning from the first image capture mode to the supplemental image capture mode; receiving, via the imaging device operating in the supplemental image capture mode, the one or more supplemental images of the implantation site; and subsequent to receiving the one or more supplemental images of the implantation site, determining, by the computing device, to revert to the first image capture mode.

Example 19: A method according to any of Examples 1 through 18, wherein the identification data includes one or more of: biometric data, RFID data, NFC data, telemetry protocol data, user login information, authentication data, or a patient name.

Example 20: A method according to any of Examples 1 through 19, wherein determining the identification data for the patient comprises: receiving, by the computing device, authentication data identifying a user of the imaging program; authorizing the user to access the imaging program; subsequent to authorizing the user to access the imaging program, receiving, via the computing device, input data that identifies the patient of the IMD; and determining, from the input, the identification data for the patient.

Example 21: A method according to any of Examples 1 through 20, wherein the IMD information includes one or more of: IMD implantation site information, historical data relating to the implantation site of the IMD, historical data relating to the IMD, IMD type information, IMD communication protocol information, an estimated orientation of the IMD, data regarding one or more HCPs (e.g., surgeons, clinicians) responsible for implanting (e.g., inserting) the IMD, information relating to one or more methods employed by the one or more HCPs in order to seal the implantation site, or images of the implantation site.

Example 22: A method according to any of Examples 1 through 22, wherein the computing device comprises the imaging device.

Example 23: A system for monitoring an implantation site of a patient, the system comprising one or more means for performing the methods of any of Examples 1 through 22. For example, the system of Example 23 may include a memory configured to store image data; and one or more processors implemented in circuitry and configured to: determine identification data for the patient; identify, based at least in part on the identification data, IMD information that corresponds to an IMD of the patient; determine, based at least in part on the IMD information, an imaging program that defines one or more parameters for imaging the implantation site; initiate an imaging device, the imaging device configured to capture, in accordance with the imaging program, one or more frames of the image data; receive, from the imaging device, at least one frame of the one or more frames, the at least one frame including an image of the implantation site; identify, from the at least one frame of the image data, an abnormality at the implantation site; in response to identifying the abnormality, automatically trigger a supplemental image capture mode, wherein the imaging device, when operating in the supplemental image capture mode, is configured to capture one or more supplemental images of the implantation site; subsequent to triggering the supplemental image capture mode, receive the one or more supplemental images of the implantation site; and output the one or more supplemental images of the implantation site.

Example 24: A system according to Example 23, wherein the abnormality includes a potential infection at the implantation site, wherein to identify the abnormality, the one or more processors are configured to: determine, from the at least one frame, the presence of the potential infection at the implantation site; and determine, based at least in part on the at least one frame, a likelihood of an actual infection evidenced by the presence of an infectious agent at the implantation site.

Example 25: A system according to any of Examples 23 or 24, wherein to initiate the imaging device, the one or more processors are configured to: prior to receiving the at least one frame, receive at least one initial frame of the one or more frames of the image data; determine, from the at least one initial frame, a target adjustment of the imaging device, the target adjustment being configured to guide a user with adjusting the imaging device to achieve the target adjustment; and output, via a user interface, the target adjustment.

Example 26: A system according to any of Examples 23 through 25, wherein to identify the abnormality, the one or more processors are configured to: determine, based at least in part on the at least one frame, a likelihood of the abnormality; generate, based on the likelihood of the abnormality, a summary report identifying the abnormality; and output the summary report.

Example 27: A system according to Examples 26, wherein to determine the likelihood of the abnormality, the one or more processors are configured to: identify the abnormality in a plurality of perspective views, wherein the at least one frame represents a particular perspective view of the plurality of perspective views; determine, for each perspective view in which the abnormality is identified, a confidence interval for the identification of the abnormality; determine, according to the confidence interval, a number of perspective views of the plurality of perspective views for which the determined confidence interval satisfies a criterion; and determine, based at least in part on the number of perspective views, the likelihood of the abnormality.

Example 28: A system according to Example 27, wherein the one or more processors are further configured to:

receive, via the imaging device, each perspective view of the plurality of perspective views as each comprising a plurality of zoom levels.

Example 29: A system according to any of Examples 23 through 28, wherein the at least one frame comprises a plurality of frames of the image data, and wherein to receive the plurality of frames of the image data, the one or more processors are configured to: receive a first frame relative to a first perspective view of the implantation site; and subsequent to receiving the first frame, receive a second frame relative to a second perspective view of the implantation site, wherein the first perspective view and the second perspective view differ from one another.

Example 30: A system according to Example 29, wherein to identify the abnormality, the one or more processors are configured to: subsequent to receiving the first frame, identify, from the second frame of the image data, the abnormality at the implantation site.

Example 31: A system according Example 30, wherein to automatically trigger the supplemental image capture mode, the one or more processors are configured to: in response to identifying the abnormality in the second frame, automatically trigger the supplemental image capture mode.

Example 32: A system according to any of Examples 23 through 31, wherein the at least one frame comprises a first frame representing a first perspective view, wherein to receive the one or more supplemental images of the implantation site, the one or more processors are configured to: receive one or more supplemental images of the implantation site; and identify, from the one or more supplemental images of the implantation site, a second frame representing a second perspective view.

Example 33: A system according to any of Examples 23 through 32, wherein to receive the one or more supplemental images of the implantation site, the one or more processors are configured to: determine, from the at least one frame, a view of the implantation site that is depicted by the at least one frame; and identify the one or more supplemental images based at least in part on the view of the at least one frame.

Example 34: A system according to any of Examples 23 through 33, wherein to determine the imaging program, the one or more processors are configured to: determine a proficiency level of a user, the proficiency level indicative of a proficiency of the user with imaging implantation sites of IMDs; determine, based on the proficiency level, an imaging mode; and capture, according to the imaging mode, the at least one frame.

Example 35: A system according to any of Examples 23 through 34, wherein the supplemental image capture mode comprises a video capture mode, and wherein to output the one or more supplemental images of the implantation site, the one or more processors are configured to: output an imaging sequence, the imaging sequence based at least in part on the one or more supplemental images of the implantation site.

Example 36: A system according to Example 35, wherein the imaging device is configured to, in accordance with the video capture mode, produce the imaging sequence such that the imaging sequence satisfies a resolution criterion of at least 120 frames per second.

Example 37: A system according to any of Examples 23 through 36, wherein the imaging device is configured to operate in a first image capture mode, wherein the first image capture mode and the supplemental image capture mode differ from one another, and wherein the one or more processors are further configured to: receive, via the imaging device operating in the first image capture mode, the at least one frame; provide a notification that indicates the imaging device is transitioning from the first image capture mode to the supplemental image capture mode; receive, via the imaging device operating in the supplemental image capture mode, the one or more supplemental images of the implantation site; and subsequent to receiving the one or more supplemental images of the implantation site, determine, by the computing device, to revert to the first image capture mode.

Example 38: A system according to any of Examples 23 through 37, wherein to determine the identification data for the patient, the one or more processors are configured to: receive authentication data identifying a user of the imaging program; authorize the user to access the imaging program; subsequent to authorizing the user to access the imaging program, receive input data that identifies the patient of the IMD; and determine, from the input, the identification data for the patient.

Example 39: A system according to any of Examples 23 through 38, wherein the one or more processors comprise at least one processor of the imaging device.

Example 40: A system according to any of Examples 23 through 39, wherein the one or more processors comprise processing circuitry of a computing device.

In some implementations, the above-described Examples 1-22 and/or 23-40 can be implemented using an apparatus comprising one or more means for performing some or all of the various operations. As an Example 41, an apparatus for imaging and/or monitoring an implantation site of a patient includes: means for determining, via a computing device, identification data for the patient; means for identifying, based at least in part on the identification data, IMD information that corresponds to an IMD; means for determining, based at least in part on the IMD information, an imaging program that defines one or more parameters for imaging the implantation site; means for initiating, by the computing device, an imaging device, the imaging device configured to capture, in accordance with the imaging program, one or more frames of image data; means for receiving, via the imaging device, at least one frame of the one or more frames, the at least one frame including an image of the implantation site; means for identifying, from the at least one frame of the image data, an abnormality at the implantation site; means for triggering a supplemental image capture mode, wherein the imaging device, when operating in the supplemental image capture mode, is configured to capture one or more supplemental images of the implantation site; means for receiving, by the computing device, the one or more supplemental images of the implantation site; and means for outputting, via the computing device, the one or more supplemental images of the implantation site.

In some implementations, the above-described Examples 1-22 and/or 23-40 can be implemented using a computer-readable storage medium storing instructions that when executed cause one or more processors of a device to perform some or all of the various operations. As an Example 42, a computer-readable storage medium can be provided storing instructions that, when executed, cause one or more processors of a system or device for imaging or monitoring an implantation site of a patient to: determine identification data for a patient, the patient having or being with an IMD; identify, based at least in part on the identification data, IMD information that corresponds to the IMD; determine, based at least in part on the IMD information, an imaging program that defines one or more parameters for imaging an implantation site; initiate an imaging device, the imaging device configured to capture, in accordance with the imaging program, one or more frames of image data; receive, via the imaging device, at least one frame of the one or more frames, the at least one frame including an image of the implantation site; identify, from the at least one frame of the image data, an abnormality at the implantation site; in response to identifying the abnormality, automatically trigger a supplemental image capture mode, wherein the imaging device, when operating in the supplemental image capture mode, is configured to capture one or more supplemental images of the implantation site; subsequent to triggering the supplemental image capture mode, receive the one or more supplemental images of the implantation site; and output the one or more supplemental images of the implantation site.

Various examples have been described. However, one skilled in the art will appreciate that various modifications may be made to the described examples without departing from the scope of the claims. For example, although illustrated primarily as a handheld computing device, computing device(s) 2 may, in some instances, include a headset, such as an AR headset, that a user (e.g., patient 4, an HCP, etc.) may operate in order to assist patient 4 in the virtual check-in process. In one example, a user, separate from patient 4 may operate, as one of computing device(s) 2, camera 32 of a headset (e.g., an AR headset) in order to image the one or more implantation sites of patient 4. In such examples, the user may operate camera 32 in order to scan over the one or more implantation sites of patient 4, in accordance with one or more of the various techniques of this disclosure. That is, in one illustrative example, the techniques of this disclosure may be tailored such that computing device(s) 2 provides instructions, such as imaging-guidance instructions, via UI 22, that have been strategically tailored to effectively complement and support the example headset implementation, as would be understood by a person skilled in the art. In such instances, computing device(s) 2, or in some instances, another device, such as edge device(s) 12 and/or server(s) 94, may use the images or image sequences obtained via camera 32 of the headset in order to determine the presence of an abnormality at any particular implantation sites, in accordance with one or more techniques of this disclosure.

In another example, the techniques of this disclosure may be used to monitor various different implantation sites. In one example, processing circuitry 20 may identify IMD information, including implantation sites of battery powered components and/or locations of elongated leads that have been implanted. As such, processing circuitry 20 may determine an imaging program that includes guidance on imaging those areas of patient 4, as well. In an illustrative example, processing circuitry 20 may instruct patient 4 to image the implantation site (e.g., an implantation area) of an elongated lead that travels from a battery powered component implanted in the back of patient 4 up towards electrode leads implanted in the brain of patient 4.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Combinations of the above should also be included within the scope of computer-readable media.

Instructions may be executed by one or more processors, such as one or more DSPs, general purpose microprocessors, ASICs, FPGAs, CPLDs, or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Any of the above-mentioned "processors," and/or devices incorporating any of the above-mentioned processors or processing circuitry, may, in some instances, be referred to herein as, for example, "computers," "computer devices," "computing devices," "hardware computing devices," "hardware processors," "processing units," "processing circuitry," etc. Computing devices of the above examples may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In some examples, the computing devices may be controlled by a proprietary operating system. Conventional operating systems control and schedule computer processes for execution, perform memory management, provide file system, networking, I/O services, and provide UI functionality, such as GUI functionality, among other things.

The techniques of this disclosure may be implemented in a wide variety of devices or apparatuses, including an integrated circuit (IC) or a set of ICs (e.g., a chip set). Various components, modules, or units are described in this disclosure to emphasize functional aspects of devices configured to perform the disclosed techniques, but do not necessarily require realization by different hardware units.

Various examples have been described. These and other examples are within the scope of the following claims.

What is claimed is:

1. A method of monitoring an implantation site of a patient, the method comprising:

determining, by a computing device, an imaging program that defines one or more parameters for imaging the implantation site;

initiating, by the computing device, an imaging device, the imaging device including at least a camera of a mobile computing device and configured to capture, in accordance with the imaging program, image data of the implantation site;

identifying, by the computing device, from the image data of the implantation site, an abnormality at the implantation site;

automatically triggering, by the computing device and in response to identifying the abnormality, a supplemental image capture mode of the imaging device, wherein the imaging device, when operating in the supplemental image capture mode, is configured to capture one or more supplemental images of the implantation site; and outputting, via the computing device, the one or more supplemental images of the implantation site.

2. The method of claim 1, wherein the implantation site includes an implantation wound site or an implant-removal site on a body of the patient from implanting or removing an implantable medical device (IMD), wherein the image program that defines one or more parameters for imaging the implantation site is based on, at least in part, IMD information, and wherein the IMD information includes one or more of an IMD size, an IMD implantation location on a body of the patient, a location of elongated medical leads, a method to seal the implantation site, IMD communication protocol information, or an estimated orientation of the IMD.

3. The method of claim 1, wherein the abnormality at the implantation site includes one or more of: a potential infection at the implantation site, abnormal healing at the implantation site, device migration at the implantation site, an abnormality of stitching, an abnormality of adhesive, or an abnormality of wound closure at the implantation site.

4. The method of claim 1, wherein identifying the abnormality at the implantation site includes performing color filtering analysis on one or more frames of the image data.

5. The method of claim 1, further comprising:

subsequent to triggering the supplemental image capture mode, receiving, by the computing device, the one or more supplemental images of the implantation site.

6. The method of claim 1, wherein the image data comprises a first frame representing a first perspective view, wherein triggering the supplemental image capture mode comprises:

prompting a user, when the image device is operating in the supplemental image capture mode, to adjust the imaging device to capture a second frame representing a second perspective view, wherein the first perspective view and the second perspective view differ from one another; and identifying, from the one or more supplemental images of the implantation site, the second frame representing the second perspective view.

7. The method of claim 1, wherein the supplemental image capture mode comprises a video capture mode in which the imaging device is configured to capture an imaging sequence, and wherein outputting the one or more supplemental images of the implantation site comprises:

outputting, via the computing device, the imaging sequence, the imaging sequence based at least in part on the one or more supplemental images of the implantation site.

8. The method of claim 1, further comprising:

determining, by the computing device, a reference marker associated with the image data, wherein outputting the one or more supplemental images of the implantation site includes outputting the one or more supplemental images of the implantation site with the reference marker overlaid on the one or more supplemental images.

9. The method of claim 1, wherein outputting, via the computing device, the one or more supplemental images of the implantation site includes one or more of:

outputting the one or more supplemental images to a storage device; and outputting the one or more supplemental images to a user interface for display.

10. The method of claim 1, wherein the implantation site comprises one of a wound site, a surgical site, a procedurally prepared site, an implantation site an of an implantable medical device (IMD) or an implant removal site of an implantable medical device (IMD).

11. A system for monitoring an implantation site of a patient, the system comprising:

a memory configured to store image data; and one or more processors in communication with the memory, the one or more processors configured to:

determine an imaging program that defines one or more parameters for imaging the implantation site;

initiate an imaging device, the imaging device including at least a camera of a mobile computing device and configured to capture, in accordance with the imaging program, image data of the implantation site;

identify, from the image data of the implantation site, an abnormality at the implantation site;

automatically trigger, in response to identifying the abnormality, a supplemental image capture mode of the imaging device, wherein the imaging device, when operating in the supplemental image capture mode, is configured to capture one or more supplemental images of the implantation site; and output the one or more supplemental images of the implantation site.

12. The system of claim 11, wherein the implantation site includes an implantation wound site or an implant-removal site on a body of the patient from implanting or removing an implantable medical device (IMD), wherein the image program that defines one or more parameters for imaging the implantation site is based on, at least in part, IMD information, and wherein the IMD information includes one or more of an IMD size, an IMD implantation location on a body of the patient, a location of elongated medical leads, a method to seal the implantation site, IMD communication protocol information, or an estimated orientation of the IMD.

13. The system of claim 11, wherein the abnormality at the implantation site includes one or more of: a potential infection at the implantation site, abnormal healing at the implantation site, device migration at the implantation site, an abnormality of stitching, an abnormality of adhesive, or an abnormality of wound closure at the implantation site.

14. The system of claim 11, wherein to identify the abnormality at the implantation site, the one or more processors are configured to perform color filtering analysis on one or more frames of the image data.

15. The system of claim 11, wherein the one or more processors are configured to:

subsequent to triggering the supplemental image capture mode, receive the one or more supplemental images of the implantation site.

16. The system of claim 11, wherein the image data comprises a first frame representing a first perspective view, wherein to trigger the supplemental image capture mode, the one or more processors are configured to:

prompt a user, when the image device is operating in the supplemental image capture mode, to adjust the imaging device to capture a second frame representing a second perspective view, wherein the first perspective view and the second perspective view differ from one another; and identify, from the one or more supplemental images of the implantation site, the second frame representing the second perspective view.

17. The system of claim 11, wherein the supplemental image capture mode comprises a video capture mode in which the imaging device is configured to capture an imaging sequence, and wherein to output the one or more supplemental images of the implantation site, the one or more processors are configured to:

output the imaging sequence, the imaging sequence based at least in part on the one or more supplemental images of the implantation site.

18. The system of claim 11, wherein the one or more processors are configured to:

determine a reference marker associated with the image data, wherein to output the one or more supplemental images of the implantation site, the one or more processors are configured to output the one or more supplemental images of the implantation site with the reference marker overlaid on the one or more supplemental images.

19. The system of claim 11, wherein to output, the one or more supplemental images of the implantation site, the one or more processors are configured to:

output the one or more supplemental images to a storage device; and output the one or more supplemental images to a user interface for display.

20. The system of claim 11, wherein the implantation site comprises one of a wound site, a surgical site, a procedurally prepared site, an implantation site an of an implantable medical device (IMD) or an implant removal site of an implantable medical device (IMD).

21. The system of claim 11, wherein IMD comprises an implantable mesh.

* * * * *